US007722861B2

(12) United States Patent
Jacobs et al.

(10) Patent No.: US 7,722,861 B2
(45) Date of Patent: May 25, 2010

(54) **ATTENUATED *MYCOBACTERIUM TUBERCULOSIS* VACCINES**

(76) Inventors: William R. Jacobs, 47 Iden Ave., Pelham, NY (US) 10803; Tsungda Hsu, 1737 Haight Ave., Bronx, NY (US) 10461; Stoyan Bardarov, Bronx, NY (US); Svetoslav Bardarov, legal representative, 17 Duncannon Ave. #9, Worcester, MA (US) 01604; Vasan Sambandamurthy, 1935 Eastchester Rd., Apt. 25G, Bronx, NY (US) 10461

( * ) Notice: Subject to any disclaimer, the term of this patent is extended or adjusted under 35 U.S.C. 154(b) by 313 days.

(21) Appl. No.: 10/351,452

(22) Filed: Jan. 24, 2003

(65) Prior Publication Data

US 2004/0001866 A1  Jan. 1, 2004

Related U.S. Application Data

(60) Provisional application No. 60/358,152, filed on Feb. 19, 2002.

(51) Int. Cl.
*A01N 63/00* (2006.01)
*A61K 48/00* (2006.01)
*A61K 39/04* (2006.01)

(52) U.S. Cl. .................... 424/93.2; 536/23.1; 536/23.7; 435/243; 435/253.1; 435/440; 424/9.1; 424/9.2; 424/184.1; 424/185.1; 424/190.1; 424/234.1; 424/248.1

(58) Field of Classification Search .................. 424/9.1, 424/9.2, 93.2, 184.1, 185.1, 190.1, 234.1, 424/248.1; 435/243, 253.1, 440; 536/23.1, 536/23.7

See application file for complete search history.

(56) References Cited

U.S. PATENT DOCUMENTS

| | | | |
|---|---|---|---|
| 5,750,384 A | 5/1998 | Jacobs, Jr. et al. | |
| 5,837,732 A | 11/1998 | Sacchettini et al. | |
| 5,958,077 A | 9/1999 | Anderson et al. | |
| 5,968,733 A | 10/1999 | Bloom et al. | |
| 5,972,700 A | 10/1999 | Jacobs, Jr. | |
| 6,015,890 A | 1/2000 | Jacobs, Jr. et al. | |
| 6,221,364 B1 | 4/2001 | Pavelka et al. | |
| 6,221,365 B1 | 4/2001 | Jones | |
| 6,268,201 B1 | 7/2001 | Alland et al. | |
| 6,271,034 B1 | 8/2001 | Bardarov et al. | |
| 6,290,966 B1 | 9/2001 | Cox et al. | |
| 6,291,190 B1 * | 9/2001 | Behr et al. | 435/7.1 |
| 6,387,694 B1 | 5/2002 | McKinney et al. | |
| 6,423,545 B1 * | 7/2002 | Pavelka et al. | 435/477 |
| 6,562,348 B2 | 5/2003 | Hondalus et al. | |
| 6,566,121 B1 | 5/2003 | Jacobs, Jr. et al. | |
| 6,733,761 B2 | 5/2004 | McKinney et al. | |
| 6,752,994 B2 | 6/2004 | Jacobs, Jr. et al. | |
| 6,821,769 B2 | 11/2004 | Alland et al. | |
| 2003/0059441 A1 | 3/2003 | Pavelka et al. | |
| 2005/0260232 A1 | 11/2005 | Sambandamurthy et al. | |

FOREIGN PATENT DOCUMENTS

| | | |
|---|---|---|
| WO | WO 2003/070164 A2 | 8/2003 |
| WO | WO 2004/066298 | 8/2004 |
| WO | WO 2006/076343 A1 | 7/2006 |
| WO | WO 2006/076517 A1 | 7/2006 |
| WO | WO 2006/076519 A2 | 7/2006 |

OTHER PUBLICATIONS

Mahairas, G., et al, "Molecular analysis of genetic differences between Mycobacerium bovis BCG and Virulent M. bovis" Journal of Bacteriology, vol. 178, No. 5, pp. 1274-1282, MAr. 1996.*
Brennan, M.J., et al. "Tuberculosis vacine development: research, regulatory and clinical strategies", Expert Opin. Biol. Ther., vol. 4, No. 9, pp. 1493-1504, 2004.*
Orme, I.M. "Beyond BCG: the potential for a more effective TB vaccine", Molecular medicine Today, vol. 5, pp. 487-492, 1999.*
Collins, F.M. "New generation tuberculosis vaccines", Clinical Microbiology Newsletter, vol. 23, No. 3, pp. 17-23, 2001.*
Andersen, P., "Host Responses and Antigens Involved in Protective Immunity to *Mycobacterium tuberculosis*"; Scand. J. Immunol. 1997, pp. 115-131, vol. 45.
Andersen, P., et al., "Proteins Released from *Mycobacterium tuberculosis* during Growth"; Infection and Immunity, Jun. 1991, pp. 1905-1910, vol. 59, No. 6.
Behr, M.A., et al., "Comparative Genomics of BCG Vaccines by Whole-Genome DNA Microarray"; Science, May 28, 1999, pp. 1520-1523, vol. 284.
Camacho, L.R., et al., "Identification of a virulence gene cluster of *Mycobacterium tuberculosis* by signature-tagged transposon mutagenesis"; Molecular Microbiology, 1999, pp. 257-267, vol. 34.
Chambers, M.A., et al., "Identification of a Mycobacterium bovis BCG Auxtrophic Mutant That Protects Guinea Pigs against M. bovis and Hematogenous Spread of *Mycobacterium tuberculosis* without Sensitization to Tuberculin"; Infection and Immunity, Dec. 2000, pp. 7094-7099, vol. 68, No. 12.

(Continued)

*Primary Examiner*—Rodney P. Swartz
(74) *Attorney, Agent, or Firm*—Amster, Rothstein Ebenstein LLP

(57) ABSTRACT

Non-naturally occurring mycobacteria in the *Mycobacterium tuberculosis* complex are provided. These mycobacteria have a deletion of an RD1 region or a region controlling production of a vitamin, and exhibit attenuated virulence in a mammal when compared to the mycobacteria without the deletion. Also provided are non-naturally occurring mycobacteria that have a deletion of a region controlling production of lysine, and mycobacteria comprising two attenuating deletions. Vaccines comprising these mycobacteria are also provided, as are methods of protecting mammals from virulent mycobacteria using the vaccines. Also provided are methods of preparing these vaccines which include the step of deleting an RD1 region or a region controlling production of a vitamin from a mycobacterium in the *M. tuberculosis* complex.

23 Claims, 22 Drawing Sheets

OTHER PUBLICATIONS

Cole, S.T., et al., "Deciphering the biology of *Mycobacterium tuberculosis* from the complete genome sequence"; Nature, Jun. 11, 1998, pp. 537-544+table pages, vol. 393.

COX, J., et al., "Complex lipid determines tissue-specific replication of *Mycobacterium tuberculosis* in mice"; Nature, Nov. 4, 1999, pp. 79-83, vol. 402.

De Voss, J.J., et al. "The salicylate-derived mycobactin siderophores of *Mycobacterium tuberculosis* are essential for growth in macrophages"; PNAS, Feb. 1, 2000, pp. 1252-1257, vol. 97, No. 3.

Glickman, M.S., et al., "The *Mycobacterium tuberculosis* cmaA2 Gene Encodes a Mycolic Acid trans-Cyclopropane Synthetase"; The Journal of Biological Chemistry, Jan. 19, 2001, pp. 2228-2233, vol. 276, No. 3.

Gordon, S.V., et al., "Genomics of Mycobacterium bovis"; Tuberculosis, 2001, pp. 157-163, vol. 81(1/2).

Guleria, I., et al., " Auxotrophic vaccines for tuberculosis"; Nature Medicine, Mar. 1996, pp. 334-337, vol. 2, No. 3.

Hondalus, M.K., et al., "Attenuation of and Protection Induced by a Leucine Auxotroph of *Mycobacterium tuberculosis*"; Infection and Immunity, May 2000, pp. 2888-2898, vol. 68, No. 5.

Jackson, M., et al., "Persistence and Protective Efficacy of a *Mycobacterium tuberculosis* Auxotroph Vaccine"; Infection and Immunity, Jun. 1999, pp. 2867-2873, vol. 67, No. 6.

Mahairas, G.G., et al., "Molecular Analysis of Genetic Differences between Mycobacterium bovis BGG an Virulent M. bovis"; Journal of Bacteriology, Mar. 1996, pp. 1274-1282, vol. 178, No. 5.

Manca, C., et al., "Virulence of a *Mycobacterium tuberculosis* clinical isolate in mice is determined by failure to induce Th1 type immunity and is associated with induction of IFN-alpha/beta"; PNAS, May 8, 2001, pp. 5752-5757, vol. 98, No. 10.

McKinney, J.D., et al., "Persistence of *Mycobacterium tuberculosis* in macrophages and mice requires the glyoxylate shunt enzyme isocitrate lyase"; Nature, Aug. 17, 2000 pp. 735-738, vol. 406.

Pavelka, Jr., M.S. and Jacobs, Jr., W.R., "Comparison of the Construction of Unmarked Deletion Mutations in Mycobacterium smegmatis, Mycobacterium bovis, Bacillus Calmette-Guerin, and *Mycobacterium tuberculosis* H37Rv by Allelic Exchange", Journal of Bacteriology, Aug. 1999, pp. 4780-4789, vol. 181, No. 16.

Sambandamurthy, V.K., et al. "A pantothenate auxotroph of *Mycobacterium tuberculosis* is highly attenuated and protects mice against tuberculosis"; Nature Medicine, Oct. 2002, pp. 1171-1174, vol. 8, No. 10.

Slyshenkov, V.S., et al., "Pantothenic Acid and Its Derivatives Protect Ehrlich Ascites Tumor Cells Against Lipid Peroxidation"; Free Radical Biology & Medicine, 1995, pp. 767-772, vol. 19, No. 6.

Smith, D.A., et al. "Characterization of Auxotrophic Mutants of *Mycobacterium tuberculosis* and Their Potential as Vaccine Candidates"; Infection and Immunity, Feb. 2001, pp. 1142-1150, vol. 69 No. 2.

Dascher et al. "Immunization with a mycobacterial lipid vaccine improves pulmonary pathology in the guinea pig model of tuberculosis," Intl. Immuno. Aug. 2003, pp, 915-25, 402, 2003.

Harboe, "Evidence for ocourance of ESAT-6 Protein in mycobacterium tuberculosis and virulent mycobacterium bovis and for its absence in mycobacterium bovic BCG." Infection and Immunity, Jan. 1996, pp. 16-22, vol. 64, No. 8.

Hernanidez-Pando at al., "Pathogenesis of Tuberculosis in Mice Exposed to Low and High Doses of an Environmental Mycobacterial Saprophtye before Infection"; Infection and Immunity, Aug. 1997, pp. 3317-3327, vol. 65, No. 8.

Moreira et al., "Mycobacterial Antigens Exacerbate Disease Manifestations in Mycobacterium tuberculosis•Infected Mice"; Infection and Immunity, Apr. 2002, pp. 2100-2107, 70:4.

Sambandamurthy et al., Long-Term Protection against Tuberculosis following Vaccination with a Severely Attenuated Double Lysine and Pantothenate Auxotroph of Mycobacterium tuberculosis; Infection and Immunity, Feb. 2005, pp. 1196-203, vol. 73 a c b

ATTENUATED MYCOBACTERIUM TUBERCULOSIS VACCINES

CROSS-REFERENCE TO RELATED APPLICATION

This application claims the benefit of U.S. Provisional Application No. 60/358,152, filed Feb. 19, 2002. That application is incorporated by reference herewith in its entirety.

STATEMENT REGARDING FEDERALLY SPONSORED RESEARCH OR DEVELOPMENT

The present invention was supported by NIH Grant No. AI26170. As such, the U.S. Government has certain rights in the invention.

BACKGROUND OF THE INVENTION (1) Field of the Invention

The present invention generally relates to live bacterial vaccines. More specifically, the invention is related to novel *Mycobacterium sp.* compositions, and the use of those compositions to protect mammals against disease caused by virulent *Mycobacterium* sp.

(2) Description of the Related Art

REFERENCES CITED

Abiko, Y. in *Metabolic Pathways*. D. M. Greenburg, Ed. (Academic Press, New York, 1975).

Afshar, K., Gonczy, P., DiNardo, S. & Wasserman, S. A. fumble encodes a pantothenate kinase homolog required for proper mitosis and meiosis in *Drosophila melanogaster*. Genetics 157, 1267-76. (2001).

Andersen, P. Host responses and antigens involved in protective immunity to *Mycobacterium tuberculosis*. Scand. J. Immunol. 45, 115-31 (1997).

Andersen, P., Askgaard, D., Ljungqvist, L., Bennedsen, J. & I. Heron. Proteins released from *Mycobacterium tuberculosis* during growth. Infect. Immun. 59, 1905-10. (1991).

Balasubramanian, V., et al. Allelic exchange in *Mycobacterium tuberculosis* with long linear recombination substrates. J. Bacteriol. 178, 273-9 (1996).

Baldwin, S. L. et al. Evaluation of new vaccines in the mouse and guinea pig model of tuberculosis. Infect. Immun. 66, 2951-2959 (1998).

Bardarov, S. et al. Conditionally replicating mycobacteriophages: a system for transposon delivery to *Mycobacterium tuberculosis*. Proc. Natl. Acad. Sci. USA 94, 10961-6. (1997).

Bardarov, S. et al. Microbiology 148, 3007-17 (2002).

Behar, S. M., et al. Susceptibility of mice deficient in CD1D or TAP1 to infection with *Mycobacterium tuberculosis*. J. Exp. Med. 189, 1973-80 (1999).

Behr, M. A. et al. Comparative genomics of BCG vaccines by whole-genome DNA microarray [see comments]. Science 284, 1520-3 (1999).

Bermudez, L. E., Sangari, F. J., Kolonoski, P., Petrofsky, M. and J. Goodman. Infect. Immun. 71, 140-146 (2002).

Berthet, F. X., Rasmussen, P. B., Rosenkrands, I., Andersen, P. & B. A. Gicquel. *Mycobacterium tuberculosis* operon encoding ESAT-6 and a novel low-molecular-mass culture filtrate protein (CFP-10). Microbiology 144, 3195-203. (1998).

Bloom, B. R. & P. Fine, in Tuberculosis pathogenesis, protection, and control (ed. Bloom, B. R.) (American Society for Microbiology, Washington, D.C., 1994).

Calmette, A. & C. Guerin. Origine intestinale de la tuberculose pulmonaire. Ann. Inst. Pasteur 19, 601-618 (1905).

Calmette, A. & C. Guerin. C. R. Acad. Sci. 149, 716 (1909).

Calmette, A. & C. Guerin. Ann. Inst. Pasteur 34, 553 (1920).

Calmette, A. & H. Plotz. Protective inoculation against tuberculosis with BCG. Am. Rev. Tuberc. 19, 567-572 (1929).

Camacho, L. R., Ensergueix, D., Perez, E., Gicquel, B. & Guilhot, C. Identification of a virulence gene cluster of *Mycobacterium tuberculosis* by signature-tagged transposon mutagenesis. Mol Microbiol 34, 257-67. (1999).

Canaday, D. H. et al. Activation of human CD8+alpha beta TCR+cells by *Mycobacterium tuberculosis* via an alternate class I MHC antigen-processing pathway. J. Immunol. 162, 372-9 (1999).

Carriere, C. et al. Conditionally replicating luciferase reporter phages: improved sensitivity for rapid detection and assessment of drug susceptibility of *Mycobacterium tuberculosis*. J. Clin. Microbiol. 35, 3232-9. (1997).

Chambers, M. A. et al. Identification of a *Mycobacterium bovis* BCG auxotrophic mutant that protects guinea pigs against *M. bovis* and hematogenous spread of *Mycobacterium tuberculosis* without sensitization to tuberculin. Infect. Immun. 68, 7094-9 (2000).

Cho, S. et al. Antimicrobial activity of MHC class I-restricted CD8+T cells in human tuberculosis. Proc. Natl. Acad. Sci. USA 97, 12210-5 (2000).

Cirillo, J. D. et al. A novel transposon trap for mycobacteria: isolation and characterization of IS1096. J. Bacteriol. 173, 7772-80 (1991).

Colditz G. A. et al. Pediatrics 96, 29-35. (1995).

Cole, S. T. et al. Deciphering the biology of *Mycobacterium tuberculosis* from the complete genome sequence [see comments] [published erratum appears in Nature Nov. 12, 1998; 396(6707):190]. Nature 393, 537-44 (1998).

Collins, F. M. Protection to mice afforded by BCG vaccines against an aerogenic challenge by three mycobacteria of decreasing virulence. Tubercle 66, 267-76. (1985).

Collins, F. M. Antituberculous immunity: new solutions to an old problem. Rev Infect Dis. 13, 940-50 (1991).

Cox, J. S., Chen, B., McNeil, M. & W. R. Jacobs, Jr. Complex lipid determines tissue-specific replication of *Mycobacterium tuberculosis* in mice. Nature 402, 79-83 (1999).

D'Souza, C. D. et al. An anti-inflammatory role for gamma delta T lymphocytes in acquired immunity to *Mycobacterium tuberculosis*. J. Immunol. 158, 1217-21 (1997).

D'Souza, C. D. et al. A novel nonclassic beta2-microglobulin-restricted mechanism influencing early lymphocyte accumulation and subsequent resistance to tuberculosis in the lung. Am. J. Respir. Cell. Mol. Biol. 23, 188-93 (2000).

De Voss, J. J. et al. The salicylate-derived mycobactin siderophores of *Mycobacterium tuberculosis* are essential for growth in macrophages. Proc Natl Acad Sci USA 97, 1252-7. (2000).

Delogu, G. et al. Infect. Immun. 70, 293-302 (2002).

Dobos, K., Spotts, E., Quinn, F., & C. King. Infect. Immun. 68, 6300-6310 (2000).

Dolin, P. J., Raviglione, M. C. & A. Kochi. Global tuberculosis incidence and mortality during 1990-2000. Bull. World Health Organ. 72, 213-220 (1994).

Dubos, R. & W. Schaefer. Am. Rev. Tuberculous Pulm. Dis. 74, 541-551 (1956).

Dye, C., Scheele, S., Dolin, P., Pathania, V. & M. C. Raviglione. Consensus statement. Global burden of tuberculosis: estimated incidence, prevalence, and mortality by country. WHO Global Surveillance and Monitoring Project. JAMA 282, 677-686 (1999).

Elgert, K. D. Immunology, Wiley Liss, Inc., (1996).

Feng, C. G. et al. Increase in gamma interferon-secreting CD8(+), as well as CD4(+), T cells in lungs following aerosol infection with *Mycobacterium tuberculosis*. Infect. Immun. 67, 3242-7 (1999).

Fine, P. E. Lancet 346, 1339-45. (1995).

Fine, P. M. & Rodrigues, L.C. Modem vaccines: mycobacterial disease. Lancet 335, 1016-1020 (1990).

Finlay, B. B. & S. Falkow. Microbiol. Mol. Biol. Rev. 61, 136-69. (1997).

Fritz, C., Maass, S., Kreft, A. & F. C. Bange. Infect. Immun 70, 286-91. (2002).

Gennaro, Ed. Remington's Pharmaceutical Sciences, 17th Edition, (Mack Publishing Co., Easton, Pa., 1985).

Gheorghiu, M. in Vaccinia, Vaccination, and Vaccinology: Jenner, Pasteur and their successors (eds. Plotkin, S. A. & Fantini, B.) 87-94 (Elsevier, Paris, 1996).

Glickman, M. S., Cox, J. S. & W. R. Jacobs, Jr. A novel mycolic acid cyclopropane synthetase is required for coding, persistence, and virulence of *Mycobacterium tuberculosis*. Mol. Cell 5, 717-27 (2000).

Glickman, M. S., Cahill, S. M. & W. R. Jacobs, Jr. The *Mycobacterium tuberculosis* cmaA2 gene encodes a mycolic acid transcyclopropane synthetase. J. Biol. Chem. 276, 2228-33. (2001).

Gordon, S. V. et al. Genomics of *Mycobacterium bovis*. Tuberculosis 81, 157-63 (2001).

Grange, J. M., Gibson, J., Osborn, T. W., Collins, C. H. & M. D. Yates. What is BCG? Tubercle 64, 129-39. (1983).

Guleria, I. et al. Auxotrophic vaccines for tuberculosis. Nat. Med. 2, 334-7 (1996).

Hart, P. D. & I. Sutherland. BCG and vole *bacillus* vaccines in the prevention of tuberculosis in adolescence and early life. Br. Med. J. 22, 2293-2295 (1977).

Hepper, K. P. & F. M. Collins. Immune responsiveness in mice heavily infected with M. kansasii. Immunol. 53, 357-364 (1984).

Hernandez-Pando, R., Schon, T., Orozco, R., Serafin, J. & I. Estrada-Garcia. Exp. Tox. Path. 53, 257-265 (2001).

Homchampa, P., Strugnell, R. A. and B. Adler. Molecular analysis of the aroA gene of *Pasteurella multocida* and vaccine potential of a constructed aroA mutant. Mol Microbiol. 6, 3585-93 (1992).

Hondalus, M. K. et al. Attenuation of and protection induced by a leucine auxotroph of *Mycobacterium tuberculosis*. Infect. Immun. 68, 2888-98 (2000).

Honer zu Bentrup, K. & D. G. Russell. Trends Microbiol. 9, 597-605. (2001).

Hubbard, R. D., Flory, C. M., Cocito, C. & F. M. Collins. Immunization of mice with antigen A60 of *Mycobacterium bovis* BCG. Clin. Exp. Immunol. 88, 129-131 (1992).

Hutter, B. & T. Dick. FEMS Microbiol. Lett 178, 63-9. (1999).

Jackowski, S. & J. H. Alix. J. Bacteriol. 172, 3842-8. (1990).

Jackowski, S. in *Escherichia coli and Salmonella typhimurium: Cellular and Molecular Biology*. F. C. Neidhardt, R. Curtiss, et al., Eds. (American Society for Microbiology, Washington, D.C., ed. Second, 1996).

Jackson, M. et al. Infect. Immun. 67, 2867-73. (1999).

Jacobs, W.R., Jr., Tuckman, M. & B. R. Bloom. Introduction of foreign DNA into mycobacteria using a shuttle phasmid. Nature 327, 532-5. (1987).

Jones, B. E. et al. Relationship of the manifestations of tuberculosis to CD4 cell counts in patients with human immunodeficiency virus infection. Am. Rev. Respir. Dis. 148, 1292-7 (1993).

Kalpana, G. V., Bloom, B. R. & W. R. Jacobs, Jr. Insertional mutagenesis and illegitimate recombination in mycobacteria. Proc. Natl. Acad. Sci. USA 88, 5433-7 (1991).

Kanai, K. & K. Yanagisawa. Jpn. J. Med. Sci. Biol. 8, 115-127 (1955).

Kaufmann, S. H., Ladel, C. H. & I. E. Flesch. T cells and cytokines in intracellular bacterial infections: experiences with *Mycobacterium bovis* BCG. Ciba Found. Symp. 195, 123-32 (1995).

Kaushal, D. et al. Reduced immunopathology and mortality despite tissue persistence in a *Mycobacterium tuberculosis* mutant lacking alternative sigma factor, SigH. Proc. Natl. Acad. Sci. USA 99, 8330-5. (2002).

Kirby, J. E., Vogel, J. P., Andrews, H. L. & R. R. Isberg. Mol. Microbiol. 27, 323-336 (1998).

Koch, R. Die Aetiologie der Tuberculos. Ber. Klin. Wochenschr. 19, 221-253 (1882).

Lalvani, A. et al. Human cytolytic and interferon gamma-secreting CD8+T lymphocytes specific for *Mycobacterium tuberculosis*. Proc. Natl. Acad. Sci. USA 95, 270-5 (1998).

Lalvani, A. et al. J. Infect. Dis. 183, 469-477 (2001).

Lashuel, H. A. et al. Nature 418, 291 (2002).

Lee, M. H., Pascopella, L., Jacobs, W. R., Jr. & G. F. Hatfull. Site-specific integration of mycobacteriophage L5: integration-proficient vectors for *Mycobacterium smegmatis*, *Mycobacterium tuberculosis*, and bacille Calmette-Guerin. Proc. Natl. Acad. Sci. USA 88, 3111-5. (1991).

Lewinsohn, D. M. et al. *Mycobacterium tuberculosis*-reactive CD8+T lymphocytes: the relative contribution of classical versus nonclassical HLA restriction. J. Immunol. 165, 925-30 (2000).

Mahairas, G. G., Sabo, P. J., Hickey, M. J., Singh, D. C. & C. K. Stover. Molecular analysis of genetic differences between *Mycobacterium bovis* BCG and virulent *M. bovis*. J. Bacteriol 178, 1274-82 (1996).

Manca, C. et al. Virulence of a *Mycobacterium tuberculosis* clinical isolate in mice is determined by failure to induce Th1 type immunity and is associated with induction of IFN-alpha/beta. Proc. Natl. Acad. Sci. USA 98, 5752-7. (2001).

McAdam, R. A., et al. In vivo growth characteristics of leucine and methionine auxotrophic mutants of *Mycobacterium bovis* BCG generated by transposon mutagenesis. Infect. Immun. 63, 1004-12 (1995).

P. J. McGuire, P. J. et al. Appl. Env. Micro. 68, 4646-9 (2002).

McDonough, K. A. & Y. Kress. Infect. Immun. 63, 4802-4811 (1995).

McKenney, D. et al. Science 284, 1523-7. (1999).

McKinney, J. D. et al., Nature 406, 735-8. (2000).

Mogues, T., et al. The relative importance of T cell subsets in immunity and immunopathology of airborne *Mycobacterium tuberculosis* infection in mice. J. Exp. Med. 193, 271-80 (2001).

Mohagheghpour, N., et al. CTL response to *Mycobacterium tuberculosis*: identification of an immunogenic epitope in the 19-kDa lipoprotein. J. Immunol. 161, 2400-6 (1998).

Morita, C. T., R. A. Mariuzza & M. B. Brenner. Antigen recognition by human gamma delta T cells: pattern recognition by the adaptive immune system. Springer Semin. Immunopathol. 22, 191-217 (2000).

Mukadi, Y., et al. Spectrum of immunodeficiency in HIV-1-infected patients with pulmonary tuberculosis in Zaire. Lancet 342, 143-6 (1993).

Muller, I., et al. Impaired resistance to *Mycobacterium tuberculosis* infection after selective in vivo depletion of L3T4+ and Lyt-2+T cells. Infect. Immun. 55, 2037-41 (1987).

Murray, C. J. & J. A. Salomon. Proc. Natl. Acad. Sci. USA 95, 13881-6. (1998).

Nassi, S. et al. Biochemistry 41, 1445-1450 (2002).

Opie, E. L. & J. Freund J. An experimental study of protective inoculation with heat killed *tubercule bacilli*. J. Exp. Med. 66, 761-788 (1937).

M. Pallen, M. Trends in Microbiol. 10, 209-212 (2002).

Parish, T. & N. G. Stoker. Use of a flexible cassette method to generate a double unmarked *Mycobacterium tuberculosis* tlyA plcABC mutant by gene replacement. Microbiol. 146, 1969-1975 (2000).

Pascopella, L. et al. Use of in vivo complementation in *Mycobacterium tuberculosis* to identify a genomic fragment associated with virulence. Infect. Immun. 62, 1313-9. (1994).

Pavelka, M. S., Jr. & W. R. Jacobs, Jr. Comparison of the construction of unmarked deletion mutations in *Mycobacterium smegmatis*, *Mycobacterium bovis bacillus* Calmette-Guerin, and *Mycobacterium tuberculosis* H37Rv by allelic exchange. J. Bacteriol. 181, 4780-9 (1999).

Pedrazzini, T., Hug, K. & J. A. Louis Importance of L3T4+ and Lyt-2+cells in the immunologic control of infection with *Mycobacterium bovis* strain *bacillus* Calmette-Guerin in mice. Assessment by elimination of T cell subsets in vivo. J. Immunol. 139, 2032-7 (1987).

Pelicic, V., Reyrat, J. M. & B. Gicquel. Generation of unmarked directed mutations in mycobacteria, using sucrose counter-selectable suicide vectors. Mol. Microbiol. 20, 919-25. (1996).

Pelicic, V. et al. Efficient allelic exchange and transposon mutagenesis in *Mycobacterium tuberculosis*. Proc. Natl. Acad. Sci. USA 94, 10955-60 (1997).

Pethe, K. et al. Nature 412, 190-194 (2001).

Petroff, S. A., Branch, A. & W. Steenken, Jr. A study of *Bacillus* Calmette-Guerin. 1. Biological characteristics, cultural 'dissociation' and animal experimentation. Am. Rev. Tuberc. 9, 46 (1929).

Prasad, P. D. et al. J. Biol. Chem. 273, 7501-6. (1998).

Prasad, P. D. & V. Ganapathy. Curr. Opin. Clin. Nutr. Metab. Care 3, 263-6. (2000).

Pym, A. S. et al. Mol. Microbio. 46, 709-717 (2002).

Raman, S. et al. The alternative sigma factor SigH regulates major components of oxidative and heat stress responses in *Mycobacterium tuberculosis*. J. Bacteriol. 183, 6119-25. (2001).

Renshaw, P. et al. J. Biol. Chem. 277, 21598-21603 (2002).

Rodrigues, L. C., Gill, N. & Smith, P. G. BCG vaccination in the first year of life protects children of Indian subcontinent ethnic origin against tuberculosis in England. J. Epidemiol. 45, 78-80 (1991).

Rosat, J. P. et al. CD1-restricted microbial lipid antigen-specific recognition found in the CD8+alpha beta T cell pool. J. Immunol. 162, 366-71 (1999).

Saliba, K. J. & K. Kirk. J. Biol. Chem. 276, 18115-21 (2001).

Sambandamurthy, V. K. et al. Nature Med. 10, 1171-4 (2002).

Scanga, C. A. et al. Depletion of CD4(+) T cells causes reactivation of murine persistent tuberculosis despite continued expression of interferon gamma and nitric oxide synthase 2. J. Exp. Med. 192, 347-58 (2000).

Serbina, N. V. and J. L. Flynn. CD8(+) T cells participate in the memory immune response to *Mycobacterium tuberculosis*. Infect. Immun. 69, 4320-8 (2000).

Shen, Y. et al. Antiretroviral agents restore *Mycobacterium*-specific T-cell immune responses and facilitate controlling a fatal tuberculosis-like disease in Macaques coinfected with simian immunodeficiency virus and *Mycobacterium bovis* BCG. J. Virol. 75, 8690-6 (2001).

Shen, Y., Zhou, D., Chalifoux, L., Simon, M., Shen, L., Li, P., Sehgal, P. K., Letvin, N. L. & Z. W. Chen. Induction of an simian immunodeficiency virus-related tuberculosis-like disease in macaques: An animal model for AIDS virus/*mycobacterium* coinfection. Infect. Immun. 70, 869-77 (2001).

Silva, C. L. & D. B. Lowrie. Identification and characterization of murine cytotoxic T cells that kill *Mycobacterium tuberculosis*. Infect. Immun. 68, 3269-74 (2000).

Skjot, R. et al., Infect. Immun. 68, 214-220 (2000).

Slyshenkov, V. S., Rakowska, M., Moiseenok, A. G. & L. Wojtczak. Free Radic. Biol. Med. 19, 767-72. (1995).

Slyshenkov, V. S., Moiseenok, A. G. & Wojtczak, L. Noxious effects of oxygen reactive species on energy-coupling processes in *Ehrlich ascites* tumor mitochondria and the protection by pantothenic acid. Free Radic Biol Med 20, 793-800 (1996).

Slyshenkov, V. S., Piwocka, K., Sikora, E. & L. Wojtczak. Free Radic. Biol. Med. 30, 1303-10. (2001).

Smith, D. A., Parish, T. Stoker, N. G. & G. J. Bancroft, Infect. Immun. 69, 1142-50. (2001).

Snapper, S. B. et al. Lysogeny and transformation in mycobacteria: stable expression of foreign genes. Proc. Natl. Acad. Sci. USA 85, 6987-91. (1988).

Sousa, A. O. et al. Relative contributions of distinct MHC class I-dependent cell populations in protection to tuberculosis infection in mice. Proc. Natl. Acad. Sci. USA 97, 4204-8 (2000).

Stenger, S. et al. Differential effects of cytolytic T cell subsets on intracellular infection. Science 276, 1684-7 (1997).

Stites et al. Basic & Clinical Immunology; 7th Ed., Appleton & Lange, (1991).

Steyn, A. J. et al. *Mycobacterium tuberculosis* WhiB3 interacts with RpoV to affect host survival but is dispensable for in vivo growth. Proc. Natl. Acad. Sci. USA 99, 3147-52. (2002).

Teitelbaum, R. et al. Immun. 10, 641-50 (1999).

Theuer, C. P. et al. Human immunodeficiency virus infection in tuberculosis patients. J Infect Dis. 162, 8-12 (1990).

Tuberculosis Prevention Trial. Trial of BCG vaccines in South India for tuberculosis prevention. Indian J. Med. Res. 72, 1-74 (1980).

Vallari, D. S. & C, O. Rock. J. Bacteriol. 164, 136-42. (1985).

van Pinxteren, L. et al. Clin. Diagn. Lab. Immunol. 7, 155-160 (2000).

Weber, I., Fritz, C., Ruttkowski, S., Kreft, A. & F. C. Bange. Mol. Microbiol. 35, 1017-25. (2000).

Weill-Halle, B. & Turpin, R. Premiers essais de vaccination antituberculeuse de l'enfant par le bacille Calmette-Guerin (BCG). Bulletins et Memories de la Societe Medicale des Hopitaux de Paris 49, 1589 (1925).

U.S. Pat. No. 6,271,034.

U.S. Pat. No. 5,504,005.

There exists an urgent need for a novel tuberculosis (TB) vaccine as there are more than 8 million new cases of tuberculosis and more than 2 million deaths reported each year by the WHO (Dye et al., 1999). The discovery of the causative agent of TB, *Mycobacterium tuberculosis*, by Robert Koch in 1882 opened up the possibility for a novel vaccine (Koch, 1882). Since then, numerous attempts to develop attenuated vaccines against tuberculosis have failed, including tuberculin (a protein extract of killed *tubercle bacilli*) developed by Dr. Koch himself. This failure of tuberculin to protect led to a "firm conviction that immunity could only be established by inducing a definite, albeit limited, tuberculosis process" Grange et al., 1983). Thus, numerous labs set out to follow the example of Dr. Louis Pasteur for viruses and enrich attenuated mutants of the *tubercle bacillus* following repeated passaging.

In order to test the hypothesis that a *tubercle bacillus* isolated from cattle (now known as *M. bovis*) could transmit pulmonary tuberculosis following oral administration, Drs. Calmette and Guerin developed a medium containing beef bile that enabled the preparation of fine homogenous bacillary suspensions (Calmette and Guerin, 1905). An *M. bovis* strain obtained from Dr. Norcard, was passaged every 21 days in this medium and after the $39^{th}$ passage, the strain was found to be unable to kill experimental animal (Gheorghiu, 1996). "Between 1908 and 1921, the strain showed no reversion to virulence after 230 passages on bile potato medium" (Id.), which is consistent with the attenuating mutation being a deletion mutation. In the animal studies that followed, the strain ('BCG') was found to be attenuated but it also protected animals receiving a lethal challenge of virulent *tubercle bacilli* (Calmette and Guerin, 1920). BCG was first used as a vaccine against tuberculosis in 1921. From 1921 to 1927, BCG was shown to have protective efficacy against TB in a study on children (Weill-Halle and Turpin, 1925; Calmette and Plotz, 1929) and adopted by the League of Nations in 1928 for widespread use in the prevention of tuberculosis. By the 1950's after a series of clinical trials, the WHO was encouraging widespread use of BCG vaccine throughout the world (Fine and Rodrigues, 1990). Although an estimated 3 billion doses have been used to vaccinate the human population against tuberculosis, the mechanism that causes BCG's attenuation remains unknown.

Mahairas et al. (1996) first compared the genomic sequences of BCG and *M. bovis* using subtractive hybridization and found that there were three major deletions (named RD1, RD2, and RD3) present in the genome of *M. bovis*, but missing in BCG. Behr et al. (1999) and others (Gordon et al., 2001) later identified 16 large deletions, including RD1 to RD3, present in the BCG genome but absent in *M. tuberculosis*. These authors concluded that 11 of these 16 deletions were unique to *M. bovis*, while the remaining 5 deletions were unique to BCG. They also found that one of these 5 deletions, designated RD1 (9454 bp), is present in all of the BCG substrains currently used as TB vaccines worldwide and concluded that the deletion of RD1 appeared to have occurred very early during the development of BCG, probably prior to 1921 (Behr et al., 1999).

The development of insertional mutagenesis systems for BCG and *M. tuberculosis* (Kalpana et al., 1991), transposon mutagenesis systems (Cirillo et al., 1991; McAdam et al., 1995; Bardarov et al., 1997) and allelic exchange systems (Balasubramanian et al., 1996; Pelicic et al., 1997) led to the isolation of the first auxotrophic (nutrient-requiring) mutants of these slow-growing mycobacteria. Auxotrophic mutants of BCG and *M. tuberculosis* have been shown to confer protection to *M. tuberculosis* challenges with variable efficacies (Guleria et al., 1996; Smith et al., 2001). However, a head-to-head comparison of BCG to a leucine auxotroph of BCG showed that a single immunization elicited no positive skin-test and imparted little immunity to challenges with *M. tuberculosis* or *M. bovis* (Chambers et al., 2000). In contrast, a methionine auxotroph of BCG that grows in vivo did confer significant protection to challenge to both *M. tuberculosis* and *M. bovis* (Id.). A single dose of a leucine auxotroph of *M. tuberculosis* failed to elicit protection as good as BCG in BALB/c mice (Hondalus et al., 2000). These results suggest that optimal immunity against *M. tuberculosis* requires some growth of the immunizing strain. Double mutants of *M. tuberculosis* have also been created (Parish and Stoker, 2000), but whether such mutants are improved over single attenuating mutants in protecting mammals against challenge with a virulent *mycobacterium*, particularly when the host is immunocompromised, has not been established.

It is also worth noting that in the study of Chambers et al. (2000), both BCG and the BCG mutants seemed to protect better against *M. bovis* challenge than *M. tuberculosis*. If we assume the reverse correlate is true, we could hypothesize that optimal immunity against *M. tuberculosis* could be achieved with *M. tuberculosis*-derived mutant that grew in the mammalian host.

Based on the above, there remains a need for improved live mycobacterial vaccines having attenuated virulence, that confer protection from virulent mycobacteria, particularly *M. tuberculosis*. The instant invention satisfies that need.

SUMMARY OF THE INVENTION

The present invention is based on the discovery that deletion of the RD1 region or a region controlling the production of a vitamin from the genome of virulent mycobacteria in the *M. tuberculosis* complex attenuates the virulence of the mycobacteria without eliminating the ability of the mycobacteria to colonize susceptible mammals. These attenuated mycobacteria are capable of protecting the mammals from challenge by a virulent *M. tuberculosis* complex mycobacteria. The attenuated mycobacteria are thus useful in methods and compositions for vaccination of humans, cows and other mammals from virulent *M. tuberculosis* complex mycobacteria.

Accordingly, in some embodiments, the present invention is directed to a non-naturally occurring *Mycobacterium tuberculosis*. The *M. tuberculosis* comprises a deletion of an RD1 region or a region controlling production of a vitamin. The *M. tuberculosis* preferably exhibits attenuated virulence in a mammal when compared to the *M. tuberculosis* without the deletion.

In certain aspects of these embodiments, the *Mycobacterium tuberculosis* is produced by deletion of an RD1 region or a region controlling production of a vitamin. In these aspects, the *M. tuberculosis* also preferably exhibits attenuated virulence in a mammal when compared to the *M. tuberculosis* without the deletion.

In related embodiments, the present invention is also directed to mycobacteria in the *M. tuberculosis* complex that are genetically engineered to comprise a deletion of an RD1 region or a region controlling production of a vitamin.

The present invention is also directed to mycobacteria in the *M. tuberculosis* complex that comprise a deletion of a region controlling production of a vitamin. These mycobacteria are preferably capable of sustaining an infection in an immunocompetent mouse for at least 20 weeks.

The inventors have also discovered that mycobacteria that are auxotrophic for lysine have attenuated virulence and can protect a mammal against challenge by a virulent *mycobacterium*. Accordingly, the invention is also directed to non-naturally occurring mycobacteria in the *M. tuberculosis* complex, wherein the mycobacteria comprise a deletion of a region controlling production of lysine, and wherein the mycobacteria are capable of sustaining an infection in an immunocompetent mouse for at least 20 weeks.

The inventors have additionally discovered that mycobacteria having two attenuating deletions are highly attenuated, even in immunocompromised mammals, and are surprisingly effective in protecting mammals against challenge by a virulent microorganism. Thus, the invention is additionally directed to mycobacteria in the *M. tuberculosis* complex that are genetically engineered to comprise two deletions. The two deletions are any deletions where a virulent *mycobacterium* in the *M. tuberculosis* complex having either deletion exhibits attenuated virulence.

In further embodiments, the invention is directed to tuberculosis vaccines comprising any of the above-described *M. tuberculosis* or mycobacteria in the *M. tuberculosis* complex, in a pharmaceutically acceptable excipient. These vaccines are capable of protecting mammals from challenge by virulent mycobacteria in the *M. tuberculosis* complex.

The invention is also directed to methods of protecting mammals from virulent *M. tuberculosis* or mycobacteria in the *M. tuberculosis* complex. The methods comprise treating the mammal with any of the above vaccines.

In other embodiments, the invention is directed to methods of preparing tuberculosis vaccines. The methods comprise deleting an RD1 region or a region controlling production of a vitamin or lysine from an *M. tuberculosis* to produce any of the *M. tuberculosis* described above. In these embodiments, the vaccine is capable of protecting the mammal from challenge by a virulent *M. tuberculosis.*

In related embodiments, the invention is directed to other methods of preparing a tuberculosis vaccine. These methods comprise genetically engineering a *mycobacterium* to delete an RD1 region or a region controlling production of a vitamin or lysine to produce any of the mycobacteria described above. In these embodiments, the vaccine is capable of protecting the mammal from challenge by a virulent mycobacteria of the *M. tuberculosis* complex.

BRIEF DESCRIPTION OF THE DRAWINGS

FIG. 1 shows maps and autoradiographs pertaining to the construction of ΔRD1 mutants of *M. tuberculosis*. Panel a, *M. tuberculosis* H37Rv published sequence between 4346 kb and 4364 kb, showing predicted NcoI sites. Arrows on the top represent the genes in the RD1 region. The RD1 region deleted from *M. bovis* BCG is represented by an open bar spanning from Rv3871 to Rv3879c. Upstream and downstream flanking sequences, UFS and DFS respectively, are indicated as closed bars underneath the grid line. Panel b, Southern hybridization of *M. tuberculosis* H37Rv ΔRD1 created using two-step sequential homologous recombination. Panel c, Southern hybridization of *M. tuberculosis* H37Rv and Erdman ΔRD1 strains created using specialized transduction.

FIG. 2 shows graphs summarizing experiments establishing that *M. tuberculosis* H37Rv ΔRD1 is attenuated in SCID mice. Panel a, Seven female SCID mice were infected intravenously with $2\times10^6$ CFU *M. tuberculosis* H37Rv, *M. tuberculosis* H37Rv ΔRD1, and *M. tuberculosis* H37Rv ΔRD1::2F9 per mouse. The number of surviving mice was recorded post infection. Panel b, Mice were infected with different doses of *M. tuberculosis* H37Rv, *M. tuberculosis* H37Rv ΔRD1, and *M. bovis* BCG. For each strain, infection doses of $2\times10^6$ CFU, $2\times10^5$ CFU, $2\times10^4$ CFU, and $2\times10^3$ CFU per mouse, were administered via tail intravenous injection.

FIG. 3 is photographs, micrographs and autoradiographs showing that the *M. tuberculosis* H37Rv ΔRD1 mutant exhibits its two distinct colonial morphotypes. Panel a, *M. tuberculosis* H37Rv. Panel b, *M. tuberculosis* H37Rv ΔRD1. Panel c, *M. tuberculosis* H37Rv ΔRD1::2F9. Panel d, Southern analysis of *M. tuberculosis* H37Rv ΔRD1 NcoI-digested genomic DNA, isolated from three smooth and three rough colonies and probed with DFS. Panels e-g, Colonial morphotypes at higher magnification. e, Smooth morphotype at week 4. f, Rough morphotype at week 4. g, Rough morphotype at week 6.

FIG. 4 is graphs showing the growth kinetics of *M. tuberculosis* H37Rv ΔRD1 in BALB/c mice. Mice were infected with $2\times10^6$ CFU through tail injection. Time to death was noted and at day 1, week 4, 8, 14, and 22 post-infection, mice were sacrificed to determine the mycobacterial burden in the spleen, liver, and lung. The numbers represent the means of CFUs in organs derived from three animals. The error bars represent the standard errors of the means. Panel a, Time to death assay in BALB/c mice. Panel b, Spleen. Panel c, Liver. Panel d, Lung.

FIG. 5 is micrographs from pathological studies of infected BALB/c mice. Panels a-c, Lungs from mice infected with $2\times10^6$ CFU of *M. tuberculosis* H37Rv examined at 4, 8 and 14 weeks post-infection. The mild to moderate pneumonia at 4 and 8 weeks (a and b) progressed to severe consolidating granulomatous pneumonia at 14 weeks post infection (c). Panels d-f, Lungs from mice infected with $2\times10^6$ CFU of *M. tuberculosis* H37Rv ΔRD1 examined at 4, 8 and 22 weeks post-infection showing moderate pneumonia at 8 weeks post-infection (e) and persistent bronchitis and multifocal pneumonitis at 22 weeks post-infection (f). Panels (g)-(i), Mild lung lesions from mice infected with $2\times10^6$ CFU of BCG at 4, 8 and 22 weeks post-infection. Mild focal granulomas scattered widely in the lung at each time point with predominately lymphocytic accumulations in foci at 22 weeks post-infection.

FIG. 6 shows graphs summarizing experiments establishing that pantothenate auxotrophy leads to attenuation of *M. tuberculosis* ΔpanCD mutant in SCID mice. Panel A, Survival of BALB/c SCID mice (n=12 per group) infected intravenously with 490 CFU of H37Rv (○) or 210 CFU of panCD complementing strain (panCD in single copy integrated into the chromosome)(●) or $3.4\times10^5$ CFU of ΔpanCD mutant (▲) or $3.3\times10^5$ CFU of BCG-P (□). Panel B, Bacterial numbers in the spleen (●) and lungs (▲) of SCID mice infected intravenously with 490 CFU of H37Rv or numbers in spleen (○) and lungs (Δ) of mice infected with $3.4\times10^5$ CFU of ΔpanCD mutant. The results represent means± standard errors of four to five mice per group.

FIG. 7 shows graphs summarizing experiments demonstrating the attenuation, limited growth and persistence of ΔpanCD mutant in immunocompetent mice. Panel A, Survival of BALB/c mice (n=12 per group) infected with $4.4\times10^6$ CFU of wild-type *M. tuberculosis* H37Rv (○), $3.2\times10^6$ CFU panCD complementing strain (panCD in single copy integrated into the chromosome)(●) or $2.4\times10^6$ CFU panCD mutant (▲). Panels B and C, Bacterial loads in spleen and lungs of BALB/c mice infected intravenously with $4.4\times10^6$ CFU wild-type H37Rv (○) or $3.2\times10^6$ CFU panCD complementing strain (●) or $2.4\times10^6$ CFU ΔpanCD mutant (▲). CFUs were assayed at various time points on 7H11 agar with or without pantothenate supplementation where required. The results represent means± standard errors of four to five mice per group.

FIG. 8 shows graphs summarizing experiments demonstrating the attenuation, limited replication and persistence of ΔnadBC mutant in immunocompetent mice. Panels A and B, Bacterial loads in lungs and spleen of C57BL/6 mice infected with wild type *M. tuberculosis* H37Rv (●) or ΔnadBC mutant (○). Mice were infected intravenously with $10^6$ CFU of each strain. CFUs were assayed at various time points on 7H11 agar with or without nicotinamide supplementation where required. The results represent means± standard errors of four to five mice per group. Panel C, Survival of C57BL/6 mice (n=12 per group) infected with $10^6$ CFU of wild-type bacteria (●) or $10^6$ CFU of ΔnadBC mutant (○).

FIG. 9 shows an illustration, map and autoradiograph relating to the pathway for the biosynthesis of pantothenic acid and coenzyme A and its disruption in *M. tuberculosis*. Panel a. The enzymes involved in the biosynthesis of pantothenic acid and having annotation in the genomic sequence of *M. tuberculosis* H37Rv are shown in bold numbers: 1) panB, ketopantoate hydroxymethyl transferase; 2) panD, aspartate-1-decarboxylase; 3) panC, pantothenate synthetase; 4) panK, pantothenate kinase; 5) acpS, ACP synthase. Panel b. Map of the panCD genomic region in the wild type *M. tuberculosis* H37Rv and the ΔpanCD mutant. Restriction sites and probe location are indicated. Panel c. Southern blot of BssHII-digested genomic DNA from wild-type H37Rv (lane 1), two independent clones of ΔpanCD mutant from H37Rv (lanes 2 & 3) and probed with a 716 bp downstream region flanking the panCD operon. Molecular size marker (in kb) is shown on the left.

FIG. 10 shows graphs summarizing experiments demonstrating that pantothenate auxotrophy leads to attenuation of ΔpanCD mutant in mice. a. Survival of BALB/c SCID mice (n=12 per group) infected intravenously with H37Rv (○) or panCD-complemented strain (●) or ΔpanCD mutant (▲) or *M. bovis* BCG-P (□). b. Bacterial numbers in the spleen (○), liver (□) and lung (Δ) of SCID mice infected intravenously with H37Rv or the bacterial numbers in the spleen (●), liver (■) and lung (▲) of mice infected with ΔpanCD mutant. c. Survival of immunocompetent BALB/c mice (n=16 per group) infected with H37Rv (○) or panCD-complemented strain (●) or ΔpanCD mutant (▲). d, e, f. Bacterial numbers in lung (d), spleen (e) and liver (f) of immunocompetent BALB/c mice infected intravenously with either H37Rv (○), panCD-complemented strain (●) or ΔpanCD mutant (▲). Data are means± standard errors of four to five mice per group.

FIG. 11 shows micrographs (Panels a-d) and graphs (Panels e and f) summarizing experiments demonstrating that the ΔpanCD mutant produces less tissue pathology in lungs of infected BALB/c mice and protects mice against challenge with virulent *M. tuberculosis*. Panel a. Severe consolidating granulomatous pneumonia (★) obliterating the normal lung parenchyma at 3 weeks post-infection with H37Rv. Panel b. Severe consolidating granulomatous pneumonia (★) obliterating the normal lung parenchyma at 3 weeks post-infection with the panCD-complemented strain, similar to the wild type strain. Panel c. Mild lung infection caused by the ΔpanCD mutant at 3 weeks post-infection. Localized multifocal granulomas (arrows) scattered widely in the lung. Most of the lung is normal alveolar spaces and airways. Panel d. Lung of mouse infected with ΔpanCD mutant examined histologically at 23 weeks post-infection. Occasional focal, mild perivascular and interstitial infiltrations composed of predominately lymphocytes (arrows). Most of the lung is normal alveolar spaces and airways. e, f. The attenuated ΔpanCD mutant protects mice against aerogenic challenge with virulent *M. tuberculosis* Erdman. Subcutaneously immunized mice were challenged after 90 days through the aerosol route. The CFU numbers reflect the bacterial burden at 28 days post aerosol challenge in the lung (e) and spleen (f). Naive mice—black fill; mice infected with 1 dose panCD—light shade; mice infected with 2 doses panCD—dark shade; mice infected with BCG-P—unshaded.

FIG. 12 shows autoradiographs of Southern analysis of the NcoI-digested genomic DNA isolated from the wild type and the ΔRD1 mutants generated using specialized transduction in *M. tuberculosis* and *M. bovis*. Lanes: 1—*M. tuberculosis* H37Rv; 2—*M. tuberculosis* H37Rv ΔRD1; 3—*M. tuberculosis* Erdman; 4—*M. tuberculosis* Erdman ΔRD1; 5—*M. tuberculosis* CDC1551; 6—*M. tuberculosis* CDC1551 ΔRD1; 7—*M. bovis* Ravenel; and 8—*M. bovis* Ravenel ΔRD1. The probes used in the Southern analysis was either DFS (left) or IS6110-specific sequence (right).

FIG. 13 shows graphs summarizing data confirming that deletion of RD1 in *M. tuberculosis* and *M. bovis* confers an attenuation of virulence for *M. tuberculosis* and *M. bovis*, as indicated by these Time to death curves of mice infected intravenously with $2\times10^6$ CFU mycobacteria. Panel A, SCID mice infected with *M. tuberculosis* H37Rv (■), *M. tuberculosis* H37Rv ΔRD1 (□), *M. tuberculosis* Erdman (●), *M. tuberculosis* Erdman ΔRD1 (○), *M. tuberculosis* CDC1551 (▲), *M. tuberculosis* CDC1551 ΔRD1 (Δ), *M. bovis* Ravenel (▼), *M. bovis* Ravenel ΔRD1 (∇); Panel B, SCID mice infected intravenously with *M. tuberculosis* H37Rv (●), *M. tuberculosis* ΔRD1 (■), *M. tuberculosis* ΔRD1::2F9 (▲), *M. bovis* Ravenel (○), *M. bovis* Ravenel ΔRD1 (□), and *M. bovis* BCG (Δ); Panel C, BALB/c mice were infected with *M. tuberculosis* H37Rv (○), *M. tuberculosis* ΔRD1 (Δ), and *M. bovis* BCG (□).

FIG. 14 are graphs summarizing experiments demonstrating the clearance of the lysine auxotroph in SCID mice. The viable bacterial counts are shown for the spleens, livers, and lungs of SCID mice injected intravenously with the lysine auxotroph strain and the prototrophic control strain. Three mice were assayed at each time point. The error bars indicate the standard deviations of the mean values. Note that the counts at time zero are the counts obtained at 24 hours post-injection, as described in Example 5. Panels A, B and C show the log of the viable bacteria in each organ after injection with $1\times10^7$ CFU of the $Lys^-$ *M. tuberculosis* mutant $mc^23026$ (□), or $1\times10^7$ CFU of the complemented $Lys^+$ *M. tuberculosis* strain $mc^23026$/pYUB651 (■).

FIG. 15 is graphs summarizing experimental results of experiments that establish the vaccine efficacy of the *M. tuberculosis* lysine auxotroph $mc^23026$. C57B1/6 mice were injected intravenously with $1\times10^6$ CFU of the *M. tuberculosis* lysine auxotroph $mc^23026$, followed by one or two additional injections at 4 week intervals. Five mice were sacrificed weekly after each immunization and the viable bacteria counts of the auxotroph determined in the lungs and spleens. Control mice were given a similar amount of BCG-Pasteur or only PBST. Shown in Panel A is the clearance of the auxotroph from the lungs of the mice after each immunization period; one injection (■), two injections (♦), and three injections (●). Three months after the initial immunization the vaccinated and control mice were challenged with virulent *M. tuberculosis* Erdman by the aerosol route. Five challenge mice were sacrificed following the challenge period and the lung homogenates plated to check the viable counts of the challenge inoculum. Groups of vaccinated and control mice were sacrificed at 14, 28, and 42 days later and the lung and spleen homogenates plated to determine viable colony forming units. Shown in Panel B are the viable challenge bacteria per lung of mice given one dose of the *M. tuberculosis* lysine auxotroph, and in panel C, the viable challenge bacteria per lung of mice given two doses of the auxotroph. Key: Viable challenge bacteria per lung of mice given the *M. tuberculosis* lysine auxotroph $mc^23026$ (■), BCG-Pasteur (◇), or PBST (○). P values are indicated in the figure. Note that the results shown here are for the lungs. Similar results (not shown) were obtained from the spleens in all the experiments.

FIG. 16 shows a graph summarizing experiments establishing the survival curves of mice immunized three times with the *M. tuberculosis* lysine auxotroph mc$^2$3026. C57Bl/6 mice were injected intravenously with 1×10$^6$ CFU of the *M. tuberculosis* lysine auxotroph mc$^2$3026, followed by two more injections at 4 week intervals, and challenged as described in Example 5. The percent survival is shown for mice immunized thrice with the *M. tuberculosis* lysine auxotroph mc$^2$3026 (■, 5 mice total), once with BCG-Pasteur (♦, 5 mice), and for the PBST controls (●, 10 mice).

Figure 19:
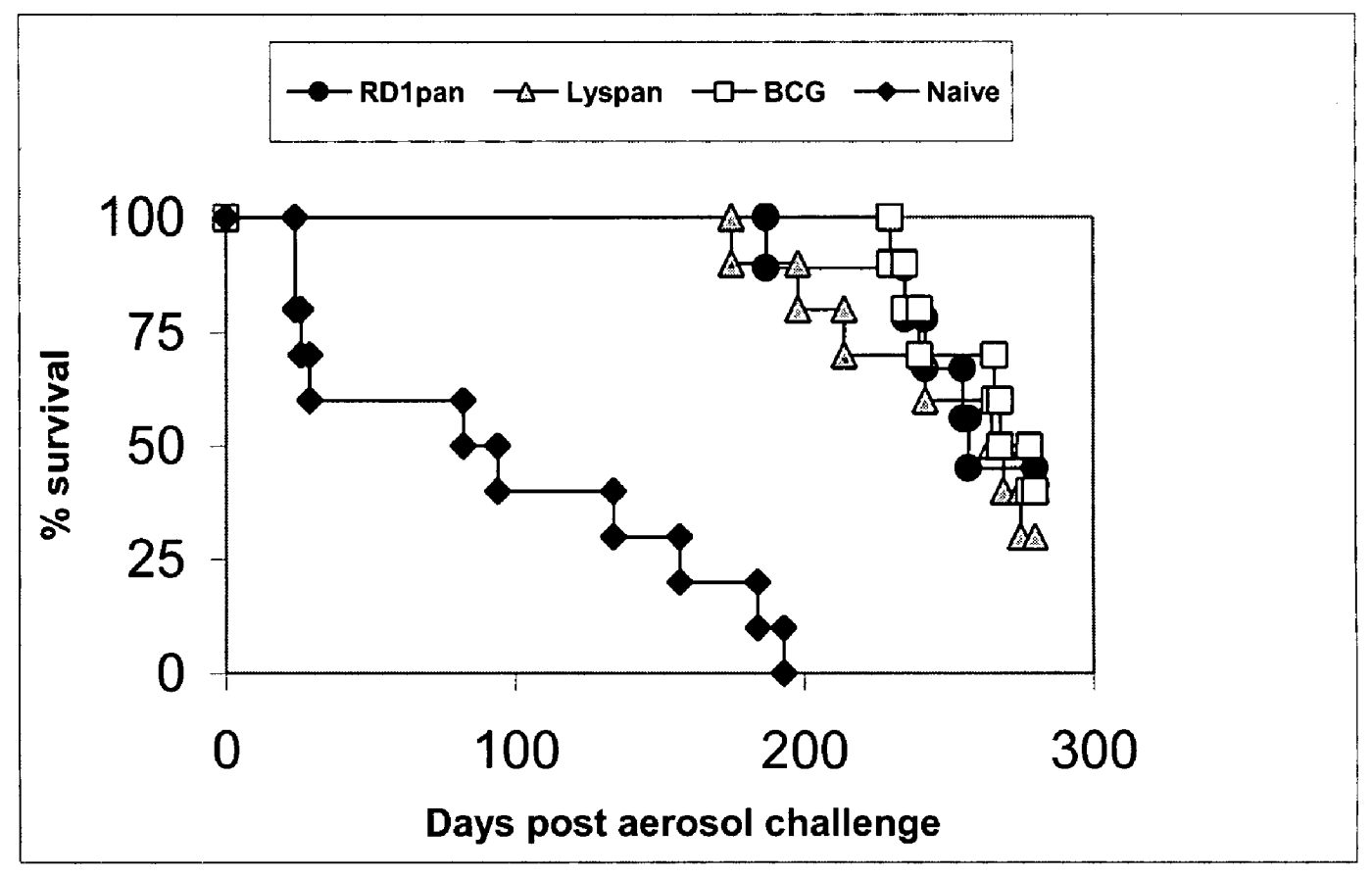

FIG. 19 is a graph summarizing experimental results establishing that immunization with mc$^2$6020 and mc$^2$6030 protects mice against TB as effectively as BCG. This graph shows the survival of C57Bl/6 mice challenged with virulent *M. tuberculosis* Erdman through the aerosol route three months after a single dose subcutaneous immunization with either BCG, mc$^2$6020 (ΔlysAΔpanCD) or mc$^2$6030 (ΔRD1ΔpanCD) and compared to non-immunized naive mice. There were 12 to 15 mice in each survival group.

Figure 20:
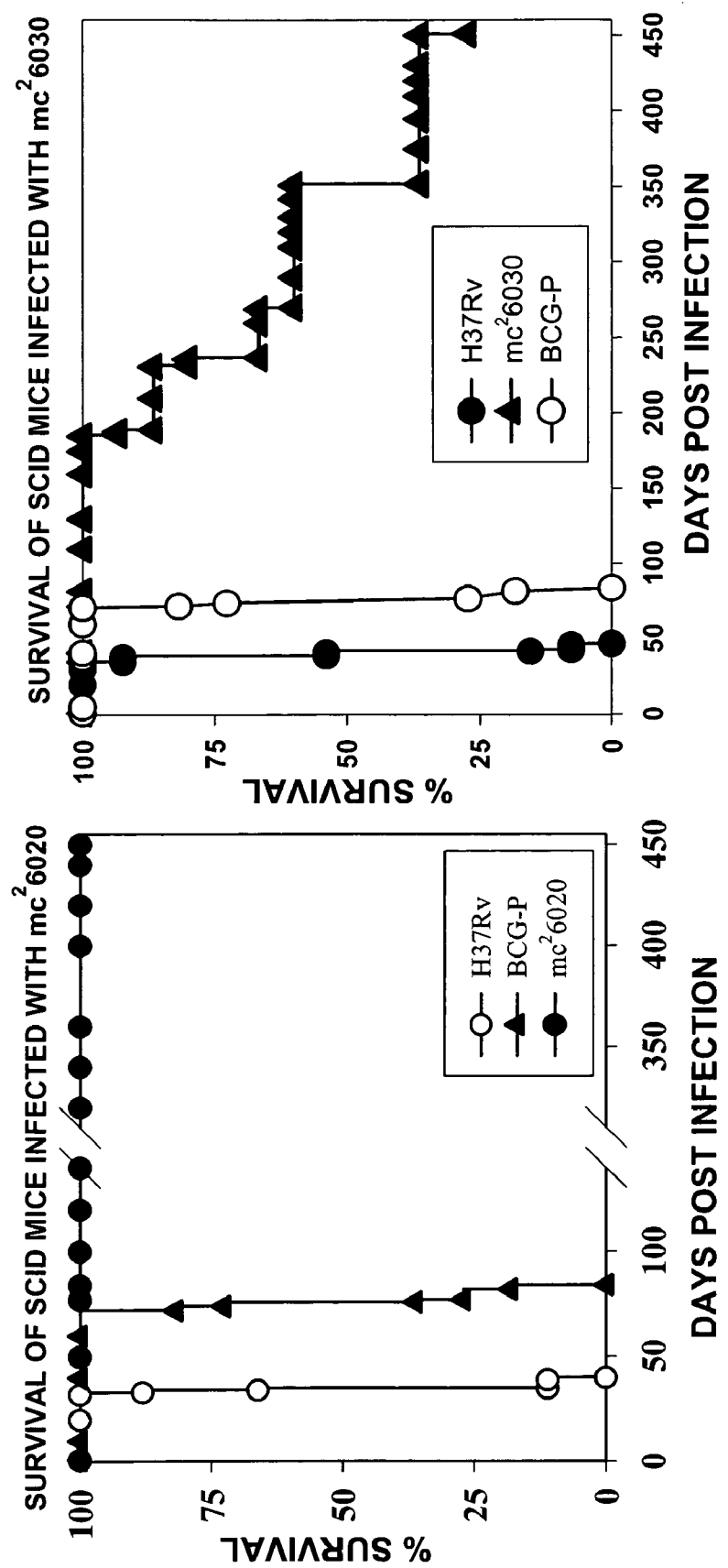

FIG. 20 shows graphs summarizing experimental results establishing that *M. tuberculosis* double deletion mutants are highly attenuated in SCID mice. A dose of 10$^5$ mc$^2$6020 or mc$^2$6030 were intravenously inoculated into SCID mice (10 per group) and time to death assessments were performed. While the same dose of *M. tuberculosis* and BCG killed mice in 40 or 90 days, respectively, the mice infected with mc$^2$6020 or mc$^2$6030 survived over 400 or 250 days, respectively.

DETAILED DESCRIPTION OF THE INVENTION

The present invention is based in part on the discovery that virulent mycobacteria in the *M. tuberculosis* complex that have deletions in the RD1 region, or in a region that controls production of a vitamin, are attenuated in virulence but are capable of sustaining viability and growth in a mammalian host, and are also capable of protecting against a challenge by a virulent *M. tuberculosis* complex *mycobacterium*.

Thus, in some embodiments, the invention is directed to non-naturally occurring *Mycobacterium tuberculosis* that comprise a deletion of an RD1 region or a region controlling production of a vitamin. These *M. tuberculosis* preferably exhibit attenuated virulence in a mammal when compared to the *M. tuberculosis* without the deletion.

A host organism can be inoculated with the mycobacteria of the present invention by any of a number of ways known in the art. These include oral ingestion, gastric intubation, or broncho-nasal-ocular spraying. Other methods of administration include intravenous, intramuscular, intramammary, or, preferably, subcutaneous or intradermal injection. The immunization dosages required can be determined without undue experimentation. One or two dosages of avirulent mycobacteria at 1-2×10$^6$ colony forming units (CFU) have previously been used, but other dosages are contemplated within the scope of the invention. Multiple dosages can be used as needed to provide the desired level of protection from challenge.

It is well known in the art that in order to elicit an immune response with a live vaccine such as an avirulent mycobacteria, it is preferred that the vaccine organism can sustain an infection in the immunized host, to provide a sustained exposure of the host's immune system to the organism. Therefore, in various preferred embodiments, the *M. tuberculosis* of the invention are capable of sustaining an infection in the host. The ability to sustain infection can be measured without undue experimentation by any of a number of ways described in the art. With the mycobacteria of the present invention, a preferred way of measuring sustained infection is by determining whether viable mycobacteria of the inoculated strain will remain resident in an immunocompetent mouse (e.g., BALB/c or C57BL/6 strain) for more than four weeks. More preferably, the inoculated mycobacteria will remain resident in the mouse for at least ten weeks. In the most preferred embodiments, viable mycobacteria of the inoculated strain will remain resident in the mouse for at least 20 weeks.

Preferably, the attenuated mycobacteria of the invention are capable of protecting a mammal from challenge by a virulent *M. tuberculosis* complex mycobacteria. This ability can be determined by any of a number of ways provided in the literature. A preferred method is aerogenically treating an immunocompetent mouse with the virulent mycobacteria, as described in Examples 1 and 2. Aerogenic challenge is preferred because that most closely mimics natural infection. The skilled artisan would understand that the ability of an avirulent *mycobacterium* to protect a mouse from challenge from a virulent *mycobacterium* is indicative of the ability of the avirulent *mycobacterium* to protect a human, including a human child, from tuberculosis infection. A more stringent test of an avirulent *mycobacterium* to prevent infection by a virulent challenge is to use an immunocompromised mammal such as a SCID mouse.

The deletion of the RD1 region or the region controlling production of a vitamin is contemplated in these embodiments with any *M. tuberculosis* strain. Preferably, the strain is a virulent strain, since those strains would be most likely to sustain an infection after the deletion is made. Preferred *M. tuberculosis* strains are the H37Rv and CDC1551 strain, because the genetics of those strains are very well known.

In some aspects of these embodiments, the deletion is of the RD1 region (see Example 1). Strains with these deletions can be determined by any means in the art, preferably by molecular genetic means, for example by hybridization methods (e.g., Southern blot using a probe from the RD1 region) or by amplification methods (e.g., PCR using primers to amplify a portion of the RD1 region). An example of an *M. tuberculosis* RD1 region (from H37Rv) is provided herein as SEQ ID NO:1. The skilled artisan could identify analogous RD1 regions from other *M. tuberculosis* complex mycobacteria without undue experimentation. Those RD1 regions would be expected to have strong homology to SEQ ID NO:1, at least 80% homologous to SEQ ID NO:1. However, it is to be understood that virulent *M. tuberculosis* can be rendered avirulent by deletions in a portion of the RD1 region. Therefore, non-naturally occurring *M. tuberculosis* that have a partial deletion in the RD1 region are envisioned as within the scope of the invention, provided the deletion can cause a virulent *M. tuberculosis* to become avirulent. It is expected that such *M. tuberculosis* with partial RD1 deletions can still sustain an infection in a mammal and protect against challenge by a virulent *M. tuberculosis*.

In embodiments where the deletion is in a region controlling production of a vitamin, the deletion can be in any genetic element leading to loss of production of the vitamin, including structural genes for enzymes involved in the biosynthesis of the vitamin, and genetic control elements such as promoters, enhancers, etc.

Deletion of a region controlling production of any essential vitamin or their precursors is contemplated as within the scope of the invention. As used herein, an essential vitamin is defined by its normal usage, that is, a small molecular weight compound that is required as a cofactor for the efficient function of an essential enzyme or enzymes. Nonlimiting examples include vitamin A, thiamin (B1), riboflavin (B2), nicotinic acid (niacin)/nicotinamide/nicotinamide adenine dinucleotide (NAD)/nicotinamide adenine dinucleotide phosphate (NADP/coenzyme II), pantothenate (pantothenic acid/B5), pyridoxine (B6), folic acid, B12, biotin, C, D, E and K. Preferred vitamin targets for deletion include nicotinamide and pantothenate (see Example 2). Methods for determining whether a *mycobacterium* has deletions leading to the loss of production of any of these vitamins are within the scope of the art.

Deletions leading to the loss of any of these vitamins would be expected to lead to attenuated virulence of an otherwise virulent *mycobacterium* in the *M. tuberculosis* complex. Any of those strains would also be expected to sustain an infection in a mammal.

Preferred vitamin targets are pantothenate and nicotinamide adenine dinucleotide (NAD) (see Example 2). A preferred pantothenate deletion is of structural genes in the pantothenate biosynthetic operon, most preferably the panC and panD genes, the combined mutation being ΔpanCD. An example of a deletion of those genes is the deletion of the sequence from *M. tuberculosis* H37Rv provided herein as SEQ ID NO:2. Similarly, a preferred NAD deletion is in the structural genes of the NAD biosynthetic operon, most preferably the nad B and C genes, the combined mutation being ΔnadBC. An example of a deletion in those genes is the deletion of the sequence from *M. tuberculosis* H37Rv provided herein as SEQ ID NO:3.

In similar embodiments, the invention is directed to any of the above-described *M. tuberculosis* that are produced by deleting an RD1 region or a region controlling production of a vitamin. The deletion can be made by serial in vitro passage of a virulent *M. tuberculosis* (as the well-known *M. bovis* BCG was made) and selection for the desired deletion. More preferably, however, the deletion is made by genetic engineering, since such genetic methods allow precise control of the deletion being made.

Various methods of making deletions in mycobacteria are known in the art. Nonlimiting examples include specialized transduction (see, e.g., U.S. Pat. No. 6,271,034, Example 1 and Example 2), and sequential two-step recombination (see Example 1). The latter method can usefully employ a sacB selective marker (Example 1).

Since, in preferred embodiments of the invention, the mycobacteria exhibit attenuated virulence and can sustain an infection in a mammal, these mycobacteria can usefully further employ a foreign DNA stably integrated into the genome of the mycobacteria, such that the mycobacteria can express a gene product coded by the foreign DNA. See, e.g., U.S. Pat. No. 5,504,005.

Thus, it is apparent that the present invention has wide applicability to the development of effective recombinant vaccines against bacterial, fungal, parasite or viral disease agents in which local immunity is important and might be a first line of defense. Non-limiting examples are recombinant vaccines for the control of bubonic plague caused by *Yersinia pestis*, of gonorrhea caused by *Neisseria gonorrhoea*, of syphilis caused by *Treponema pallidum*, and of venereal diseases or eye infections caused by *Chlamydia trachomatis*. Species of *Streptococcus* from both group A and group B, such as those species that cause sore throat or heart disease, *Neisseria meningitidis, Mycoplasma pneumoniae, Haemophilus influenzae, Bordetella pertussis, Mycobacterium leprae, Streptococcus pneumoniae, Brucella abortus, Vibrio cholerae,* Shigella spp., *Legionella pneumophila, Borrelia burgdorferi, Rickettsia* spp., *Pseudomonas aeruginosa,* and pathogenic *E. coli* such as ETEC, EPEC, UTEC, EHEC, and EIEC strains are additional examples of microbes within the scope of this invention from which foreign genes could be obtained for insertion into mycobacteria of the invention. Recombinant anti-viral vaccines, such as those produced against influenza viruses, are also encompassed by this invention. Recombinant anti-viral vaccines can also be produced against viruses, including RNA viruses such as Picornaviridae, Caliciviridae, Togaviridae, Flaviviridae, Coronaviridae, Rhabdoviridae, Filoviridae, Paramyxoviridae, Orthomyxoviridae, Bunyaviridae, Arenaviridae, Reoviridae or Retroviridae; or DNA viruses such as Hepadnaviridae, Paroviridae, Papovaviridae, Adenoviridae, Herpesviridae or Poxyiridae.

Recombinant vaccines to protect against infection by pathogenic fungi, protozoa or parasites are also contemplated by this invention.

The avirulent microbes of the present invention are also contemplated for use to deliver and produce foreign genes that encode pharmacologically active products that might stimulate or suppress various physiological functions (i.e., growth rate, blood pressure, etc.). In such microbes, the recombinant gene encodes said pharmacologically active products.

By immunogenic agent is meant an agent used to stimulate the immune system of an individual, so that one or more functions of the immune system are increased and directed towards the immunogenic agent. Immunogenic agents include vaccines.

An antigen or immunogen is intended to mean a molecule containing one or more epitopes that can stimulate a host immune system to make a secretory, humoral and/or cellular immune response specific to that antigen.

In preferred embodiments, the foreign DNA encodes an antigen, an enzyme, a lymphokine, an immunopotentiator, or a reporter molecule. Preferred examples include antigens from *Mycobacterium leprae, Mycobacterium tuberculosis,* malaria sporozoites, malaria merozoites, diphtheria toxoid, tetanus toxoids, *Leishmania* spp., *Salmonella* spp., *Mycobacterium africanum, Mycobacterium intracellulare, Mycobacterium avium, Treponema* spp., Pertussis, Herpes virus, Measles virus, Mumps virus, *Shigella* spp., *Neisseria* spp., *Borrelia* spp., rabies, polio virus, human immunodeficiency virus, snake venom, insect venom, and *Vibrio cholera*; steroid enzymes; interleukins 1 through 7; tumor necrosis factor α and β; interferon α, β, and γ; and reporter molecules luciferase, β-galactosidase, β-glucuronidase and catechol dehydrogenase.

The scope of the present invention includes novel mycobacteria in the *M. tuberculosis* complex that are genetically engineered to comprise a deletion of an RD1 region or a region controlling production of a vitamin. The scope of the deletions and the characteristics of these mycobacteria are as with the *M. tuberculosis* mycobacteria described above. These mycobacteria include any in the *M. tuberculosis* complex, including *M. africanum, M. bovis* including the BCG strain and the subspecies caprae, *M. canettii, M. microti, M. tuberculosis* and any other mycobacteria within the *M. tuberculosis* complex, now known or later discovered. Preferred species are *M. bovis,* including the BCG strain, and *M. tuberculosis,* since those species are the most important as causes of mammalian diseases, such as tuberculosis in humans and *M. bovis* infection in cows.

Also included as within the scope of the invention is any non-naturally occurring *mycobacterium* in the *M. tuberculosis* complex having a deletion of a region controlling production of a vitamin. These mycobacteria preferably are capable of sustaining an infection in a mammal. The scope of the deletions and the characteristics of these mycobacteria are as with the *M. tuberculosis* and other mycobacteria described above.

The inventors have also discovered that mycobacteria in the *M. tuberculosis* complex that are auxotrophic for lysine have attenuated virulence and protect a mammal from challenge by a virulent *mycobacterium*. See Example 5. Thus, in some embodiments, the invention is directed to non-naturally occurring mycobacteria in the *M. tuberculosis* complex that comprise a deletion of a region controlling production of lysine. These mycobacteria are capable of sustaining an infection in an immunocompetent mouse for at least 20 weeks. As with previously described embodiments, these mycobacteria can be any species in the *M. tuberculosis* complex. However, due to their importance as disease organisms, it is preferred mycobacteria are *M. tuberculosis* and *M. bovis*, e.g., *M. bovis* BCG.

These mycobacteria would also be expected to exhibit attenuated virulence in a mammal when compared to the mycobacteria without the deletion. Additionally, they would be expected to provide protection to a mammal from challenge by a virulent *mycobacterium* in the *M. tuberculosis* complex. A preferred deletion is a ΔlysA deletion, for example as provided herein as SEQ ID NO:4.

When constructing a live vaccine that is an attenuated pathogen due to a deletion, it is often desirable to include a second deletion, to better assure the safety of the vaccine. Second deletions in any of the above-described mycobacteria are thus contemplated as within the scope of the invention. The second deletion preferably can also attenuate virulence of an otherwise virulent *mycobacterium* in the *M. tuberculosis* complex. This second deletion can be the RD1 region if the first deletion is not. The second deletion can also be a deletion that would cause a prototrophic *mycobacterium* to be auxotrophic, or any other deletion that could improve the safety or efficacy of the *mycobacterium* in protecting against infection. Nonlimiting examples include deletions in a gene or genes controlling production of an amino acid or a nucleotide, or a vitamin not eliminated by the first mutation.

The inventors have also discovered that two attenuating deletions in a *mycobacterium* in the *M. tuberculosis* complex provides a high level of protection to a mammal from challenge by a virulent *mycobacterium*. See Example 6.

Thus, in some embodiments, the invention is directed to mycobacteria in the *M. tuberculosis* complex which are genetically engineered to comprise two deletions. Preferably, each of the two deletions are capable of individually attenuating virulence when engineered into a virulent *mycobacterium* in the *M. tuberculosis* complex.

Preferred embodiments of these mycobacteria are as with the other mycobacteria of the invention, e.g., the *mycobacterium* is preferably a *Mycobacterium tuberculosis*; the *mycobacterium* is preferably capable of sustaining an infection in an immunocompetent mouse for at least 20 weeks; and the *mycobacterium* is capable of protecting the mammal from challenge by a virulent *mycobacterium*.

As with the other mycobacteria previously described, the two attenuating deletions can be any deletions that are individually capable of attenuating virulence of an otherwise virulent strain. Preferred deletions are deletions of an RD1 region (e.g., a deletion of SEQ ID NO:1), deletions of a region controlling production of a vitamin, or deletions of a region controlling the production of an amino acid, as previously discussed. A preferred deletion of a region controlling production of a vitamin is the ΔpanCD deletion, e.g., as disclosed in Examples 2 and 3, discussing attenuated strains having a deletion of SEQ ID NO:2. Preferred deletions of regions controlling production of amino acids are those regions controlling production of proline, tryptophan, leucine or lysine. See, also, Examples 5 and 6, describing strains having a ΔlysA deletion (SEQ ID NO:4), or two mutations including one with a ΔlysA deletion.

In additional embodiments, the invention is directed to tuberculosis vaccines made using any of the above described mycobacteria, in a pharmaceutically acceptable excipient. These vaccines are capable of protecting the mammal from challenge by a virulent *M. tuberculosis* complex mycobacteria. In some preferred embodiments, the *mycobacterium* is a *Mycobacterium bovis* and the mammal is a cow; in other preferred embodiments, the *mycobacterium* is *M. tuberculosis* and the mammal is a human, e.g., a human child.

By vaccine is meant an agent used to stimulate the immune system of an individual so that protection is provided against an antigen not recognized as a self-antigen by the immune system. Immunization refers to the process of inducing a continuing high level of antibody and/or cellular immune response in which T-lymphocytes can either kill the pathogen and/or activate other cells (e.g., phagocytes) to do so in an individual, which is directed against a pathogen or antigen to which the organism has been previously exposed. The phrase "immune system" refers herein to the anatomical features and mechanisms by which a mammal produces antibodies against an antigenic material which invades the cells of the individual or the extra-cellular fluid of the individual and is also intended to include cellular immune responses. In the case of antibody production, the antibody so produced can belong to any of the immunological classes, such as immunoglobulins, A, D, E, G or M. Immune responses to antigens are well studied and widely reported. A survey of immunology is provided in Elgert (1996) and Stites et al. (1991).

The pharmaceutical carrier or excipient in which the vaccine is suspended or dissolved may be any solvent or solid or encapsulating material. The carrier is non-toxic to the inoculated individual and compatible with the microorganism or antigenic gene product. Suitable pharmaceutical carriers are known in the art and, for example, include liquid carriers, such as normal saline and other non-toxic salts at or near physiological concentrations, and solid carriers, such as talc or sucrose. Gelatin capsules can serve as carriers for lyophilized vaccines. Adjuvants may be added to enhance the antigenicity if desired. When used for administering via the bronchial tubes, the vaccine is preferably presented in the form of an aerosol. Suitable pharmaceutical carriers and adjuvants and the preparation of dosage forms are described in, for example, Gennaro (1985).

Similarly, the invention is directed to methods of protecting a mammal from a virulent *mycobacterium* in the *M. tuberculosis* complex. The methods comprise treating the mammal with any of the above-described vaccines.

The vaccines can be administered by oral ingestion, gastric intubation, or broncho-nasal-ocular spraying, intravenous, intramuscular, intramammary, or, preferably, by subcutaneous or intradermal injection. The immunization dosages required can be determined without undue experimentation. One or two dosages of avirulent mycobacteria at $1$-$2 \times 10^6$ colony forming units (CFU) have previously been used, but other dosages are contemplated within the scope of the invention. Multiple dosages can be used as needed to provide the desired level of protection from challenge (see, e.g., Example 5).

The present invention is also directed to methods of preparing a tuberculosis vaccine. The methods comprise deleting an RD1 region or a region controlling production of a vitamin from a *mycobacterium* in the *M. tuberculosis* complex to produce any of the mycobacteria previously described.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1989); "Current Protocols in Molecular Biology" Volumes I-IV (Ausubel, R. M., ed. (1997); and "Cell Biology: A Laboratory Handbook" Volumes I-III (J. E. Celis, ed. (1994).

EXAMPLE 1

*Mycobacterium Tuberculosis* Having an RD1 Deletion has Attenuated Virulence and Protects Against Tuberculosis This example describes experimental methods and results that establish that deleting the RD1 region from a virulent *M. tuberculosis* attenuates the virulence of the *M. tuberculosis* in both immunocompetent and immunocompromised mice, and protects against subsequent challenge by a virulent *M. tuberculosis*.

Materials and Methods

Media and Cultures. The mycobacterial strains *M. tuberculosis* H37Rv, *M. tuberculosis* Erdman and *M. bovis* BCG Pasteur were obtained from the Trudeau Culture Collection (Saranac Lake, N.Y.). They were cultured in Middlebrook 7H9 broth and 7H10 agar supplemented with 10% OADC, 0.5% glycerol, and 0.05% Tween 80. Cyclohexamide, which does not affect mycobacterial growth, was added to the 7H10 agar medium at 0.1% to avoid fungal contamination. To examine the colony morphology of mycobacteria, Tween 80 was not added to 7H10 agar medium. The acriflavin resistant strain (Hepper and Collins, 1984) of *M. tuberculosis* Erdman grew in the presence of 20 µg of acriflavin per ml of medium.

DNA manipulation and construction of *M tuberculosis* ΔRD1. The following four primers were used to amplify upstream and downstream flanking sequences (UFS and DFS, respectively) for the construction of the RD1 deletion mutants. UFS was amplified using TH201: GGGGGCGCACCTCAAACC (SEQ ID NO:5) and TH202: ATGTGCCAATCGTCGACCAGAA (SEQ ID NO:6). DFS was amplified using TH203: CACCCAGCCGCCCGGAT (SEQ ID NO:7), and TH204: TTCCTGATGCCGCCGTCTGA (SEQ ID NO:8). Recognition sequences for different restriction enzymes were included at the ends of each primer to enable easier manipulation.

The unmarked deletion mutant of *M. tuberculosis* H37Rv, mc$^2$4004, was generated by transformation (Snapper et al., 1988) using a sacB counterselection (Pelocic et al., 1996; Pavelka and Jacobs, 1999). Specifically, the plasmid pJH508 was created by first cloning UFS into KpnI and XbaI sites, then cloning DFS into EcoRI and HindIII sites of pJH12, a pMV261-derived *E coli*-Mycobacteria shuttle plasmid, to create pJH506 in which UFS and DFS flanked a green fluorescent protein gene (GFPuv, Clonetech) whose expression was driven by the *M. leprae* promoter 18Kd. The UFS-gfp-DFS cassette was sub-cloned into the EcoRV site of plasmid pYUB657 to create pJH508. The first homologous recombination involved the identification of hygromycin resistant colonies, resulting from the transformation of *M. tuberculosis* with pJH508. Southern analysis of the NcoI digested DNA isolated from hygromycin resistant colonies probed with UFS or DFS, confirmed the presence of a single copy of pJH508 inserted into the *M. tuberculosis* genome. The transformant identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

Specialized transduction (Bardarov and Jacobs, 1999), a mycobacteriophage-based method for the delivery of homologous DNA constructs using conditionally replicating shuttle phasmids (Jacobs et al, 1987; Bardarov and Jacobs, 1999; Carriere et al., 1997), has been used successfully for *M. tuberculosis* (Glickman et al., 2000; Glickman et al., 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature sensitive mycobacteriophage derived from TM4. The transduction was performed by growing *M. tuberculosis* to an O.D.$_{600}$ of 0.8, washing twice with MP buffer, re-suspending into an equal volume of MP buffer and mixing with the transducing phage phAEKO1 at an MOI of 10. The mixtures were incubated at 37° C. overnight, then plated on 7H10 plates supplemented with hygromycin at 50 µg/ml. Hygromycin resistant colonies were analyzed by PCR and Southern hybridization, as described above, to confirm the deletion of RD1.

Complemetation analyses was performed using the integration proficient cosmids (Pascopella et al., 1994; Lee et al., 1991) pYUB412 made by S. Bardarov, a library made by F. Bange, and cosmid identified and generously provided by S. T. Cole.

Results

Figure 1:
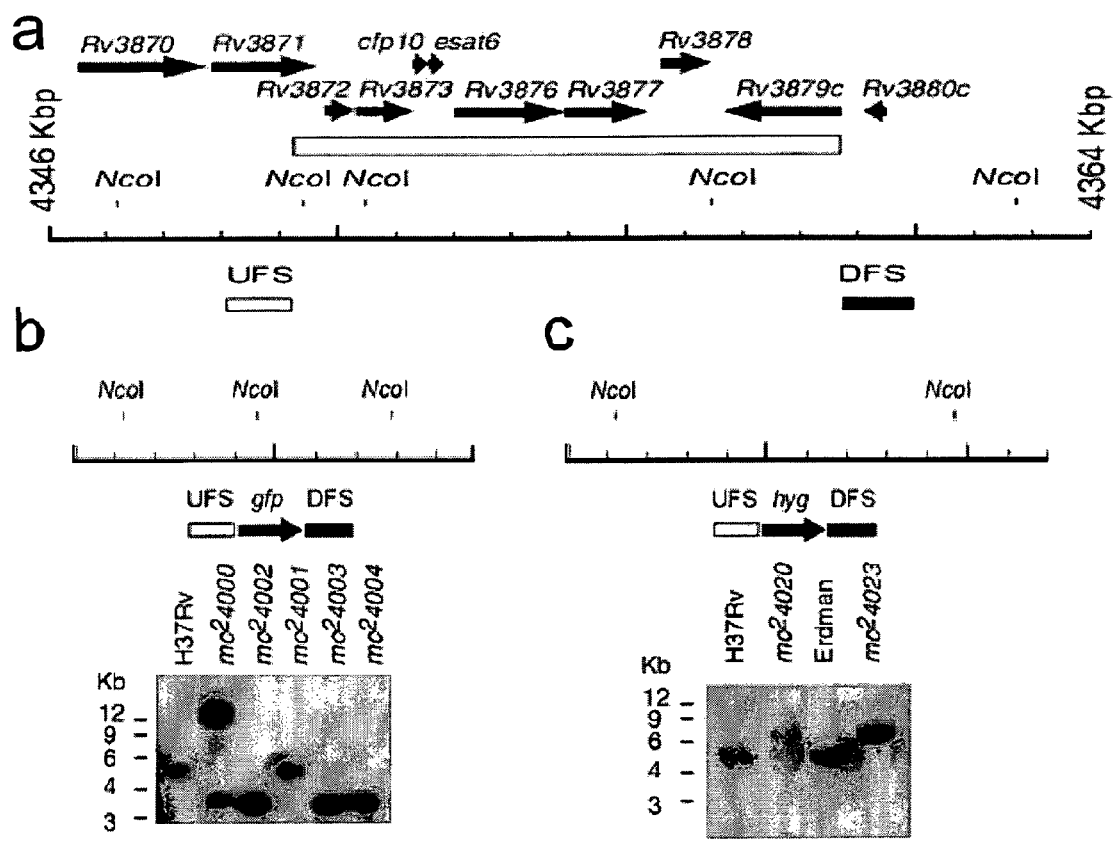

Genetic engineering of *M. tuberculosis* mutants with RD1 deletions. The RD1 (region of difference) region has been defined as the specific 9454 bp of DNA that is present in virulent *M. tuberculosis* and *M. bovis*, but absent in BCG (Mahairas et al., 1996). The annotation of RD1 predicts that the deletion would disrupt 9 genes encoding ORF's (Id.; Cole et al., 1998). Five of the 9 ORF's have no known functions (Rv3871, Rv3876, Rv3877, Rv3878 and Rv3879c), two genes encode members of the PE/PPE family (Rv3872/Rv3873), and two genes encode the secreted proteins Cfp10 (Berhet et al., 1998) and Esat6 (Andersen et al., 1991) (Rv3875) (FIG. 1). To test if the RD1 region is essential for virulence in *M. tuberculosis*, it was necessary to 1) delete the RD1 region from virulent *M. tuberculosis* strains, 2) demonstrate loss of virulence and 3) restore virulence by complementation with the RD1 DNA. The RD1 deletion (ΔRD1) was successfully introduced into *M. tuberculosis* by two different techniques, utilizing both a plasmid that allows two-step sequential recombination to make an unmarked deletion, and specialized transduction (FIG. 1a-c). For both methods, the same 1200 bp on each side of the RD1 deletion were cloned into the appropriate plasmid or phage vector and then introduced into *M. tuberculosis* H37Rv by transformation or phage infection. An unmarked RD1 deletion mutant of *M. tuberculosis* H37Rv, mc$^2$4004, was constructed, purified, and has the advantage that additional mutations can be readily added to it. In addition, the RD1 deletion was successfully engineered in the H37Rv and Erdman strains of *M. tuberculosis* using a specialized transducing phage. Since TM4 phages have been shown to infect over 500 clinical *M. tuberculosis* isolates (Jacobs et al., 1987), it should be possible to introduce the RD1 deletion into any *M. tuberculosis* isolate of interest.

Figure 2A:
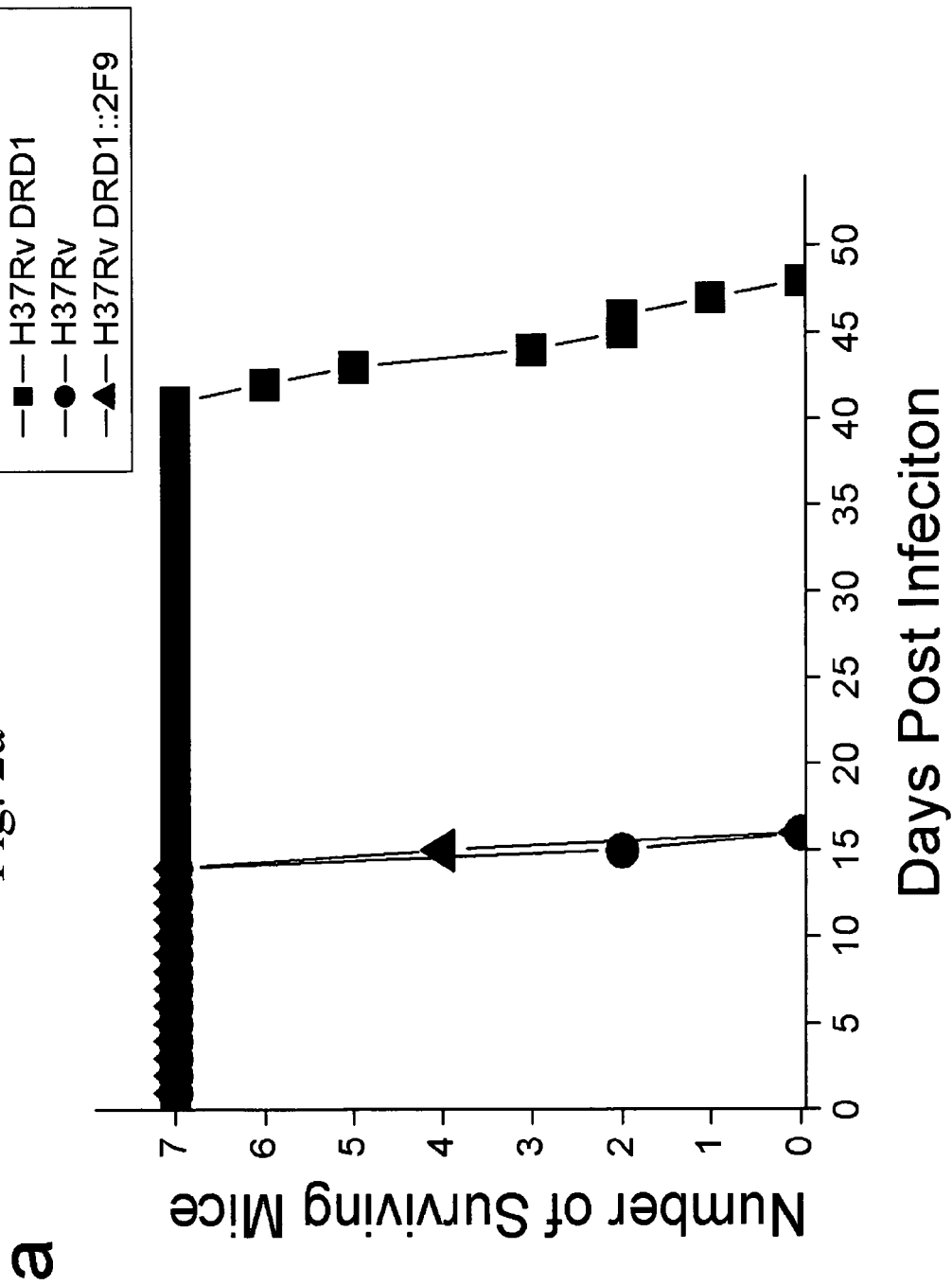

*M. tuberculosis* H37Rv ΔRD1 is attenuated for virulence. To test if the RD1 deletion causes an attenuating phenotype in *M. tuberculosis*, the *M. tuberculosis* H37Rv ΔRD1 (mc$^2$4004) was introduced into immunocompromised mice possessing the SCID (severe combined immunodeficiency) mutation. Groups of ten mice were injected intravenously with either 2×10$^6$ *M. tuberculosis* H37Rv or *M. tuberculosis* H37Rv ΔRD1 and three mice per group were sacrificed 24 hours later to verify the inoculation doses. All of the SCID mice infected with the parental *M. tuberculosis* H37Rv strain died within 14 to 17 days post infection (FIG. 2a). In contrast, the SCID mice infected with the same dose of *M. tuberculosis* H37Rv ΔRD1 were all alive at 35 days post-infection demonstrating a marked attenuation of the strain. To prove that the attenuation was due to the RD1 deletion, mc$^2$4004 was transformed with an integrating plasmid containing the RD1 region from *M. tuberculosis* H37Rv. SCID mice injected intravenously with 2×10$^6$ of the transformed strain died 13 to 16 days post-infection (FIG. 2a), thereby, establishing that the genes in the RD1 deletion complemented the attenuating phenotype.

Figure 2B:
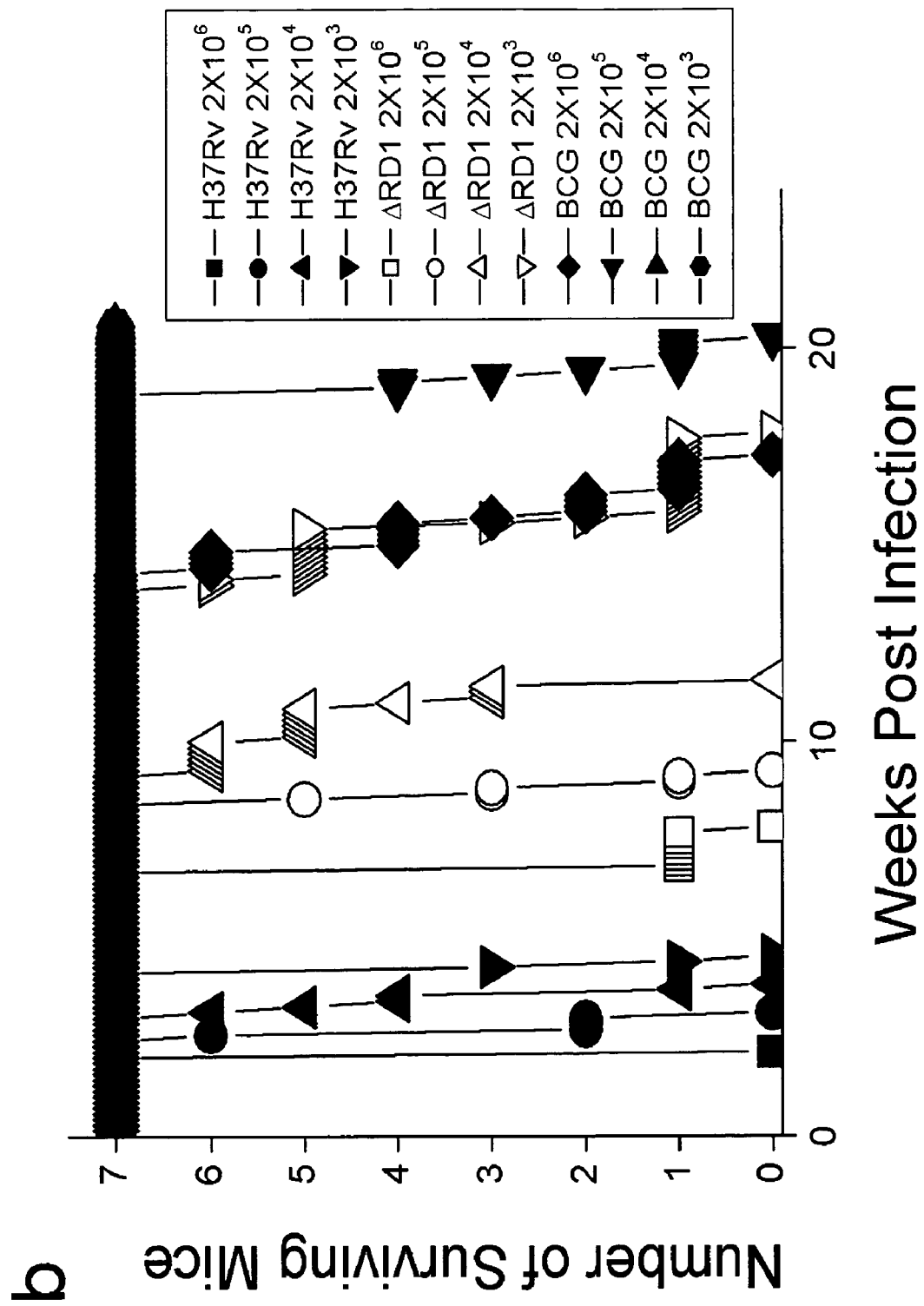

To further characterize the attenuating phenotype of the RD1 deletion in mc$^2$4004, we compared the virulence of *M. tuberculosis* H37Rv and BCG-Pasteur to *M. tuberculosis* H37Rv ΔRD1 with time-to-death experiments in SCID mice following injections with 10-fold varying inocula. Groups of 10 mice were injected intravenously, each mouse receiving from 2×10$^3$ to 2×10$^6$ CFU. FIG. 2b shows that the SCID mice succumbed to the infection with all three mycobacterial strains. However, the SCID mice succumbed to an *M. tuberculosis* H37Rv intravenous infection within 2 to 5 weeks, in a dose dependent manner. In the same time frame, the SCID mice did not succumb to infection with *M. tuberculosis* H37Rv ΔRD1 until week 7, and only then, with the high dose of 2×10$^6$ CFU. Mice receiving 2×10$^3$ CFU *M. tuberculosis* H37Rv ΔRD1 survived longer than 14 weeks post infection, the survival rate of which coincided with the mice receiving 2×10$^6$ CFU of *M. bovis* BCG. Thus, these experiments established that *M. tuberculosis* H37Rv ΔRD1 was significantly more attenuated than its parent, but not as attenuated as BCG-Pasteur in the immunocompromised mice.

Figure 3:
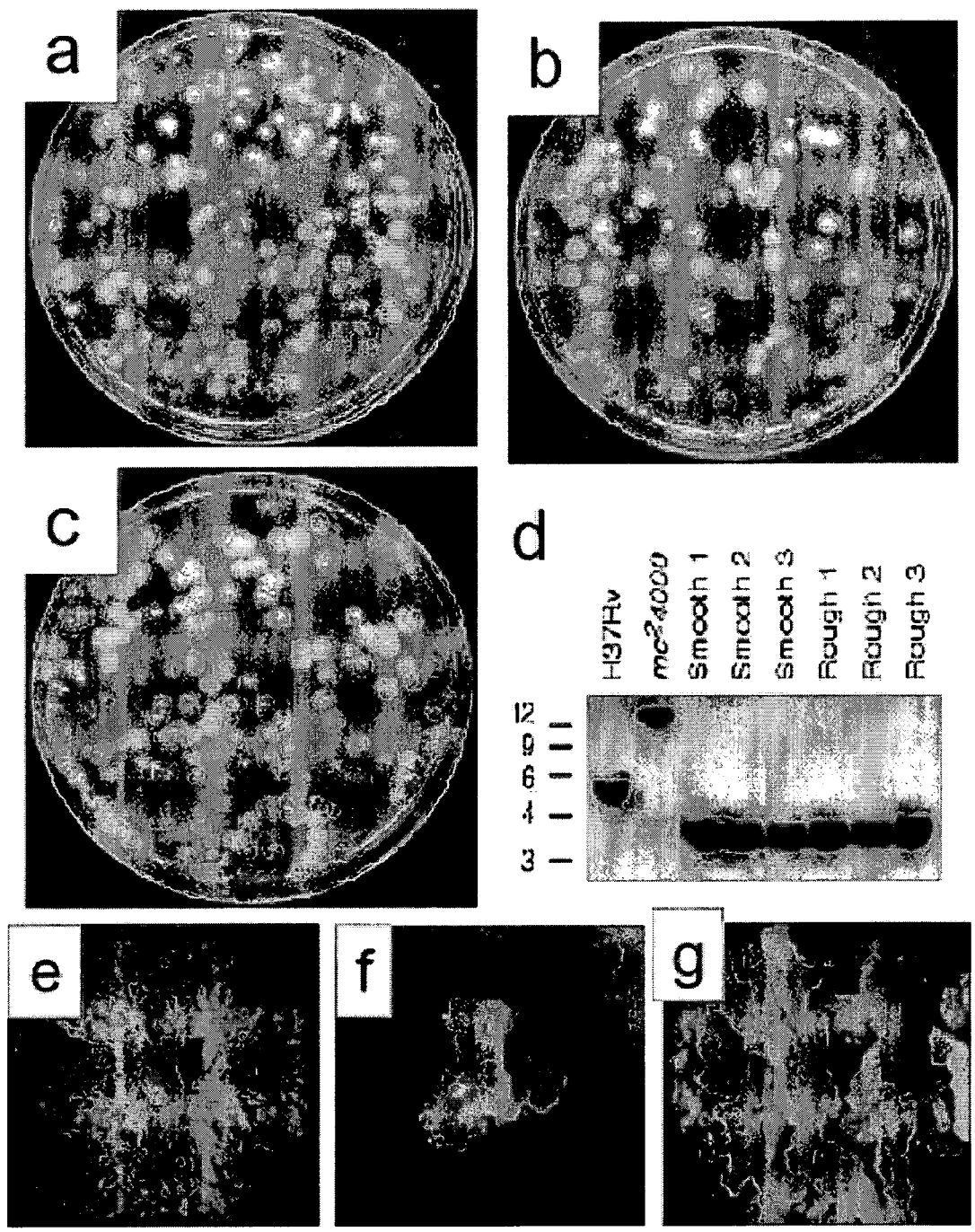

Colonial morphotypes of *M. tuberculosis* H37Rv ΔRD1. The *M. tuberculosis* H37Rv ΔRD1 mutant was generated independently three times from the single crossover construct (mc$^2$4000) and upon subculturing, consistently yielded a 20 to 50% mixture of two colonial morphotypes on Middlebrook medium without Tween 80 (FIG. 3a). One morphotype was a smooth (S) phenotype that was flat and corded (like the parental *M. tuberculosis* H37Rv strain) and the second was a rough and raised (R) phenotype. Repeated subculturing of either the R or S colonies continued to yield both colonial morphotypes, but with a distribution of approximately 80% smooth and 20% rough colonies. The distinction of these two types of morphology could be noted even when the colonies were less than two weeks old as the rough colonies were constricted and elevated with only a small portion of the base of the colony attached to the agar, while the smooth colonies tends to be flattened and spread out. When colonies grew older, e.g. 6 weeks old, the rough colonies remained more constricted compared to those of smooth colonies. The rough colonies exhibited large folds on the surface (FIG. 3f, g), as compared to those of the smooth colonies that exhibited small wrinkles (FIG. 3e).

Interestingly, in 1929, Petroff et al. reported a similar property for an early-derived BCG strain (Petroff et al., 1929) and proposed that the attenuation phenotype of BCG was not stable. Calmette disputed that the avirulent phenotype reverted and postulated that Petroff et al. had acquired a contaminating virulent strain. Southern analysis of R and S colonies revealed each morphotype has the same RD1-deleted genotype (FIG. 3d). Furthermore, complementation of *M. tuberculosis* H37Rv ΔRD1 with the RD1 region restored the mutant phenotype back to the homogenous parental S phenotype (FIG. 3a-c). These results suggest that the variable morphotypes resulted directly from the RD1 deletion thus dissociating a direct correlation of virulence with morphotype.

Figure 4:
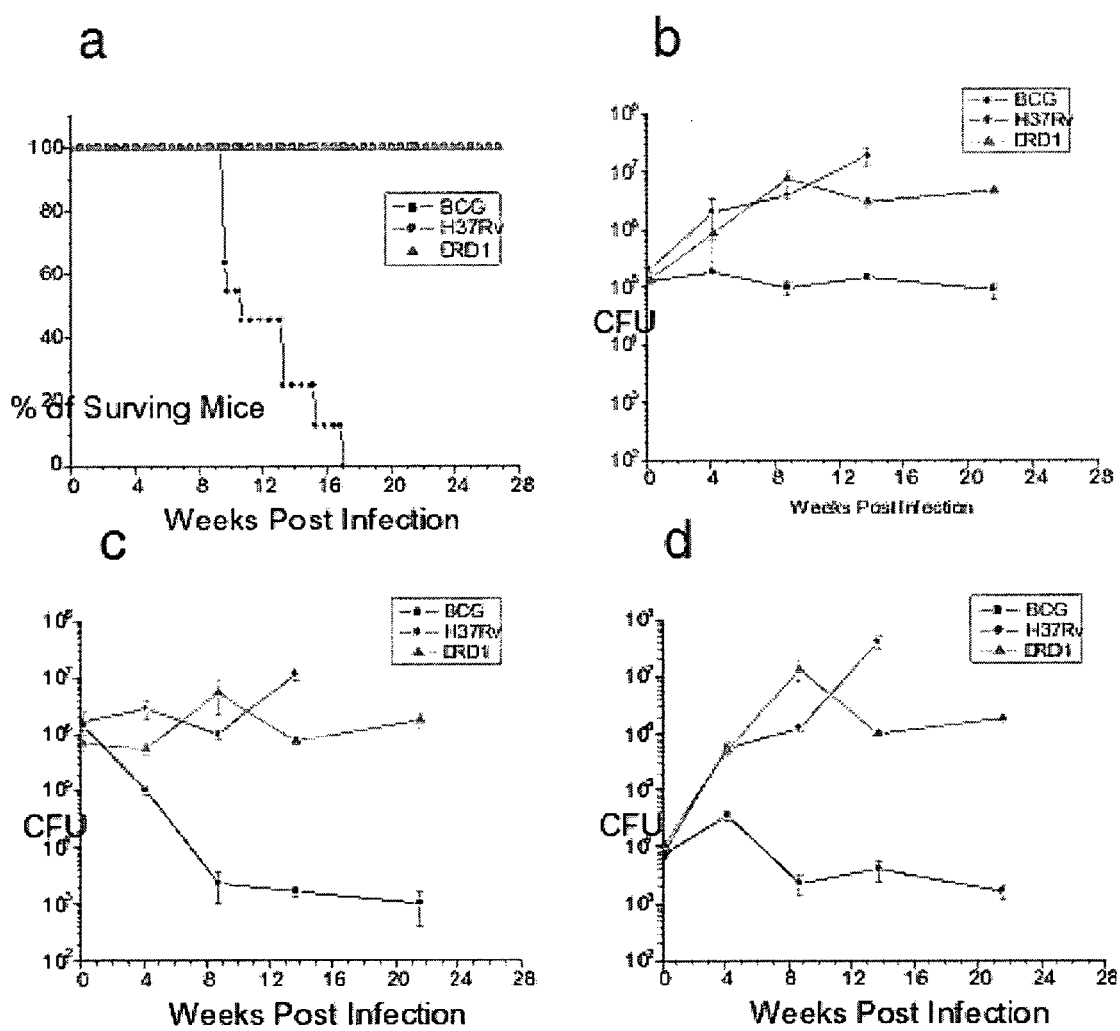

The *M. tuberculosis* H37Rv ΔRD1 is highly attenuated in immunocompetent BALB/c mice. To further assess the pathogenicity, survival, growth kinetics, and the histopathological analysis of the *M. tuberculosis* H37Rv ΔRD1 mutant, we compared the parental *M. tuberculosis* H37Rv to BCG-Pasteur strains in BALB/c mice. In survival studies, greater than 50% BALB/c mice had died at 14 weeks post i.v. infection with 2×10$^6$ CFUs of *M. tuberculoisis* H37Rv strain (FIG. 4a). In contrast, all mice infected with a similar dose of either BCG or *M. tuberculosis* H37Rv ΔRD1 survived for longer than 22 weeks. These results were substantiated in a separate experiment in which a group of 11 BALB/c mice were infected with 1×10$^5$ CFU of *M. tuberculosis* H37Rv ΔRD1 and 9 of 11 mice (81%) survived greater than 9 months post-infection (data not shown). While BCG and *M. tuberculosis* H37Rv ΔRD1 showed similar survival results, the growth relative kinetics in mouse organs differed substantially. BCG grew in a limited fashion in lungs, liver and spleen in BALB/c mice and was cleared to undetectable levels by week 12 (FIG. 4b-d). In contrast, the *M. tuberculosis* H37Rv ΔRD1 strain grew in a fashion indistinguishable from the parental *M. tuberculosis* H37Rv in all mouse organs for the first 8 weeks. Thereafter, mice infected with the parental *M. tuberculosis* failed to contain the infection leading to mortality. Strikingly, mice infected with the *M. tuberculosis* H37Rv ΔRD1 showed a definite control over infection resulting in significantly prolonged survival of mice (FIG. 4b-d).

Figure 5:
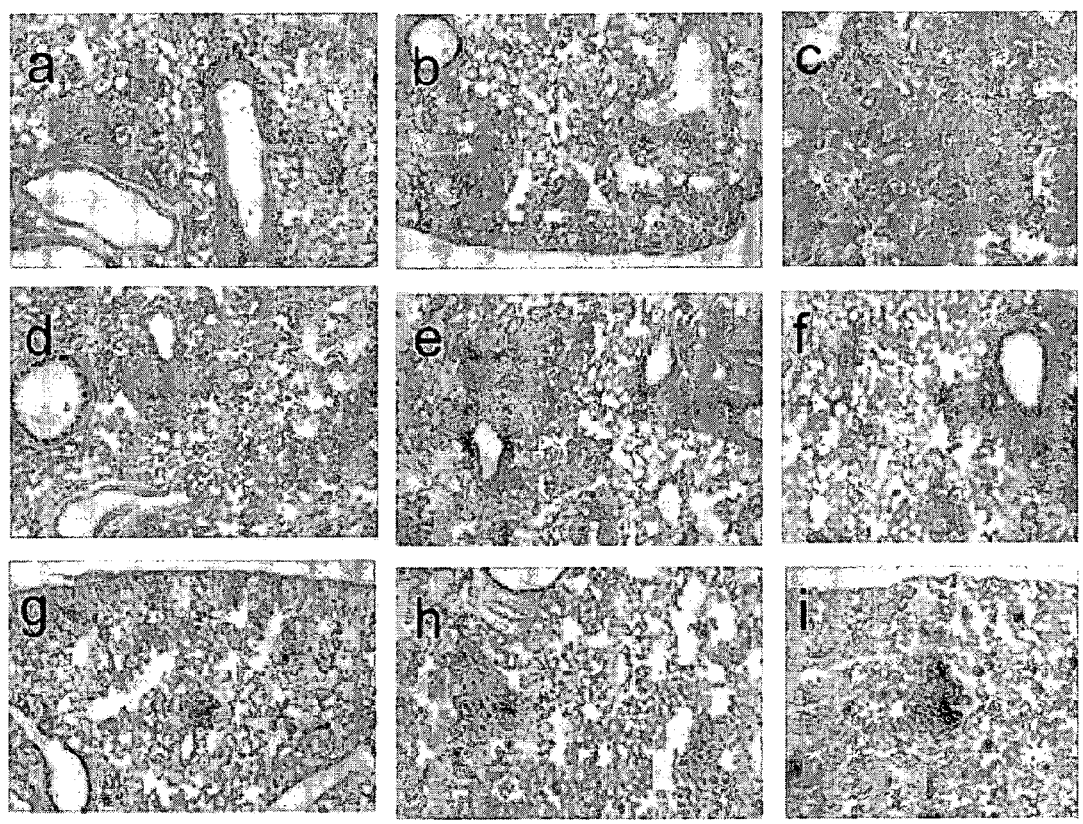

The differing survival data of the three strains was clearly substantiated by histopathological analysis. *M. tuberculosis* H37Rv ΔRD1 caused less severe organ damage in the lung, liver and spleen than the highly virulent parent strain *M. tuberculosis* H37Rv. *M. bovis* BCG was the least virulent of the three strains. Based on histopathological evaluation, the mortality in mice infected with the wild type *M. tuberculosis* H37Rv (documented above and in FIG. 4a) was caused by worsening pneumonia, hepatitis and splenitis (FIG. 5a-c). Mice examined at 14 weeks post-infection had developed severe lobar granulomatous pneumonia. Acid fast staining demonstrated large numbers of *M. tuberculosis* H37Rv, often in clumps, throughout the lung. The livers and spleens showed a severe diffuse granulomatous inflammation.

Histopathological examination further demonstrated that *M. tuberculosis* H37Rv ΔRD1 was attenuated in virulence compared to the parent strain *M. tuberculosis* H37Rv (FIG. 5*d-f*). In contrast to the rapidly progressive infection with the parent strain *M. tuberculosis* H37Rv, the lung lesions caused by *M. tuberculosis* H37Rv ΔRD1 were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again at 22 weeks post-infection, the lungs showed peribronchial and perivascular inflammatory cell accumulations and focal, generally non-confluent, granulomas now with a prominent lymphocytic infiltration. The numbers of acid fast organisms were reduced. Liver lesions consisted of low numbers of scattered granulomas. Spleens were smaller, with persistent granulomas in the red pulp.

Mice infected with *M. bovis* BCG showed mild lesions in the lung, liver and spleen at all time points (FIG. 5*g-i*). At longer time intervals post-infection the lesions were fewer in number, smaller with prominent lymphocytic infiltrations. At 14 weeks post-infection, *M. bovis* BCG was below the level of detection by acid fast staining. In summary, whereas *M. tuberculosis* H37Rv ΔRD1 initially grew in a manner similar to the parental *M. tuberculosis* H37Rv, this RD1 mutant was limited in the extent of spread of infection, particularly in the lung. This contrasted to the extensive and severe damage caused by the parent strain. The subsequent resolving granulomas, localization of the lesions and changes in the composition of the inflammatory cell infiltrations suggested that the mice mounted an effective immune response to combat *M. tuberculosis* H37Rv ΔRD1 infection and thereby reduced the numbers of viable organisms.

*M. tuberculosis* H37Rv ΔRD1 protects mice against aerosolized *M. tuberculosis* challenge. To test the potential of *M. tuberculosis* H37Rv ΔRD1 to immunize mice and protect against tuberculous challenge, we used the model of subcutaneous immunization followed by aerosol challenge with virulent *M. tuberculosis*. Our initial studies in C57BL/6 mice monitored the growth the *M. tuberculosis* H37Rv ΔRD1 strain over an 84-day period. Groups of mice (5 mice per group) were vaccinated subcutaneously (sc) either once or twice, 6 weeks apart, with $10^6$ CFU *M. tuberculosis* H37Rv ΔRD1 organisms. Additional mice were infected intravenously (iv) with the same dose of the RD1-deleted strain in order to examine the pathogenicity in C57BL/6 mice.

As seen in Table 1, *M. tuberculosis* H37Rv ΔRD1 persisted in the lungs, liver, and spleen for 3 months at moderate levels of infection but the organisms failed to grow substantially in the lungs and spleens of mice that had been inoculated iv. In contrast, reduced persistence and decreased concentrations of *M. tuberculosis* H37Rv ΔRD1 organisms were detected in organ homogenates prepared from mice that had been vaccinated sc. For the groups of mice that had been immunized with only one dose sc., low levels of *M. tuberculosis* H37Rv ΔRD1 *bacilli* were recovered from the spleen after 28 and 56 days post-vaccination; however, no splenic mycobacteria were detected 84 days after the sc. injection. Importantly, the concentration of *M. tuberculosis* H37Rv ΔRD1 organisms in the lungs after the sc. immunizations was below the threshold of detection (<100 CFUs per organ) for the CFU assay at nearly all time points during the three month study.

TABLE 1

Growth kinetics in C57BL/6 mice.

| | Lung (Log CFU) | | | Spleen (Log CFU) | | |
|---|---|---|---|---|---|---|
| Weeks | i.v. | s.c. | s.c. (2×) | i.v. | s.c. | s.c. (2×) |
| 4 | 5.86 ± 0.10 | <2 | not done | 5.73 ± 0.05 | 2.41 ± 0.26 | not done |
| 8 | 5.79 ± 0.07 | <2 | 2.52 ± 0.34 | 5.37 ± 0.04 | 3.12 ± 0.40 | 3.62 ± 0.29 |
| 12 | 5.61 ± 0.09 | <2 | <2 | 5.40 ± 0.05 | <2 | 3.52 ± 0.22 |

Mice were infected with $10^6$ *M. tuberculosis* H73Rv ΔRD1 by different routes.
The data are presented as mean ± standard error of the mean.

Three months after the Sc. vaccinations with the ΔRD1 strain, groups of mice were challenged aerogenically with a low dose (50 CFUs) of an acriflavin-resistant strain of *M. tuberculosis* Erdman. The use of a drug-resistant challenge strain permitted the differentiation of the challenge organisms from the sensitive vaccine population. As controls, other groups of mice were immunized Sc. with $10^6$ CFUs of BCG Pasteur. The protective responses induced by the *M. tuberculosis* H37Rv ΔRD1 vaccination were evaluated by assessing the relative growth of the acriflavin-resistant challenge organisms in naive, BCG vaccinated, and *M. tuberculosis* H37Rv ΔRD1 immunized mice and by comparing the relative post-challenge lung pathology in the experimental groups and the naive controls. As seen in Table 2, the growth of the drug-resistant challenge organisms was substantially lower in the lungs of animals vaccinated with BCG or the *M. tuberculosis* H37Rv ΔRD1 vaccine. Significant reductions in the lung CFU values in the vaccinated animals (relative to naive controls) could be detected both 28 and 56 days after the challenge. Dissemination to the spleen was also significantly limited in all of the vaccination groups with the most substantial differences (−1.4 $\log_{10}$ CFUs compared to the naives) being detected during the first month post-challenge. While significant differences in the growth of the mycobacterial challenge was identified between unvaccinated and vaccinated mice, the rate of proliferation of the acriflavin-resistant challenge strain in all the experimental groups (BCG sc or *M. tuberculosis* H37Rv ΔRD1 or 2 doses sc) was nearly identical and not statistically different.

TABLE 2

*M. tuberculosis* ΔRD1 and BCG protect C57BL/6 mice from areosol challenge with *M. tuberculosis* Erdman

| | Lung (Log CFU) | | Spleen (Log CFU) | |
|---|---|---|---|---|
| | Day 28 | Day 56 | Day 28 | Day 56 |
| Naive | 4.77 ± 0.06 | 4.11 ± 0.05 | 3.57 ± 0.21 | 3.20 ± 0.16 |
| BCG (1×) | 3.96 ± 0.20 | 3.80 ± 0.08 | 2.18 ± 0.18 | 2.48 ± 0.23 |
| ΔRD1 (1×) | 3.97 ± 0.39 | 3.71 ± 0.06 | 2.12 ± 0.12 | 2.60 ± 0.25 |
| ΔRD1 (2×) | 3.96 ± 0.15 | 3.66 ± 0.09 | 2.21 ± 0.15 | 2.22 ± 0.16 |

Immunizations were performed subcutaneously once (1×) or twice (2×) with 2 × $10^6$ CFUs of the vaccinating strains. Three months later, vaccinated animals were aerogenically challenged with 50 CFUs/mouse of acriflavin resistant *M. tuberculosis* Erdman. The growth of the bacterial challenge was monitored 28 and 56 days post infection by plating on Middlebrook 7H11 plates containing 20 μg/ml acriflavin and using procedures previously described (Delogu et al., 2002).

Discussion

The *M. tuberculosis* H37Rv ΔRD1 mutant strain shares significant properties with BCG including: 1) a significant attenuation of virulence in mice, 2) the ability to generate variable colonial morphotypes, and 3) the ability to protect mice against aerogenic tuberculosis challenge. These properties, and the observation that RD1 is the only deletion common to all BCG substrains, makes it likely that the RD1 deletion is the primary attenuating mutation. It remains to be determined if a single gene or a number of genes in this region causes the attenuated phenotype. The variable colonial morphotype switch does suggest that a protein regulating cell wall biogenesis is affected. Notably, defined mutations affecting the cyclopropanation of mycolic acids (Glickman et al., 2000) or the synthesis or export of phthiocerol dimycoseroate (Cox et al., 1999) have been found to correlate with decreased virulence and altered colony morphotypes in *M. tuberculosis* and thus represent attractive candidate genes that might be regulated by an RD1-encoded gene. The *M. tuberculosis* ΔRD1 mutant provides a precisely defined background strain by which to determine virulence and colony morphology related genes.

BCG is currently the only antituberculous vaccine available for use in humans. In many animal models, BCG has been shown to induce protective immunity against *M. tuberculosis* challenge (Opie and Freund, 1937; Hubbard et al., 1992; Baldwin et al., 1998) and in addition, has demonstrated protection against the most severe and fatal form of TB in children (Rodrigues et al., 1991). However, BCG has shown variable efficacy in protecting adults from pulmonary TB (Tuberculosis Prevention Trial, 1980; Hart and Sutherland, 1977; Bloom and Fine, 1994). Due to the uncertain efficacy of BCG, particularly in TB-endemic countries, the development of improved tuberculosis vaccines has become an international research priority.

Our challenge studies have demonstrated that the protective immune responses elicited by immunization with *M. tuberculosis* H37Rv ΔRD1 in mice are at least as strong as the protective responses induced by vaccination with BCG. The *M. tuberculosis* H37Rv ΔRD1 mutant also retains the BCG-associated property of limited spread to the lung following subcutaneous immunization. Restricted dissemination of the ΔRD1 mutant to the lung suggests it should have a favorable overall safety profile. Also, the unmarked mutant of *M. tuberculosis* H37Rv ΔRD1 provides a single deletion strain whereby other attenuating mutations can be readily engineered. Since the risk of reversion to wild-type virulence decreases substantially with each additional attenuating mutation, *M. tuberculosis* mutants harboring deletions in two or three separate genetic loci should provide a much safer vaccine for long term use.

*M. tuberculosis* mutants with RD1 deletions represent attractive candidates as novel vaccines for TB prevention. These mutants, derived from a single mutagenic event from the parental *M. tuberculosis* strain, replicate more efficiently in vivo than BCG, especially early in infection. This enhanced rate of proliferation for the RD1-deleted strains, relative to BCG, may lead to the induction of increased protective immunity in humans, after vaccination with *M. tuberculosis* H37Rv ΔRD1. Moreover, they could also be more immunogenic as there exist at least 129 ORFs present in *M. tuberculosis* H37Rv that are absent from *M. bovis* (Behr et al., 1999). Since some of these ORFs are likely to encode regulatory proteins affecting the expression of other genes, there could be hundreds of antigens expressed in *M. tuberculosis*-infected cells that are absent from BCG-infected cells. Thus, RD1 deletion mutants constructed from human *tubercle bacilli* could protect humans against disease substantially better than BCG.

EXAMPLE 2

Vitamin Auxotrophs of *Mycobacterium Tuberculosis* are Attenuated and Protect Against Tuberculosis This example describes experimental methods and results that establish that deleting genes that control vitamin production in a virulent *M. tuberculosis* causes the *M. tuberculosis* to become avirulent and sustain an infection in mammals, and protect the mammal against challenge with a virulent *M. tuberculosis*.

Given the importance of NAD and nicotinamide (vitamin B3) and pantothenate (vitamin B5) as cofactors involved in carbon utilization, energy transduction (Abiko, 1975; Jackowski, 1996) and the biosynthesis of the complex lipid cell wall of *M. tuberculosis*, we hypothesized that mutations in the biosynthetic pathways for NAD and pantothenate could lead to the generation of mutant strains that retain a limited ability to replicate and subsequently get cleared within the host tissues. In *M. tuberculosis*, the nadABC operon controls the de novo biosynthesis of NAD. Similarly, the panC and panD genes that are organized in an operon control the rate-limiting step in the de novo biosynthesis of pantothenate. We constructed deletion mutants of *M. tuberculosis* in the nadBC and panCD genes using specialized transduction, as described in Example 1. The mutant strains mc²3122 (ΔnadBC) and mc²6001 (ΔpanCD) were auxotrophic for nicotinamide and pantothenate respectively. The in vitro reversion frequencies of the respective mutations were found to be less than $10^{-10}$ events per generation.

Figure 6:
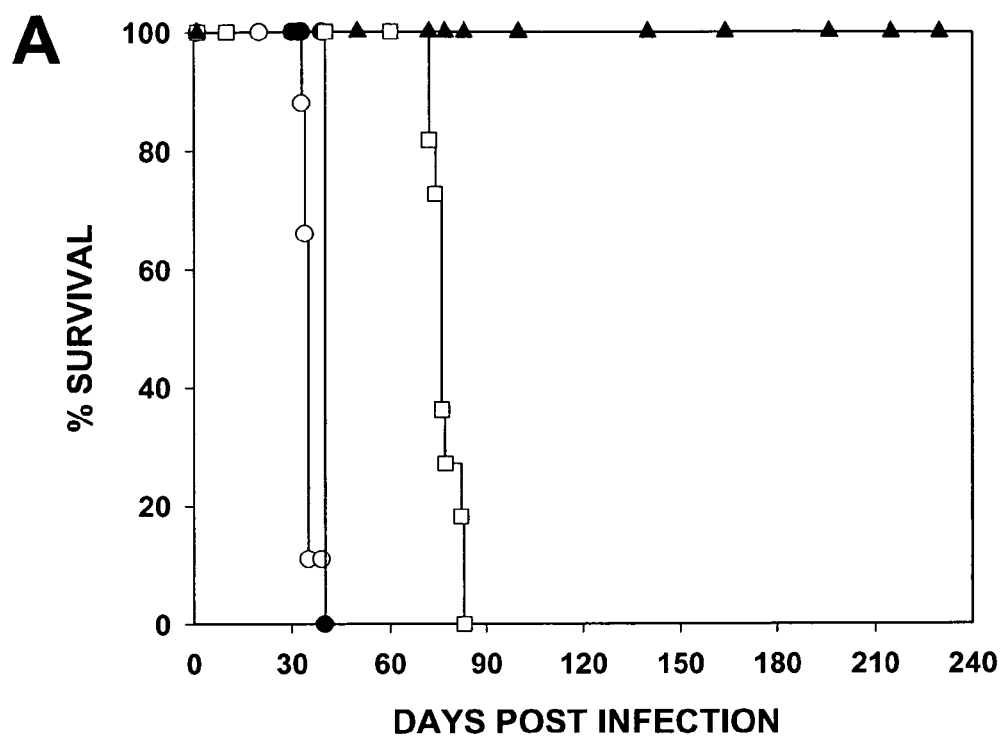
Figure 6:
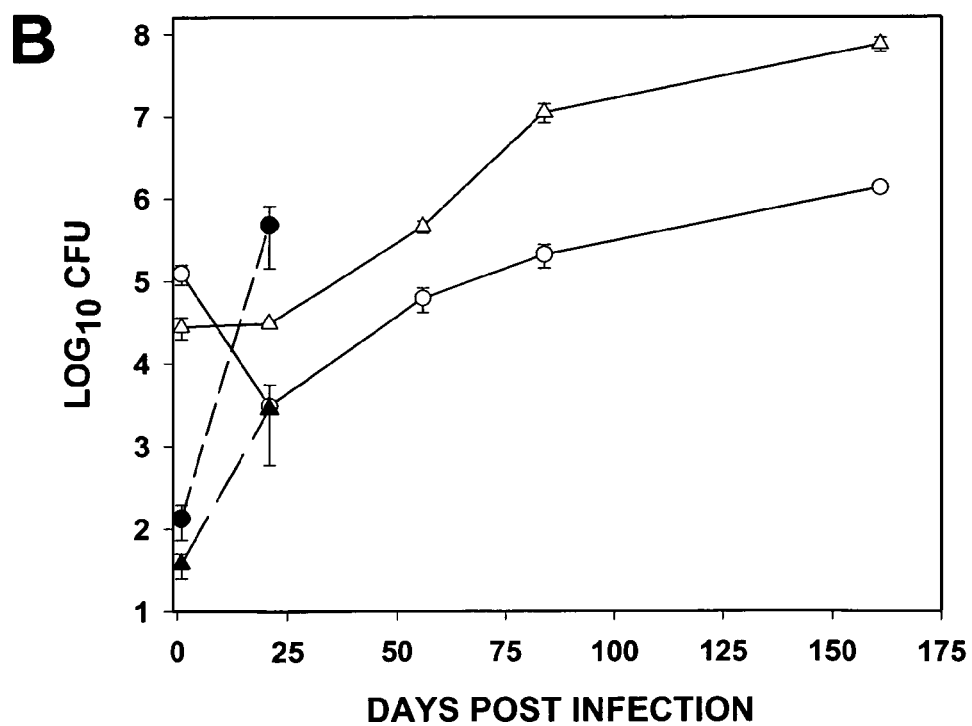

The safety and attenuation of ΔnadBC and ΔpanCD auxotrophic mutants were assessed by infection of immune-compromised SCID mice. SCID mice infected with wild-type *M. tuberculosis* and the ΔnadBC mutant succumbed to infection in about 5 weeks (data not shown). This result clearly indicates that in the absence of T-cell immunity, intermediates of NAD biosynthetic pathway, such as nicotinamide, are readily available in the macrophages to support the growth of the ΔnadBC mutant. In contrast all mice infected with the ΔpanCD mutant survived longer than 30 weeks, demonstrating the severe attenuation of this mutant strain. The full virulence phenotype was restored when the panCD wild type alleles were integrated into the chromosome of the ΔpanCD mutant in single copy, suggesting the observed attenuation in ΔpanCD to be due to the requirement of pantothenate for growth and not due to polar effects of the mutation on downstream genes. SCID mice infected with the same dose of conventional BCG-Pasteur vaccine strain succumbed to infection within 80 days (FIG. 6A) in accordance with earlier reports (Guleria, 1996). Enumeration of bacterial burdens in SCID mice infected with wild type *M. tuberculosis* H37Rv and the complementing strain (panCD in single copy integrated into the chromosome) showed a rapid increase in bacterial numbers in spleen, liver and lung before they succumbed to infection. In contrast, mice infected with ΔpanCD mutant, showed an initial drop in bacterial numbers in spleen and liver followed by a steady increase to reach $10^8$ in the lungs at 160 days, at which time all mice were still alive (FIG. 6B).

Figure 7:
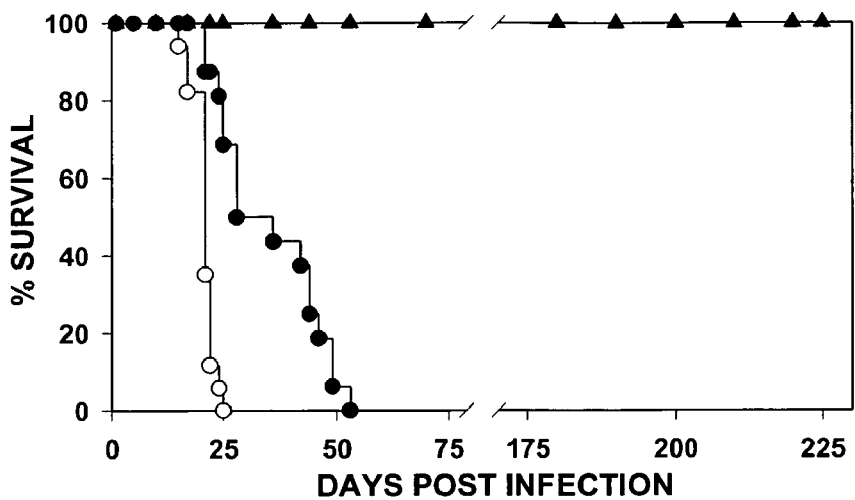
Figure 7:
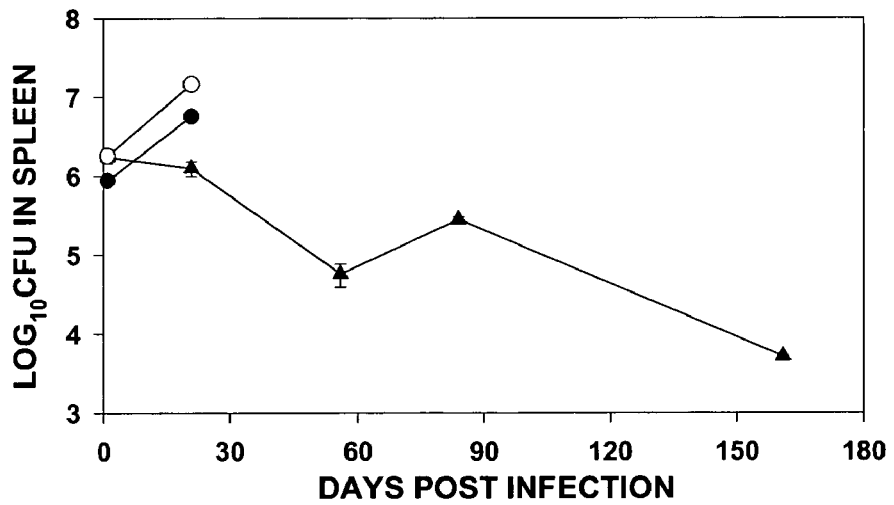
Figure 7:
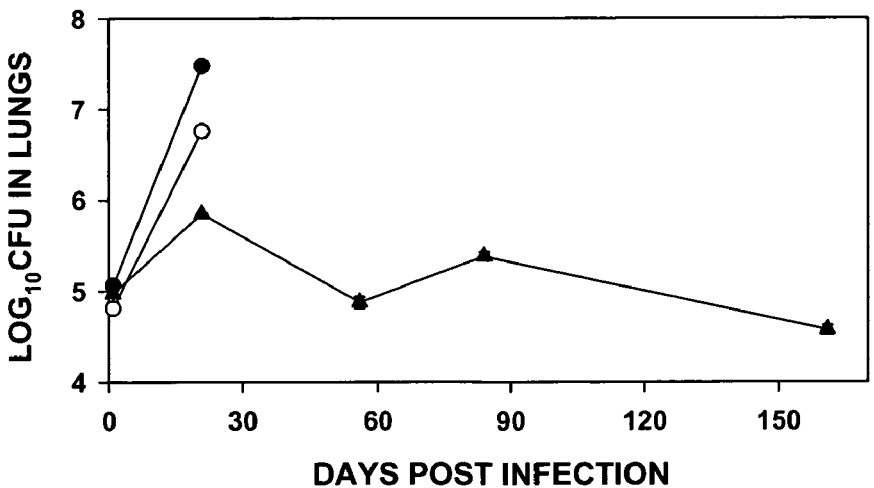

Having demonstrated the significant attenuation of ΔpanCD mutant, we sought to address the in vivo growth characteristics of this mutant in immune-competent BALB/c mice. All BALB/c mice infected with H37Rv succumbed to infection by day 25 with a MST of 22 days. Similarly, mice infected with the panCD-complemented strain were highly virulent with 100% mortality between 3-8 weeks post-infection similar to the wild type strain, with a MST of 28 days. In contrast, all mice infected with ΔpanCD mutant survived for over 33 weeks demonstrating the severe attenuation phenotype of this mutant in immune-competent mice (FIG. 7A). Interestingly, bacterial enumeration at three weeks post infection showed 1 log increase in the ΔpanCD numbers in lungs followed by a state of persistence with the onset of adaptive immune response. This growth characteristic was observed only in the lung but not in spleen or liver (FIG. 7B,C). A desirable trait of an effective live attenuated vaccine strain is its ability to grow within the host in a limited fashion in order to produce in vivo all the important protective antigens (McKenney, 1999; McKenny, 2000; Kanai, 1955). The ΔpanCD mutant exhibits this characteristic in the lung, which is the primary site of infection in humans and does not get cleared over a prolonged period in all the three organs. The earlier auxotrophs of *M. tuberculosis* failed to grow in any of the organs and hence failed to adequately protect against experimental challenge in guinea pigs (Jackson, 1999), or mice.

The ability of the ΔpanCD mutant to exhibit limited growth in the lung until the onset of adaptive immune response suggests that an unidentified putative pantothenate permease is able to transport this nutrient into resting macrophages, as in the SCID mice. A sodfum-dependent pantothenate permease actively transports pantothenate into the cell of *Escherichia coli* (Vallari and Rock, 1985; Jackowski and Alix, 1990), *Plasmodium falciparum* (Saliba and Kirk, 2001) and mammals. Subsequent activation of macrophages leads to restricted supply of this nutrient within the phagosome resulting in growth arrest of the mutant. Pantothenic acid or its derivatives have been reported to confer resistance to radiation and oxidative stress by virtue of their role in biosynthesis of CoA and also by indirectly increasing the cellular supply of glutamate, a precursor of glutathione (Slyshenkov, 1995). Pantothenate kinase (PanK) mutants of Drosophila display membrane defects and improper mitosis and meiosis due to decreased phospholipid biosynthesis (Afshar et al., 2001). The disruption of de novo pantothenate biosynthesis causes an increased susceptibility of the ΔpanCD mutant to reactive oxygen and nitrogen intermediates that are released within activated macrophages.

Figure 8:
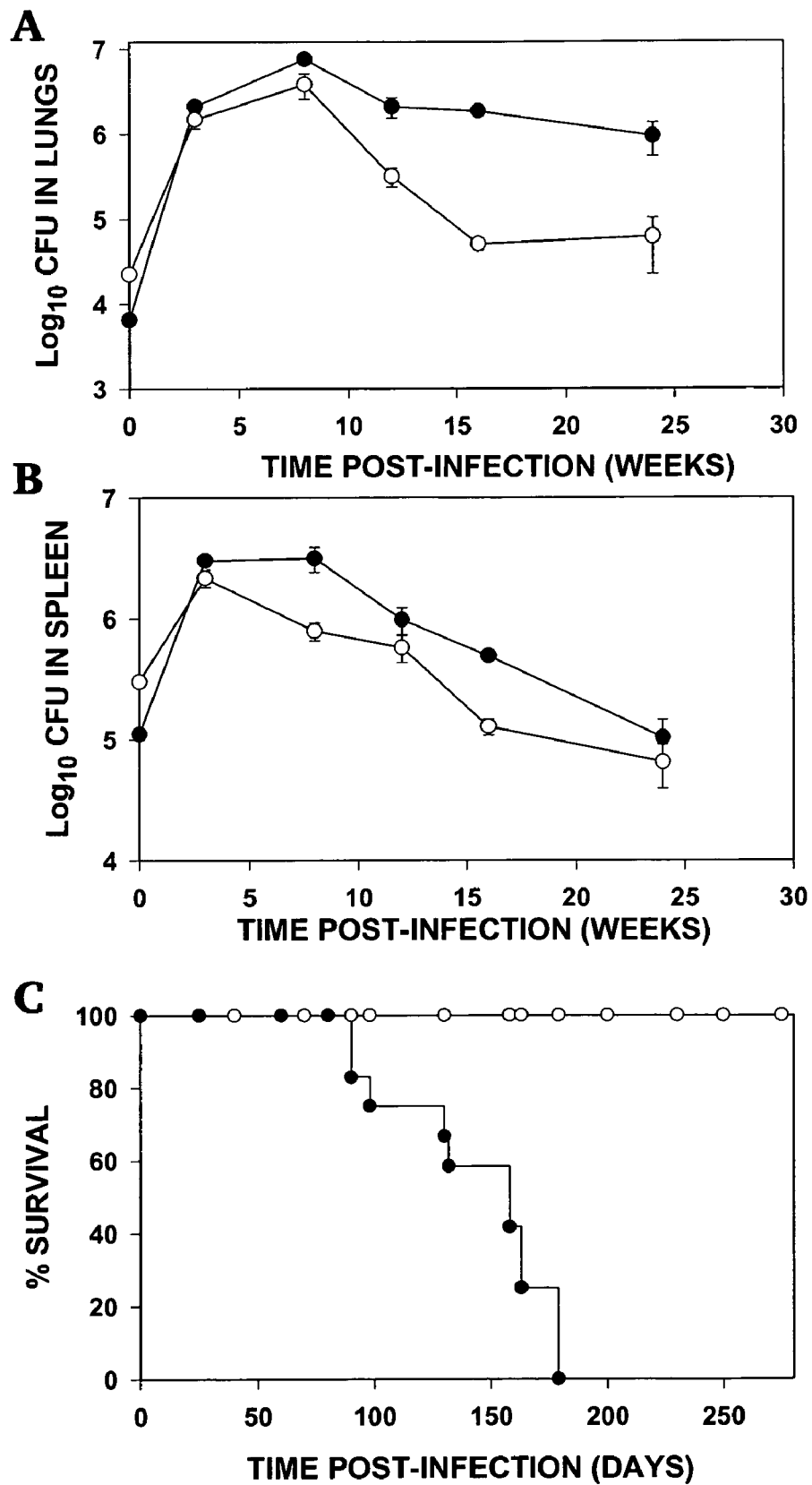
Figure 9:
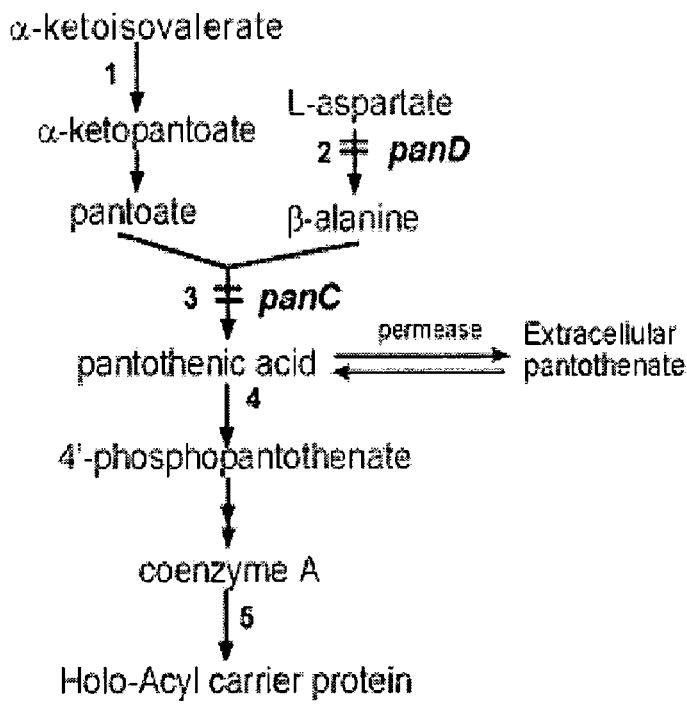
Figure 9:
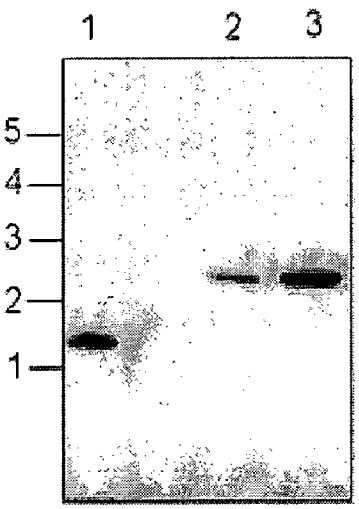
Figure 9:
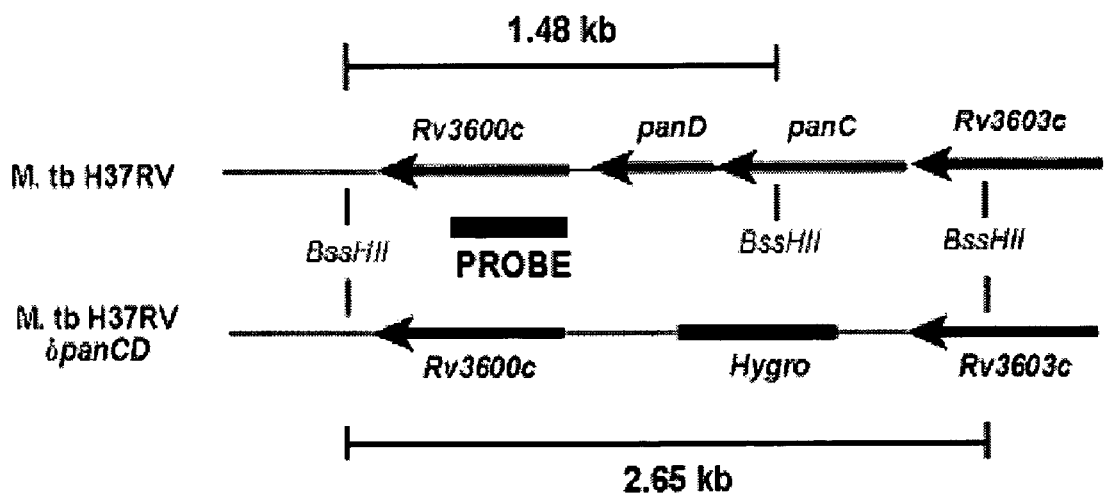
Figure 10:
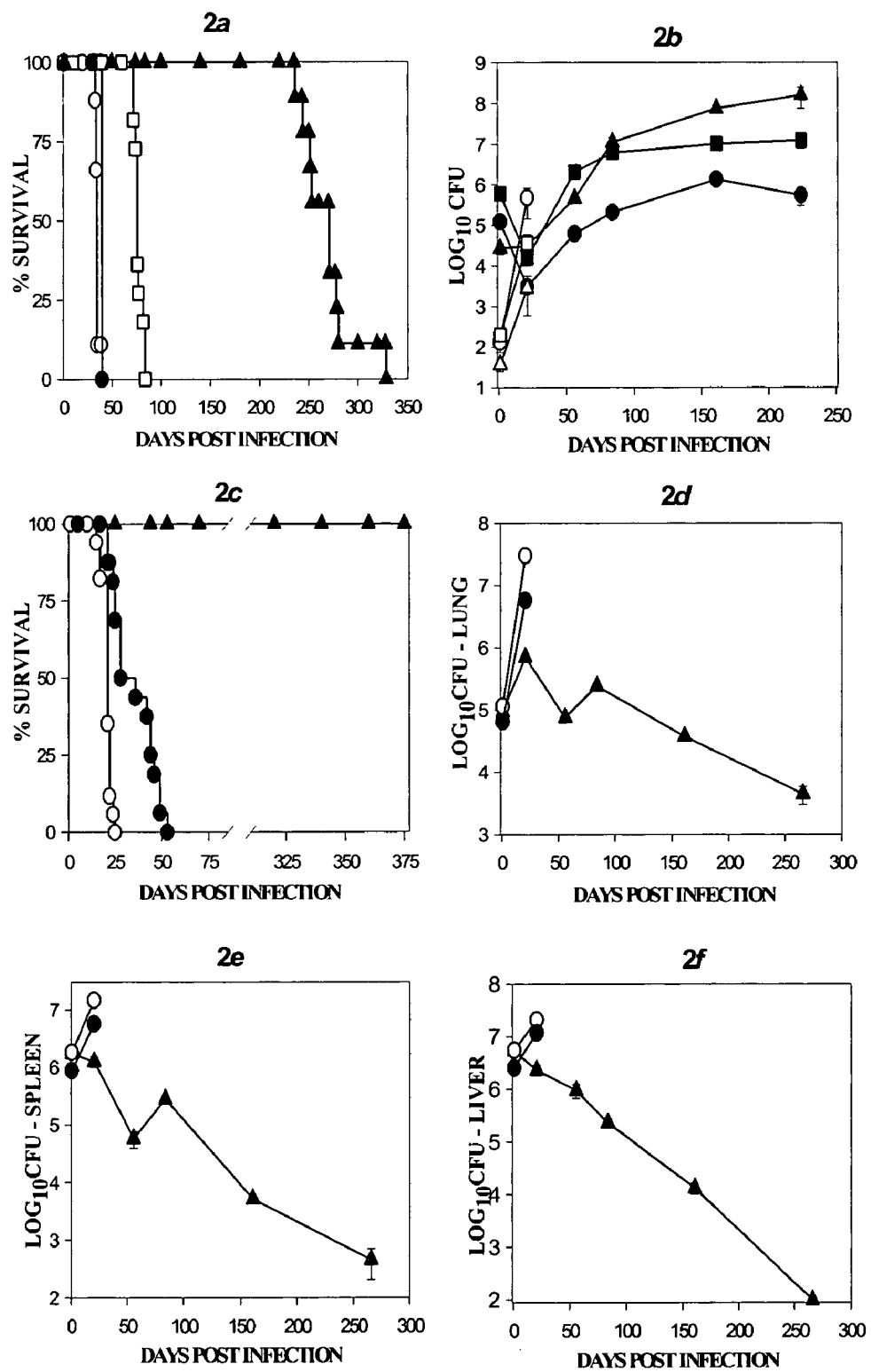

Having observed the ΔnadBC mutant to be non-attenuated in SCID mice, we chose to study the in vivo growth kinetics of this mutant in the more resistant C57BL/6 mice background. During the first three weeks of infection, the number of wild type and mutant bacteria recovered from all three organs showed little or no difference. Their numbers gradually increased in the lungs to reach $10^6$. However, with the onset of adaptive immune response at three weeks, when the growth of bacteria in the lungs of mice infected with H37Rv became constant and tightly controlled, bacterial load in the lungs of mice infected with ΔnadBC mutant showed a constant tendency for clearance to reach more than 1.5 log drop in the bacterial numbers compared to mice infected with wild type strain (FIG. 8A). This difference was preserved up to 24 weeks following infection.

The reduced ability of the ΔnadBC mutant to sustain an infection was accompanied by attenuated virulence clearly seen from the survival experiment (FIG. 8C). While all mice infected with the wild type strain succumbed to infection between day 90 and 179 (MST 116 days) all mice infected with the ΔnadBC mutant (n=12) remain alive for a period of more than 8 months (FIG. 8C).

Our observation of the attenuation phenotype of ΔnadBC mutant became obvious only after the onset of immune response, suggesting that once the macrophages become activated, they restrict the amount of available NAD or NAD intermediates causing a restricted growth of the mutant strain. This would be in agreement with the recently reported observations that a significant part of antimicrobial function of the macrophages could be attributed to the IFN-γ promoted enhanced expression of indolamine 2-oxygenase (IDO), the inducible enzyme controlling L-tryptophan catabolic pathway causing an almost complete depletion of L-tryptophan pool. The enhanced catabolism of L-tryptophan leads to increased de novo biosynthesis of NAD needed to protect the cells from the free radicals formed as a result of macrophage activation. Recently, several studies have demonstrated the involvement of the tryptophan catabolism in the antimicrobial mechanisms of the activated macrophages. Induction of IDO was found responsible for the inhibition of intracellular growth of *Toxoplasma, Leishmania, Legionella* and *Chlamydia*. The restricted intracellular growth of ΔnadBC mutant could be explained with the very little amount of free NAD or NAD intermediates available within the activated macrophages.

Having established the safety and persistence of ΔpanCD and ΔnadBC in immunocompetent mice, the protective efficacy of these mutants were evaluated using an aerosol challenge model with virulent *M. tuberculosis*, using the methods described in Example 1. The aerosol route of infection was chosen, as this is the natural route of infection in humans. To assess the capacity of the auxotrophic vaccines to restrict growth of virulent *M. tuberculosis* in the organs of infected mice, bacterial numbers were enumerated one month post-infection in lung and spleen. See Table 3. In the unimmunized controls, bacterial numbers rose rapidly in the spleen and lungs, in contrast mice infected with a single dose of ΔpanCD displayed significant reduction in bacterial numbers in the spleen and lung ($p<0.05$, in comparison to unimmunized controls). Mice given two doses of ΔpanCD displayed a statistically significant reduction in the bacterial numbers to 4.5 log units in the lung ($p<0.01$) and 3.7 log units in the spleen ($p<0.05$). Mice vaccinated with BCG showed comparable reduction in bacterial burden in the lung and spleen to 3.3 log units and 4.7 log units respectively ($p<0.01$). Mice immunized with one or two doses of ΔnadBC mutant conferred statistically significant protection ($p<0.01$ in comparison to unimmunized group) that is comparable to the protection afforded by BCG vaccination. Interestingly, mice immunized with the ΔnadBC mutant showed no detectable CFUs in the spleen suggesting that the vaccination completely prevented the hematogenous spread of wild type *M. tuberculosis* following aerosol challenge.

TABLE 3

| Experimental Group | Lung CFUs ($\log_{10}$) | Spleen CFUs ($\log_{10}$) |
|---|---|---|
| A | | |
| Naive | 4.05 ± 0.21 | 3.94 ± 0.21 |
| ΔnadBC (1 × sc) | 3.37 ± 0.40** | <2** |
| ΔnadBC (2 × sc) | 3.6 ± 0.35** | <2** |
| BCG (1 × sc) | 3.46 ± 0.19** | <2** |
| B | | |
| Naive | 5.56 ± 0.05 | 4.35 ± 0.21 |
| ΔpanCD (1 × sc) | 4.99 ± 0.17 (−0.57)* | 3.65 ± 0.15 (−0.70)* |
| ΔpanCD (2 × sc) | 4.55 ± 0.09 (−1.01)** | 3.73 ± 0.21 (−0.62)* |
| BCG (1 × sc) | 4.71 ± 0.21 (−0.85)** | 3.35 ± 0.20 (−1.00)** |

*$p < 0.05$ compared to naïve,
**$p < 0.01$ compared to naïve

Table 3. The attenuated *M. tuberculosis* ΔnadBC and ΔpanCD mutants protect against aerogenic challenge with *M. tuberculosis* Erdman. Groups of C57BL/6 mice (5 mice per group) were vaccinated subcutaneously either once or twice (6 weeks apart) with $10^6$ CFUs of mutant strains. Control mice were vaccinated subcutaneously with $10^6$ CFUs of BCG-Pasteur. Three months after the initial immunization with either ΔnadBC or ΔpanCD mutant or BCG, the mice were aerogenically challenged with approximatedly 100 CFUs of acriflavin-resistant M. tuberculosis Erdman (Ac'MTB) strain as described earlier (Collins, 1985) After 28 days, the challenged mice were sacrificed, and the lungs and spleens of individual mice were removed aseptically and homogenized separately in 5 ml of Tween 80-saline using a Seward stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg of thiophenecarboxylic acid hydrazide (Sigma Chemical Co., St Louis, Mo.) per ml to inhibit growth of any residual BCG. The CFU results were evaluated using the one-way ANOVA analysis of the Graph Pad InStat program. The numbers in paranthesis represent the differences between naïve and vaccinated organ CFUs.

In order to test the ability of the auxotrophic mutants to confer long lasting immunity, mice were challenged 7 months after an initial subcutaneous immunization with the ΔnadBC mutant. See Table 4. Mice immunized with ΔnadBC displayed significantly reduced numbers of the challenge organism in the lungs and no detectable numbers in the spleen comparable to the numbers seen in the BCG vaccinated mice. The results suggest that the ΔnadBC vaccine strain is able to persist within the mouse organs sufficiently long to mount a long lasting immunity to control subsequent infection.

TABLE 4

| Experimental Group | Lung CFUs ($\log_{10}$) | Spleen CFUs ($\log_{10}$) |
|---|---|---|
| Naive | 4.61 ± 0.07 | 4.07 ± 0.20 |
| BCG | 4.00 ± 0.13* | 2 |
| NAD (1 × iv) | 3.28 ± 0.15** | <2 |
| NAD (2 × iv) | 2.95 ± 0.14** | <2 |
| NAD (1 × sc) | 4.05 ± 0.12* | <2 |
| NAD (2 × sc) | 3.94 ± 0.13* | <2 |

*$P < 0.05$;
**$P < 0.01$ by Dunnett's Multiple Comparison Test

Table 4. Immunizations with the ΔnadBC mutant confer long-term protection against an aerosol challenge. Groups of C57BL/6 mice (5 mice per group) were vaccinated subcutaneously or intravenously either once or twice (6 weeks apart) with $10^6$ CFUs of ΔnadBC mutant. Control mice were vaccinated subcutaneously with $10^6$ CFUs of BCG-Pasteur. Seven months after the initial immunization with either ΔnadBC mutant or BCG, the mice were aerogenically challenged with approximately 50 CFUs of acriflavin-resistant M. tuberculosis Erdman (Ac'MTB) strain and the bacterial numbers at 28 days post challenge enumerated as described in Table 1.

To the best of our knowledge this is the first report of any M. tuberculosis auxotrophic vaccines administered subcutaneously to confer protection comparable to the conventional BCG vaccine strain in a mouse model of infection. Mice vaccinated with the ΔpanCD and ΔnadBC survived for over one year following the aerosol challenge indicating the protection and safety of these vaccine strains.

EXAMPLE 3

A Pantothenate Auxotroph of Mycobacterium Tuberculosis is Highly Attenuated and Protects Mice Against Tuberculosis This Example is published as Sambandamurthy et al., 2002. Example summary.

With the advent of HIV and the widespread emergence of drug resistant strains of Mycobacterium tuberculosis, newer control strategies in the form of a better vaccine could decrease the global incidence of tuberculosis. A desirable trait in an effective live attenuated vaccine strain is its ability to persist within the host in a limited fashion in order to produce important protective antigens in vivo (Kanai and Yanagisawa, 1955; McKenney et al., 1999). Rationally attenuated M. tuberculosis vaccine candidates have been constructed by deleting genes required for growth in mice (Jackson et al., 1999; Hondalus et al., 2000; Smith et al., 2001). These candidate vaccines failed to elicit adequate protective immunity in animal models, due to their inability to persist sufficiently long within the host tissues. Here we report that an auxotrophic mutant of M. tuberculosis defective in the de novo biosynthesis of pantothenic acid (vitamin B5) is highly attenuated in immunocompromised SCID mice and in immunocompetent BALB/c mice. SCID mice infected with the pantothenate auxotroph survived significantly longer than mice infected with either BCG vaccine or virulent M. tuberculosis (250 days, vs. 77 days, vs. 35 days). Subcutaneous immunization with this auxotroph conferred protection in C57BL/6J mice against an aerosol challenge with virulent M. tuberculosis, which was comparable to that afforded by BCG vaccination. Our findings highlight the importance of de novo pantothenate biosynthesis in limiting the intracellular survival and pathogenesis of M. tuberculosis without reducing its immunogenicity in vaccinated mice.

Materials and Methods

Media and Strains. M. tuberculosis H37Rv, M. tuberculosis Erdman and M. bovis BCG Pasteur were obtained from the Trudeau Culture Collection (Saranac Lake, N.Y.) and cultured in Middlebrook 7H9 broth and 7H11 agar supplemented with 10% OADC, 0.5% glycerol, and 0.05% Tween 80. When required, pantothenate (24 µg/ml), hygromycin (50 µg/ml) or kanamycin (25 µg/ml) was added. Stock strains were grown in Middlebrook 7H9 broth in roller bottles and harvested in mid-logarithmic growth phase, before being stored in 1 ml vials at −70° C. until required.

Disruption of panCD genes in M. tuberculosis. Specialized transduction was employed to disrupt the chromosomal copy of the panCD genes as described (U.S. Pat. No. 6,271,034). Briefly, the 823 bp region upstream to the panC gene was amplified using primers Pan1 (5'-GTGCAGCGC-CATCTCTCA-3')(SEQ ID NO:9)and Pan2 (5'-GTTCAC-CGGGATGGAACG-3')(SEQ ID NO:10). A 716 bp region downstream to the panD gene was amplified using primers Pan3 (5'-CCCGGCTCGGTGTGGGAT-3') (SEQ ID NO:11) and Pan4 (5'-GCGCGGTATGCCCGGTAG-3')(SEQ ID NO:12). PCR products were cloned with the TOPO TA cloning kit (Invitrogen, Calif.), and sequenced. PCR products were subsequently cloned into pJSC347, flanking a hygromycin cassette to create pSKV1. PacI digested pSKV1 was ligated into the temperature-sensitive mycobacteriophage phAE159 derived from TM4 and transduced as described earlier (Glickman et al., 2000; Raman et al., 2001). Genomic DNAs from hygromycin-resistant and pantothenate-requiring colonies were digested with BssHII, and probed with a 716 bp downstream region, flanking the *M. tuberculosis* panCD operon to confirm the deletion. For complementation, the *M. tuberculosis* panCD operon was amplified by PCR from genomic DNA with its putative promoter, cloned with TA cloning kit, sequenced, and subcloned into pMV306kan, a site-specific integrating mycobacterial vector.

Animal infections. C57BL/6, BALB/cJ and BALB/c SCID mice (6-8 weeks old) were purchased from Jackson Laboratories and were infected intravenously through the lateral tail vein. For time-to-death assays, BALB/c SCID mice were infected intravenously with $1\times10^2$ CFU of *M. tuberculosis* H37Rv, $1\times10^2$ CFU of panCD-complemented strain, $1\times10^5$ CFU of ΔpanCD mutant, or $1\times10^5$ CFU of *M. bovis* BCG-P. For mouse organ CFU assays, BALB/cJ mice were infected with $1\times10^6$ CFU of *M. tuberculosis* H37Rv or the panCD-complemented strain or the ΔpanCD mutant. At appropriate time points, groups of 4-5 mice were sacrificed and the selected organs were homogenized separately in PBS/0.05% Tween 80, and colonies were enumerated on 7H11 plates grown at 37° C. for 3-4 weeks (see McKinney et al., 2000). Pathological examination was performed on tissues fixed in 10% buffered formalin. The CFU results were evaluated using the one-way ANOVA analysis of the Graph Pad InStat program. All animals were maintained in accordance with protocols approved by the Albert Einstein College of Medicine Institutional Animal Care and Use Committee.

Vaccination Studies. Groups of C57BL/6 mice (5 mice per group) were vaccinated subcutaneously either once or twice (6 weeks apart) with $1\times10^6$ CFU of the ΔpanCD mutant strain. Control mice were vaccinated subcutaneously with $1\times10^6$ CFU of *M. bovis* BCG-P. Three months after the initial immunization with either the ΔpanCD mutant or BCG, the mice were aerogenically challenged with approximately 50-100 CFU of *M. tuberculosis* Erdman strain as described earlier. At 28 days following aerosol challenge, the challenged mice were sacrificed; the lungs and spleens of individual mice were removed aseptically and homogenized separately in 5 ml of Tween 80-saline using a Seward Stomacher 80 blender (Tekmar, Cincinnati, Ohio). The homogenates were diluted serially in Tween 80 saline and plated on Middlebrook 7H11 agar with or without appropriate supplements as required. Samples from the BCG-vaccinated controls were plated on 7H11 agar containing 2 mg/ml of thiophene-2-carboxylic acid hydrazide (Sigma) to inhibit growth of any residual BCG.

Results and Discussion

Lipid biosynthesis and metabolism have been shown to play a pivotal role in the intracellular replication and persistence of *M. tuberculosis* (Cox et al., 1999; Camacho et al., 1999; Glickman et al., 2000; De Voss et al., 2000; Manca et al., 2001; McKinney et al., 2000). Therefore, we sought to globally impair the ability of this bacterium to synthesize lipids. Pantothenic acid (vitamin B5) is an essential molecule required for the synthesis of coenzyme A (CoA) and acyl carrier protein (ACP), that play important roles as acyl group carriers in fatty acid metabolism, the tricarboxylic acid cycle, biosynthesis of polyketides and several other reactions associated with intermediary metabolism (Jackowski, 1996). Bacteria, plants and fungi synthesize pantothenate from amino acid intermediates, whereas it is a nutritional requirement in higher animals (FIG. 9*a*).

We constructed a double deletion mutant of *M. tuberculosis* in the panC and panD genes that are involved in the de novo biosynthesis of pantothenate (FIG. 9*b,c*). The ΔpanCD mutant was found to be auxotrophic for pantothenate with no detectable reversion to prototrophy when $1\times10^{10}$ cells were plated on minimal medium. The growth rate of the mutant was identical to wild type H37Rv in broth cultures in the presence of exogenous pantothenate (data not shown). The attenuation of the ΔpanCD mutant was assessed by infection of immunocompromised SCID mice. SCID mice infected intravenously with H37Rv succumbed to the resulting infection in about 5 weeks. In contrast, all mice infected with the ΔpanCD mutant survived for more than 36 weeks (average, 253 days) (FIG. 10*a*). This attenuation is due to pantothenate auxotrophy as the full virulence phenotype was restored when the panCD wild type genes were integrated into the chromosome of the ΔpanCD mutant in single copy. Enumeration of bacterial burdens in SCID mice infected with H37Rv and the ΔpanCD-complemented strain showed a rapid increase in bacterial numbers in the spleen, liver and lung, until they succumbed to infection. In contrast, mice infected with the ΔpanCD mutant showed an initial drop in bacterial numbers in the spleen and liver followed by a gradual increase in the number of viable bacteria, reaching $1\times10^6$ colony-forming units (CFU) by day 224 (FIG. 10*b*). Notably, the CFU values increased to $1\times10^8$ in the lungs of the infected mice. The ability of ΔpanCD-infected SCID mice to survive despite a substantial bacterial burden in their lungs emphasizes the extent of attenuation in this mutant and compares with the phenotype observed with the *M. tuberculosis* whiB3 and sigH mutants described recently (Steyn et al., 2000; Kaushal, 2000). Notably, SCID mice infected with bacille Calmette-Guerin-Pasteur (BCG-P) strain succumbed to infection by 83 days (Weber et al., 2000) in contrast to the prolonged survival observed in ΔpanCD-infected mice.

Studies in immunocompetent mice further demonstrate the attenuation of the ΔpanCD mutant. Survival studies showed that BALB/c mice infected with H37Rv succumbed to infection by day 25 (average, 21 days) and mice infected with an identical dose of the panCD-complemented strain succumbed to infection between days 21 to 53 (average, 37 days). Importantly, all mice infected with $1\times10^6$ CFU of the ΔpanCD mutant survived 375 days, when the experiment was terminated (FIG. 10*c*). At 3 weeks post infection, in contrast to the H37Rv strain, BALB/c mice infected with ΔpanCD mutant showed a 10-fold increase in bacterial numbers in the lungs followed by a gradual decline in viable numbers over the next 38 weeks of infection (FIG. 10*d*) and the bacterial burden gradually declined in the spleen and liver throughout the course of infection (FIG. 10*e*). Histopathologic examination of the lungs from mice infected with either H37Rv or the ΔpanCb-complemented strain, showed severe, diffuse lobar granulomatous pneumonia (FIGS. 11*a,b*). The pneumonia affected more than 50% of the lung, and was pyogranulomatous with marked necrosis in the advanced consolidated areas, particularly in the lungs of mice challenged with H37Rv. Both of these strains caused severe granulomatous splenitis and widespread granulomatous hepatitis. At 3 weeks post-infection with the ΔpanCD mutant, low to moderate numbers of focal infiltrates of mononuclear cells scattered throughout the lung were seen (FIG. 11*c*). The spleen was moderately enlarged with scattered granulomas. Similarly, the liver showed numerous focal granulomas. At 24 weeks post-infection, consistent with the bacterial numbers, histological examination of the lungs from mice infected with the ΔpanCD mutant showed only occasional focal mild infiltrations, predominately lymphocytic (FIG. 11*d*). The spleen showed only mild histiocytic hyperplasia and there were fewer, focal, predominately lymphocytic accumulations in the liver.

The mechanisms that allow the persistence of the ΔpanCD mutant bacteria for over 8 months in the SCID mouse model remain unclear. We speculate the functional role of an unidentified permease in transporting adequate amount of pantothenate in the ΔpanCD mutant that allows its persistence but not the ability to cause disease. A pantothenate permease that transports pantothenate have been described in *Plasmodium falciparum* and *Escherichia coli* (Saliba and Kirk, 2001; Jackowski and Alix, 1990). In the lungs of immunocompetent mice, an initial growth of the ΔpanCD mutant during the first 3 weeks is followed by a steady decline in bacterial numbers following the onset of an adaptive immune response. The intracellular lifestyle of *M. tuberculosis* poses significant challenges to the bacterium in acquiring essential nutrients. Pantothenic acid or its derivatives have been shown to confer resistance to oxidative stress (Slyshenkov et al., 1996) and lack of pantothenate biosynthesis in the ΔpanCD mutant may render it more susceptible to such adverse effects. Likewise, a pantothenate kinase (pank) mutant of Drosophila was shown to display membrane defects and improper mitosis and meiosis due to decreased phospholipid biosynthesis (Afshar et al., 2001). Therefore, it is plausible that the pantothenate salvage pathway is inadequate in restoring full virulence of the ΔpanCD mutant in the absence of a functional de novo biosynthetic pathway.

Figure 11:
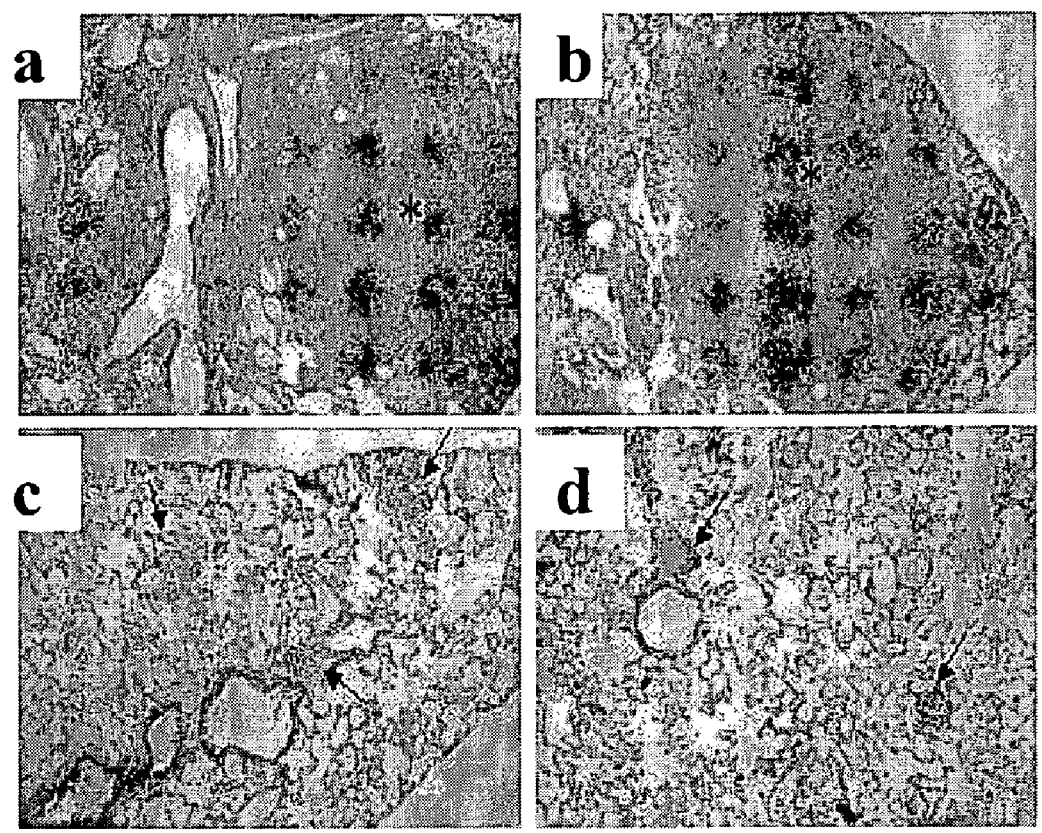
Figure 11:
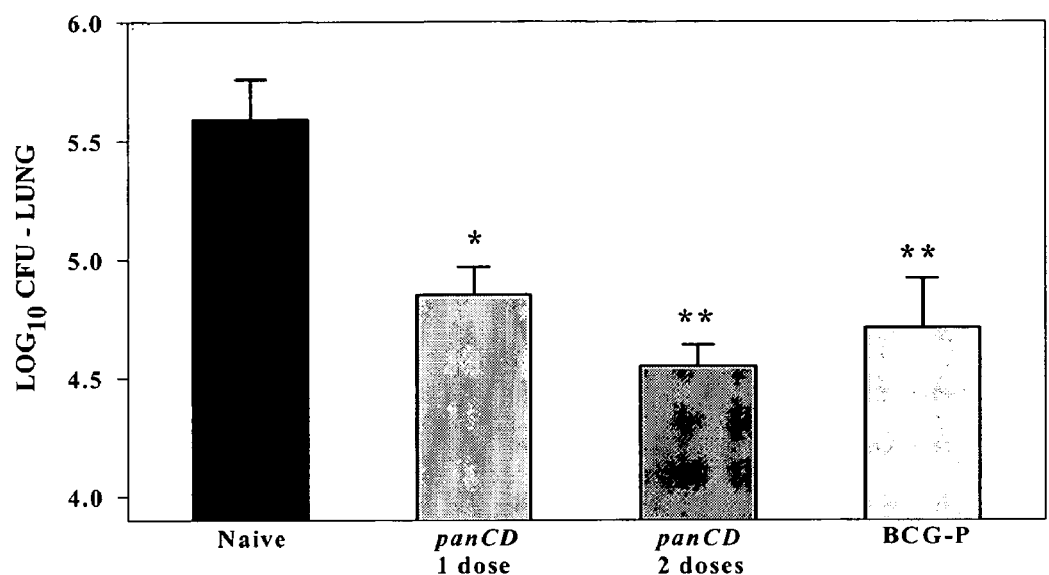
Figure 11:
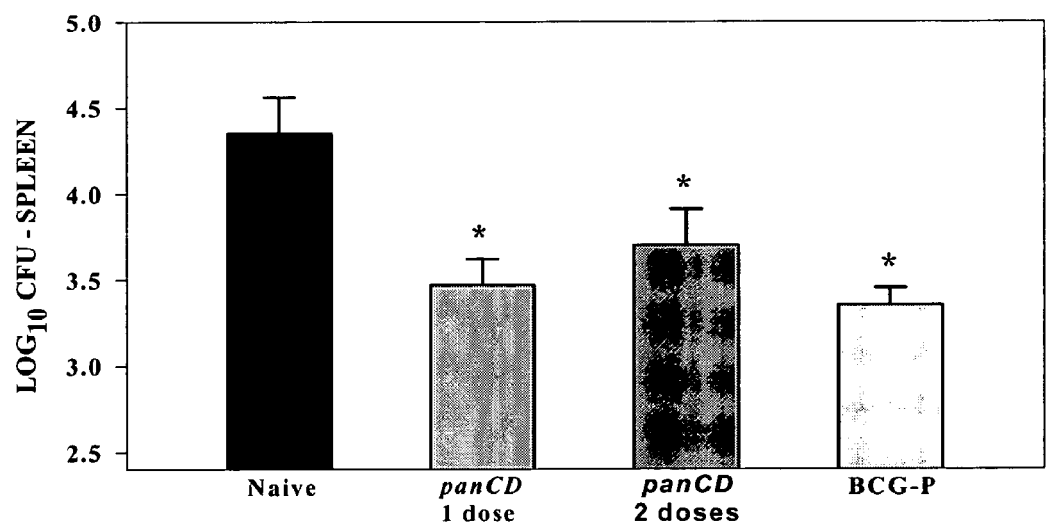

As a test of vaccine potential, immunized mice were challenged with virulent *M. tuberculosis* Erdman by the aerosol route (Collins, 1985). Following subcutaneous immunization, the ΔpanCD mutant could not be detected in the spleens or lungs of mice at 8 and 12 weeks. In the naive controls, the bacterial CFU values increased 10,000-fold in the lung during the first month after challenge. Similarly, substantial dissemination and growth in the spleen was detected within one month of the challenge in naive controls. In contrast, mice immunized with single or double doses of the ΔpanCD mutant displayed statistically significant reductions (P<0.05) in lung and spleen CFU values relative to naive controls. Mice vaccinated with BCG showed similar reduction in organ bacterial burdens compared to the nonimmunized controls (FIG. 11e,f). In these aerogenic challenge studies, no significant differences were detected in the lung and spleen CFU values for mice vaccinated with either the ΔpanCD mutant strain or with BCG. At 28 days after the aerogenic challenge with virulent *M. tuberculosis*, histopathological examination of lungs of ΔpanCD immunized mice revealed a less severe infection relative to the unvaccinated control mice. In controls, severe bronchitis, moderate pneumonia, and spread of the infection to the adjacent lung parenchyma was observed. By comparison, the ΔpanCD vaccinated mice had milder bronchitis and smaller areas of mild interstitial pneumonitis, with localized areas of granulomatous pneumonia in some mice. Importantly, no lung pathology was detected in vaccinated mice at the time of challenge (data not shown). Two groups of mice that were vaccinated with one or two doses of the ΔpanCD mutant and then challenged with *M. tuberculosis* Erdman were active and healthy for more than one year following the virulent challenge. Histopathological analysis of lung sections from these mice showed only mild inflammation and fibrosis despite the chronic infection.

By creating a *M. tuberculosis* strain that is defective in pantothenate biosynthesis, we have taken a critical step in the rational development of an attenuated *M. tuberculosis* vaccine strain. We have shown that a functional pantothenate biosynthetic pathway, which is required for the synthesis of complex mycobacterial lipids, is essential for the virulence of *M. tuberculosis*. Although the precise mechanism of the reduced virulence is unclear, it is reasonable to speculate that this could be due to reduced synthesis of toxic polyketides and secreted lipids or a general slow down of metabolism. *Tubercle bacilli* lacking the two genes required to synthesize pantothenate failed to revert and were highly attenuated and less virulent than BCG vaccine when tested in the rigorous SCID mouse model of infection. Despite the reduced virulence associated with the deletion of the panCD genes, these vitamin auxotrophs remain persistent in vivo as shown by their ability to survive for at least eight months in immunocompetent mice. The persistence of this mutant strain undoubtedly contributes to the substantial immunogenicity seen in the mouse tuberculous challenge model. Overall, the ΔpanCD mutant has many of the characteristics necessary for a live vaccine candidate strain: it is attenuated by a non-reverting mutation and essentially avirulent while being persistent and immunogenic. Given the genetic differences between *M. bovis* and *M. tuberculosis* (Behr et al., 1999), one would predict that a rationally attenuated *M. tuberculosis* strain would have a more relevant repertoire of species-specific antigens and thus should elicit, in humans, more effective protective immune responses against tuberculous infections than BCG.

EXAMPLE 4

The Primary Mechanism of Attenuation of BCG is a Loss of Invasiveness Due to Host Cell Lysis Example Summary Tuberculosis remains a leading cause of death worldwide, despite the availability of effective chemotherapy and a vaccine. BCG, the tuberculosis vaccine, is an attenuated mutant of *M. bovis* that was isolated following serial subcultivations, yet the basis for this attenuation has never been elucidated. A single region (RD1), deleted in all BCG substrains, was deleted from virulent *M. bovis* and *M. tuberculosis* strains and the resulting three ΔRD1 mutants were significantly attenuated for virulence in both immunocompromised and immunocompetent mice. Like BCG, *M. tuberculosis* ΔRD1 mutants protect mice against acrosolized *M. tuberculosis* challenge and these mutants also consistently display altered colonial morphotypes. Interestingly, the ΔRD1 mutants failed to cause necrosis, via lysis, of pneumocytes, a phenotype that had been previously used to distinguish virulent *M. tuberculosis* from BCG. We conclude that the primary attenuating mechanism of BCG is the loss of cytolytic activity, resulting in reduced invasiveness.

Introduction

BCG (bacille Calmette and Guerin), was first isolated from *M. bovis* following serial subculturing of *M. bovis* in 1908 (Calmette and Guerin, 1909). Drs. Calmette and Guerin set out to test the hypothesis that a bovine tubercle *bacillus* could transmit pulmonary tuberculosis following oral administration (Calmette and Guerin, 1905; Gheorghiu, 1996) and developed a medium containing beef bile that enabled the preparation of fine homogenous bacillary suspensions. After the 39th passage, the strain was found to be unable to kill experimental animals (Calmette and Guerin, 1909). Between 1908 and 1921, the strain showed no reversion to virulence after 230 passages on bile potato medium (Gheorghiu, 1996), which is consistent with the attenuating mutation being a deletion mutation. In the animal studies that followed, BCG was shown to be attenuated, but it also protected animals receiving a lethal challenge of virulent *tubercle bacilli* (Calmette and Guerin, 1920). BCG was first used as a vaccine against tuberculosis in a child in 1921 (Weill-Halle and Turpin, 1925). From 1921 to 1927, BCG was shown to have protective efficacy against TB in a study on children (Id.; Calmette and Plotz, 1929) and was adopted by the League of Nations in 1928 for widespread use in the prevention of tuberculosis. By the 1950's, after a series of clinical trials, the WHO was encouraging widespread use of BCG vaccine throughout the world (Fine and Rodrigues, 1990). Although an estimated 3 billion doses have been used to vaccinate the human population against tuberculosis; the mechanism that causes BCG's attenuation remains unknown.

Mahairas et al.(1996) first compared the genomic sequences of BCG and *M. bovis* using subtractive hybridization and found that there were three Regions of Difference (designated RD1, RD2, and RD3) present in the genome of *M. bovis*, but missing in BCG. Behr et al. (Behr et al., 1999) and others (Gordon et al., 2001) later identified 16 large deletions, including RD1 to RD3, present in the BCG genome but absent in *M. tuberculosis*. Eleven of these 16 deletions were unique to *M. bovis*, while the remaining 5 deletions were unique to BCG. One of these 5 deletions, designated RD1 (9454 bp), was absent from all of the BCG substrains currently used as TB vaccines worldwide and it was concluded that the deletion of RD1 appeared to have occurred very early during the development of BCG, probably prior to 1921 (Behr et al., 1999). It is reasonable to hypothesize that RD1 was the primary attenuating mutation first isolated by Calmette and Guerin to generate BCG from *M. bovis*. Attempts to restore virulence to BCG with RD1-complementing clones have been unsuccessful (Mahairas et al., 1996).

Results

Figure 12:
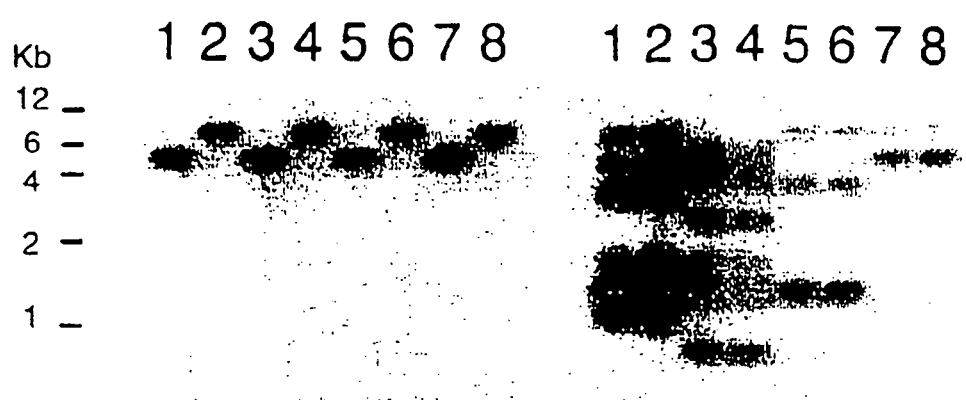

RD1 deletions of *M. bovis* and *M. tuberculosis* are attenuated for virulence in immunocompromised mice. To test if RD1 is essential for virulence in *M. bovis* and *M. tuberculosis*, it was necessary to delete the RD1 (FIG. 1a) from virulent strains, demonstrate loss of virulence, and then restore virulence by complementation with the RD1 DNA. Since the original *M. bovis* parent of BCG was lost in World War I (Grange et al., 1983), we initiated studies with virulent *M. bovis* Ravenel and a variety of virulent *M. tuberculosis* strains. Despite success in generating an unmarked deletion mutant of RD1 in *M. tuberculosis* with a plasmid transformation system[1,2], over 100 independent transformations failed to yield an RD1 deletion in *M. bovis*. As an alternative strategy, specialized transduction (Bardarov et al., 2002)[3] was successfully used to generate RD1 deletion mutants not only in *M. bovis* Ravenel, but also the H37Rv, Erdman, and CDC1551 strains of *M. tuberculosis* (FIG. 12). This deletion represents the largest deletion mutation generated by a targeted disruption in *M. tuberculosis* or *M. bovis* made to date and demonstrates the utility of the specialized transduction system. Moreover, since the parental specialized transducing phage has been shown to infect over 500 clinical *M. tuberculosis* isolates (Jacobs et al., 1987), it should be possible to introduce the RD1 deletion into any *M. tuberculosis* or *M. bovis* isolate of interest.

To determine if the RD1 deletion causes an attenuating phenotype in *M. bovis* and *M. tuberculosis*, the *M. tuberculosis* H37Rv ΔRD1 was inoculated intravenously into immunocompromised mice possessing the SCID (severe combined immunodeficiency) mutation. Groups of ten mice were injected intravenously with either $2\times10^6$ wild type or ΔRD1 strain of *M. tuberculosis* and *M. bovis*, and three mice per group were sacrificed 24 hours later to verify the inoculation doses. All of the SCID mice infected with the parental *M. tuberculosis* or *M. bovis* strain died within 14 to 16 days post-infection (FIG. 12A). In contrast, the SCID mice infected with equal doses of the ΔRD1 strains of *M. tuberculosis* or *M. bovis* were all alive at 25 to 41 days post-infection, demonstrating a highly significant attenuation of the virulence of both strains. It is important to note that BCG-Pasteur kills SCID mice approximately 70 days post-infection (FIG. 13B), suggesting that BCG substrains have acquired additional attenuating mutations which are consistent with the deletion analysis of BCG strains (Behr et al., 1999) and the previous failures to restore virulence with the RD1 region (Mahairas et al., 1996).

Figure 13:
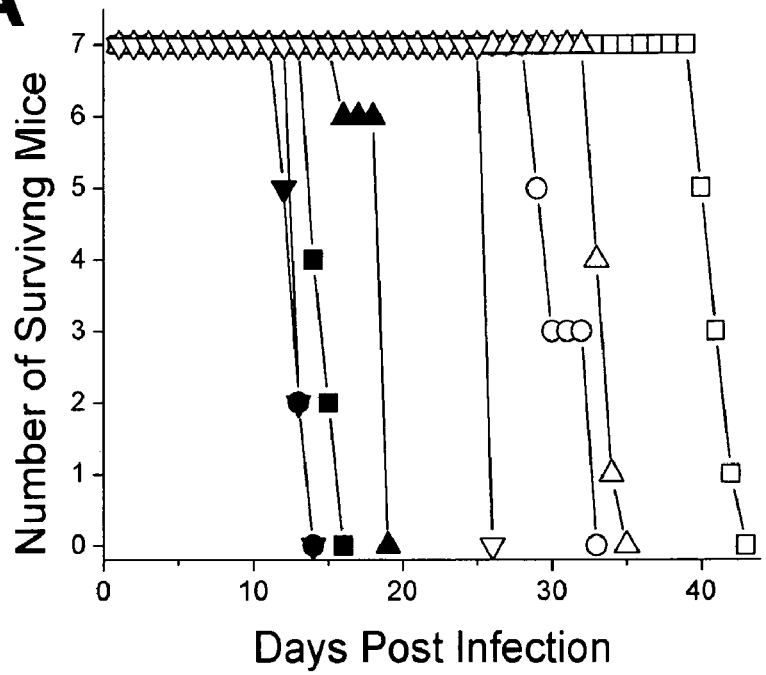
Figure 13:
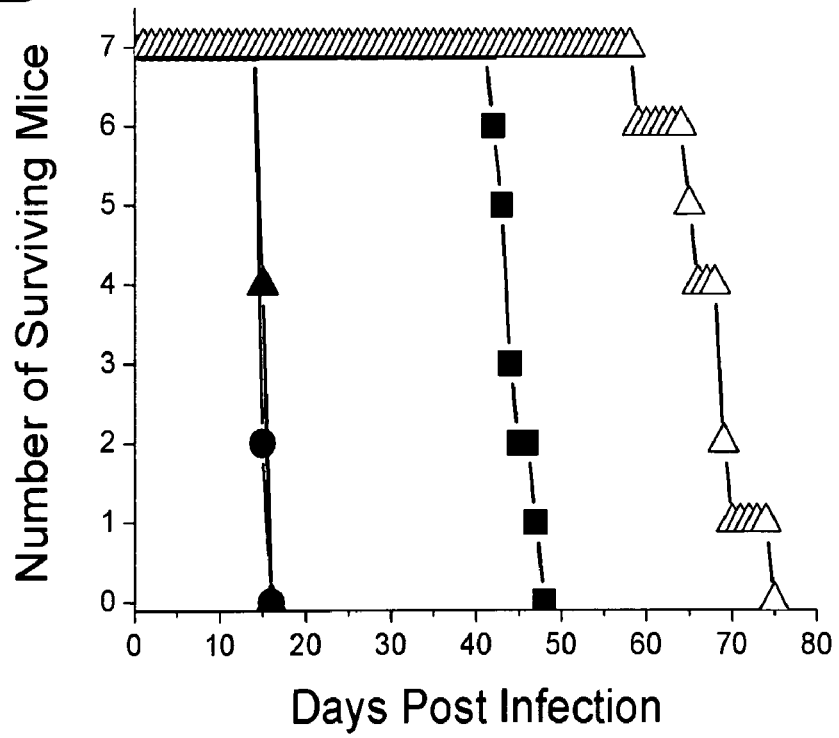

To prove that the attenuation of virulence was due to the RD1 deletion, the *M. tuberculosis* ΔRD1 was transformed with an integrating cosmid, 2F9, containing the RD1 region from *M. tuberculosis* H37Rv[4]. SCID mice were infected as described above and the attenuation for virulence was restored to the parental virulent phenotype (FIG. 13B). These results strongly suggest that the genes deleted from the RD1 region contribute to the virulence phenotype.

The *M. tuberculosis* ΔRD1 is highly attenuated in immunocompetent BALB/c mice. The virulence of the *M. tuberculosis* ΔRD1 mutant was further assessed by intravenous inoculation of immunocompetent BALB/c mice. While the virulent parent *M. tuberculosis* strain killed the BALB/c mice in 10 to 17 weeks post-infections, 100% of mice were alive at 48 weeks and 43 weeks post-infections in two independent experiments (FIG. 13C).

While infection with BCG and *M. tuberculosis* ΔRD1 yielded similar survival results in BALB/c mice, there were substantial differences in the growth kinetics in mice. BCG grew in a limited fashion in lungs, liver and spleen in BALB/c mice during the 22 weeks of the experiment (FIGS. 4B-D). In contrast, the *M. tuberculosis* ΔRD1 strain grew in a fashion indistinguishable from the parental *M. tuberculosis* H37Rv in all mouse organs for the first 8 weeks. Thereafter, mice infected with the parental *M. tuberculosis* failed to contain the infection leading to mortality. Strikingly, mice infected with the *M. tuberculosis* ΔRD1 showed a definite control over infection resulting in significantly prolonged survival of mice (FIGS. 4B-D).

Histopathological examination further demonstrated that the mutant was attenuated in virulence compared to the parent strain H37Rv (FIGS. 5D-F). In contrast to the rapidly progressive infection with the parent strain, the lung lesions caused by the mutant were maximal in mice examined at 8 weeks post-infection. Consolidating granulomatous pneumonia involved an estimated 25-30% of the lung in these mice. Numerous organisms were demonstrated by acid fast staining. The pneumonia subsequently underwent partial resolution. By 14 weeks, and again, at 22 weeks post-infection, the lungs showed peribronchial and perivascular inflammatory cell accumulations and focal, generally non-confluent, granulomas now with a prominent lymphocytes infiltration. The numbers of acid fast *bacilli* were reduced. Liver lesions consisted of low numbers of scattered granulomas. Spleens were smaller, with persistent granulomas in the red pulp. Mice infected with *M. bovis* BCG showed mild lesions in the lung, liver and spleen at all time points (FIG. 5G-I). At longer time intervals post-infection the lesions were fewer in number, and smaller with prominent lymphocytic infiltrations. At 14 weeks post-infection, *M. bovis* BCG was below the level of detection by acid fast staining. In summary, whereas *M. tuberculosis* ΔRD1 initially grew in a manner similar to the parental *M. tuberculosis* H37Rv, this RD1 mutant was limited in the extent of spread of infection, particularly in the lung. This contrasts the extensive and severe damage caused by the parent strain. The subsequent resolving granulomas, localization of the lesions and changes in the composition of the inflammatory cell infiltrations suggested that the mice mounted an effective immune response to combat M. tuberculosis ΔRD1 infection and thereby reduced the numbers of viable organisms.

Early BCG properties: Altered colonial morphotypes and long-term immunogenicity. While frozen stocks of the original BCG strain do not exist, written records do exist describing the early BCG strains, as Dr. Calmette sent the strains to many laboratories. In a study published in 1929, Petroff and colleagues reported that BCG displayed two distinct colony types (Petroff et al., 1929). One morphotype was a smooth (S) phenotype that was flat and corded (like the parental virulent strain) and the second was a rough and raised (R) phenotype. The *M. tuberculosis* ΔRD1 mutant was generated independently four times and consistently yielded a 20 to 50% mixture of two colonial morphotypes on Middlebrook medium without Tween 80 (FIG. 3*b*). The distinction of these two types of morphology could be noted even when the colonies were less than two weeks old, as the rough colonies were constricted and elevated with only a small portion of the base of the colony attached to the agar, while the smooth colonies tended to be flattened and spread out. When colonies grew older, e.g. 6 weeks old, the rough colonies remained more constricted compared to those of smooth colonies. The rough colonies exhibited large folds on the surface (FIG. 3*f-g*), as compared to those of the smooth colonies that exhibited small wrinkles (FIG. 3*e*).

The generation of two distinct colonial morphotypes must be a phenotypic change induced by the deletion of RD1. The morphotypes could not be cloned, as repeated subculturing of either the R or S colonies continued to yield both colonial morphotypes. Moreover, Southern analysis of R and S colonies revealed each morphotype had the same RD1-deleted genotype (FIG. 3D). Furthermore, complementation of *M. tuberculosis* ΔRD1 with the RD1 region restored the mutant phenotype back to the homogenous parental S phenotype (FIG. 3*a-c*). These results suggest that the variable morphotypes resulted directly from the RD1 deletion. It can therefore be postulated that a regulator of colonial morphology is affected by one or more of the deleted genes.

The generation of two distinct colonial morphotypes must be a phenotypic change induced by the deletion of RD1. The morphotypes could not be cloned, as repeated subculturing of either the R or S colonies continued to yield both colonial morphotypes. Moreover, Southern analysis of R and S colonies revealed each morphotype had the same RD1-deleted genotype (FIG. 3D). Furthermore, complementation of *M. tuberculosis* ΔRD1 with the RD1 region restored the mutant phenotype back to the homogenous parental S phenotype (FIG. 3A-C). These results suggest that the variable morphotypes resulted directly from the RD1 deletion. It can therefore be postulated that a regulator of colonial morphology is affected by one or more of the deleted genes.

One of the hallmark characteristics of BCG is its ability to provide protection against aerosolized challenge with virulent *M. tuberculosis*. To test the potential of *M. tuberculosis* ΔRD1 to immunize and protect mice against tuberculous challenge, we used the model of subcutaneous immunization of C57BL/6 mice followed by an aerogenic challenge with virulent *M. tuberculosis* (McGuire et al., 2002). Groups of mice were vaccinated subcutaneously with either $1\times10^6$ BCG 9 or $1\times10^6$ *M. tuberculosis* ΔRD1. Eight months following vaccination, the mice were all healthy, thereby demonstrating attenuation in a third mouse strain. Vaccinated and unvaccinated mice were aerogenically challenged with 200 CFU of the acriflavin-resistant strain of *M. tuberculosis* Erdman. Twenty-eight days after the challenge, the mice were sacrificed and the bacterial burden in the lungs and spleens were determined (see Table 5). Naive mice served as controls. While the acriflavin-resistant *M. tuberculosis* grew to 6.61±0.13 ($\log^{10}$ CFU) in lungs of naive mice, both the BCG-vaccinated and *M. tuberculosis* ΔRD1-vaccinated mice exhibited greater than 1 log protection in lungs with CFU values of 5.07±0.10 ($p<0.001$ relative to controls) and 5.11±0.14 ($p<0.001$), respectively, detected at the four week time point. The *M. tuberculosis* ΔRD1 also protected against hematogenous spread; CFU values in the spleen were 5.26±0.11 for the controls, 4.00±0.33 ($p<0.01$) for the *M. tuberculosis* ΔRD1 immunized mice, and 3.85±0.17($p<0.01$) for the BCG vaccinated animals. Thus, the *M. tuberculosis* ΔRD1 shares long-term immunogenicity like BCG.

TABLE 5

Bacterial burden of virulent *M. tuberculosis* in uninoculated mice and mice inoculated with BCG and H37Rv ΔRD1.

| Vaccination strain | Lung ($\log_{10}$CFU) | Spleen (log10CFU) |
|---|---|---|
| — | 6.61 ± 0.13 | 5.26 ± 0.11 |
| BCG | 5.07 ± 0.10*** | 3.85 ± 0.17** |
| H37Rv ΔRD1 | 5.11 ± 0.14*** | 4.00 ± 0.33** |

**$p < 0.01$;
***$p < 0.001$.

Discussion

BCG is a mutant of *M. bovis* that was isolated over 94 years ago and characterized for its attenuation for virulence in animals. For over 80 years, BCG has been used as a tuberculosis vaccine having been given to 3 billion humans. It is currently the only anti-tuberculous vaccine available for use in humans, yet its precise attenuating mutations and mechanisms of attenuation have never been determined. Previous studies had identified regions of the *M. bovis* chromosome that were absent from BCG, but present in virulent *M. bovis* and *M. tuberculosis* strains (Mahairas et al., 1996; Gordon et al., 2001). An elegant microarray analysis has also demonstrated that there was only one deletion common to all BCG strains; the authors hypothesized this was the primary attenuating mutation in the original BCG strain isolated by Drs. Calmette and Guerin (Behr et al., 1999).

Using a combination of targeted deletion mutagenesis, virulence assays, and complementation analysis, we have been able to unambiguously prove that RD1 is required for virulence for *M. tuberculosis*, and by analogy for *M. bovis*, for the first time.

Moreover, the combination of phenotypes associated with the early BCG strains: i) the attenuation for virulence, ii) the altered colonial morphotypes, and iii) the ability to confer long-term immunogenicity in animals allow us to conclude that the RD1 deletion was the primary attenuating mutation in the original BCG isolate.

With regards to the ΔRD1 mutant histology, at 22 weeks post infection, it was noted that the mutant was limited in the extent of the spread of infection, in contrast to the extensive damage caused by the parental strain. Interestingly, Pethe et al. (2001) determined that *M. tuberculosis* needs to bind and/or invade epithelial cells in order to disseminate and cause widespread destruction of the lung, whilst another study reported that pulmonary M cells can act as a portal of entry to the lung for the *tubercle bacilli* (Teitelbaum, 1999). In relation to in vitro analyses, studies utilizing a model of the alveolar barrier, consisting of pneumocytes and monocytes, described how *M. tuberculosis* infection of the pneumocytes resulted in cytolysis, which disrupted the barrier and allowed more efficient translocation of intracellular *bacilli* (Bermudez et al., 2002).

Notes

[1] The following four primers were used to amplify upstream and downstream flanking sequences (UFS and DFS, respectively) for the construction of the RD1 deletion mutants. UFS was amplified using TH201: GGGGGCG-CACCTCAAACC (SEQ ID NO:5) and TH202: ATGTGC-CAATCGTCGACCAGAA (SEQ ID NO:6). DFS was amplified using TH203: CACCCAGCCGCCCGGAT (SEQ ID NO:7), and TH204: TTCCTGATGCCGCCGTCGA (SEQ ID NO:8). Recognition sequences for different restriction enzymes were included at the ends of each primer to enable easier manipulation.

[2] The unmarked deletion mutant of *M. tuberculosis* H37Rv, mc$^2$4002, was generated by transformation using a sacB counterselection (Snapper et al., 1988; Pelicic et al., 1996; Pavelka et al., 1999). Specifically, the plasmid pJH508 was created by first cloning UFS into KpnI and XbaI sites, then cloning DFS into EcoRI and HindIII sites of pJH12, a pMV261-derived *E. coli*—Mycobacteria shuttle plasmid, to create pJH506 in which UFS and DFS flanked a green fluorescent protein gene (GFPuv, Clonetech) whose expression was driven by the *M. leprae* 18Kd promoter. The UFS-gfp-DFS cassette was sub-cloned into the EcoRV site of plasmid pYUB657 to create pJH508. The first homologous recombination involved the identification of hygromycin resistant colonies, resulting from the transformation of *M. tuberculosis* with pJH508. Southern analysis of the NcoI-digested DNA isolated from hygromycin resistant colonies probed with UFS or DFS, confirmed the presence of a single copy of pJH508 inserted into the *M. tuberculosis* genome. The transformant (mc$^2$4000) identified was then grown in 7H9 broth to saturation, to allow the second homologous recombination to occur, resulting in recombinants that could be selected by plating the culture on 7H10 plates, supplemented with 3% sucrose. Both Southern analysis and PCR of the DNA isolated from sucrose resistant colonies confirmed the RD1 deletion.

[3] Specialized transduction is a mycobacteriophage-based method for the delivery of homologous DNA constructs using conditionally replicating shuttle phasmids (Jacobs et al., 1987; Bardarov et al., 1997; Carriere et al., 1997) has been used successfully for *M. tuberculosis* (Glickman et al., 2000, 2001; Raman et al., 2001). Specifically, a transducing phage phAEKO1 was constructed by inserting UFS and DFS into pJSC347, flanking a hygromycin cassette, to create pJH313. pJH313 was digested with PacI and ligated to phAE159, a temperature-sensitive mycobacteriophage derived from TM4. The transduction was performed by growing *M. tuberculosis* to an O.D.$_{600}$ of 1.0, washing twice with MP buffer (50 mM Tris pH 7.6, 150 mM NaCl, 10 mM MgCL$_2$, 2 mM CaCl$_2$), resuspending into an equal volume of MP buffer and mixing with the transducing phage phAEKO1 at an MOI of 10. The mixtures were incubated at 37° C. overnight, then plated on 7H10 plates supplemented with hygromycin at 50 µg/ml. Hygromycin resistant colonies were analyzed by PCR and Southern analysis, as described above, to confirm the deletion of RD1.

[4] Complementation analyses was performed using the integration proficient cosmids (Skjot et al., 2000; van Pinxteren et al., 2000) pYUB412 made by S. Bardarov, a library made by F. Bange, and cosmid identified and generously provided by S. T. Cole.

EXAMPLE 5

Vaccine Efficacy of a Lysine Auxotroph of *M. Tuberculosis*

In this Example, we describe the in vivo growth phenotype and vaccine efficacy of a lysine auxotrophic mutant of *Mycobacterium tuberculosis* strain H37Rv. An immunization experiment using the mouse model with an aerosol challenge showed that two doses of the *M. tuberculosis* mutant were required to generate protection equivalent to that of the BCG vaccine.

Despite the existence of anti-microbial drugs and a widely used vaccine, *Mycobacterium tuberculosis* remains the primary cause of adult death due to a bacterial agent (Dolin et al., 1994). The emergence of multi-drug resistant strains of *M. tuberculosis*, the variable efficacy of the current vaccine, the bacille-Calmette and Geurin (BCG), and the HIV pandemic have all contributed to a growing global tuberculosis problem.

Several studies have described the development of attenuated auxotrophic strains of BCG and/or *M. tuberculosis* (Guleria et al., 1996); Hondalus et al., 2000; Jackson et al., 1999; Smith et al., 2001). All of these studies utilized single immunization protocols and demonstrated differences in the protective responses thus elicited. In this study, we describe the in vivo growth characteristics of a previously described lysine auxotroph of *M. tuberculosis* H37Rv (Pavelka and Jacobs, 1999), and evaluate the vaccine potential of this mutant by a multiple immunization protocol in a mouse model of the human disease, using an aerosol challenge.

Clearance of the *M. tuberculosis* lysine auxotroph in SCID mice. Female SCID mice were bred at the animal facility of the Albert Einstein College of Medicine. The animals were maintained under barrier conditions and fed sterilized commercial mouse chow and water ad libitum. The *M. tuberculosis* strains Erdman, mc$^2$3026 (ΔlysA::res) (Id.), and mc$^2$3026 bearing pYUB651 (expressing the wild-type lysA gene) were grown in Middlebrook 7H9 broth (Difco) supplemented with 0.05% Tween-80, 0.2% glycerol, 1×ADS (0.5% bovine serum albumin, fraction V (Roche); 0.2% dextrose; and 0.85% NaCl) or on Middlebrook 7H10 or 7H11 solid medium (Difco) supplemented with 0.2% glycerol and 10% OADC (Becton Dickinson). Culture media for the lysine auxotroph were supplemented with 1 mg/ml of L-lysine (for both liquid and solid media), and 0.05% Tween-80 was also added to solid medium. Liquid cultures were grown in 490 cm$^2$ roller bottles (Corning) at 4-6 rpm. Plates were incubated for 3-6 weeks in plate cans. All cultures were incubated at 37° C.

Titered frozen stocks of the bacteria were thawed and diluted appropriately in phosphate buffered saline containing 0.05% Tween-80 (PBST). The bacterial suspensions were plated at the time of injection to confirm the number of viable bacteria. Intravenous injections were given via a lateral tail vein. At various time points post-injection (24 hours, then once weekly), 3 mice were sacrificed, and the lungs, liver, and spleen removed and homogenized separately in PBST using a Stomacher 80 (Tekmar, Cincinnati, Ohio). The homogenates were diluted in PBST and plated to determine the number of CFU/organ. Note that mice were sacrificed at 24 hours post-injection in order to compare the bacterial colony forming units recovered from the mice with the colony forming units in the suspensions at the time of injection. Thus the bacterial counts reported at time zero actually represent the viable bacteria recovered from the mice at 24-hours post-injection.

Figure 14:
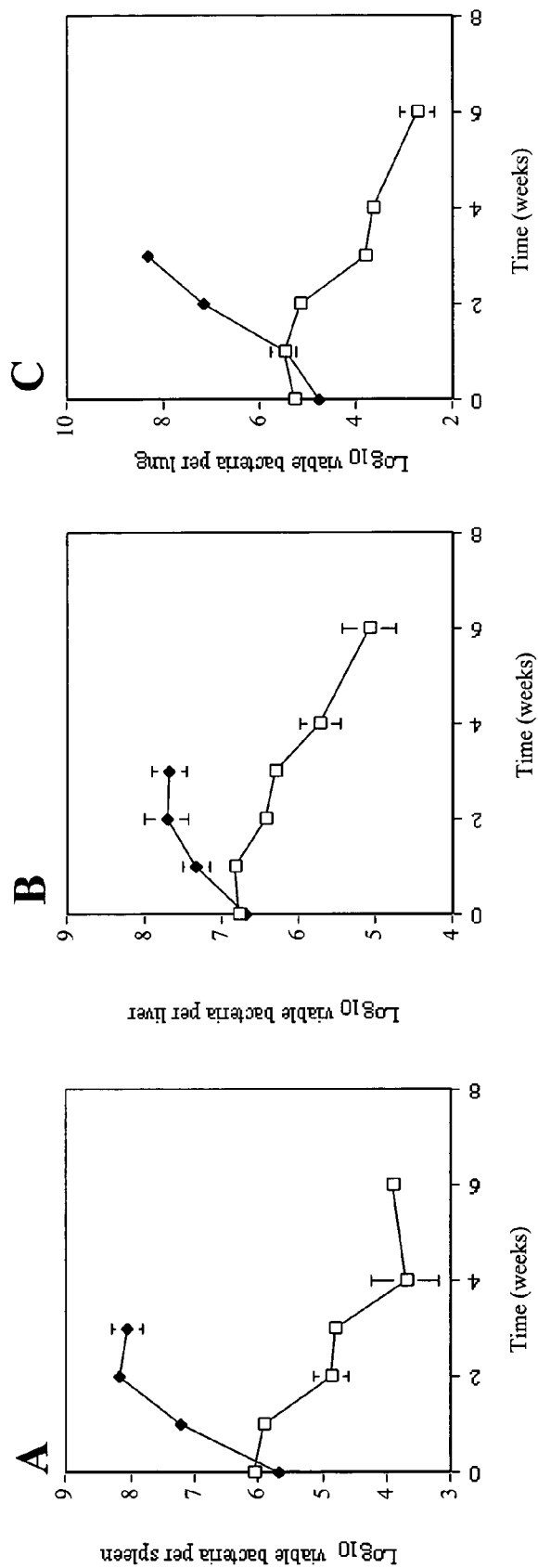
Figure 15:
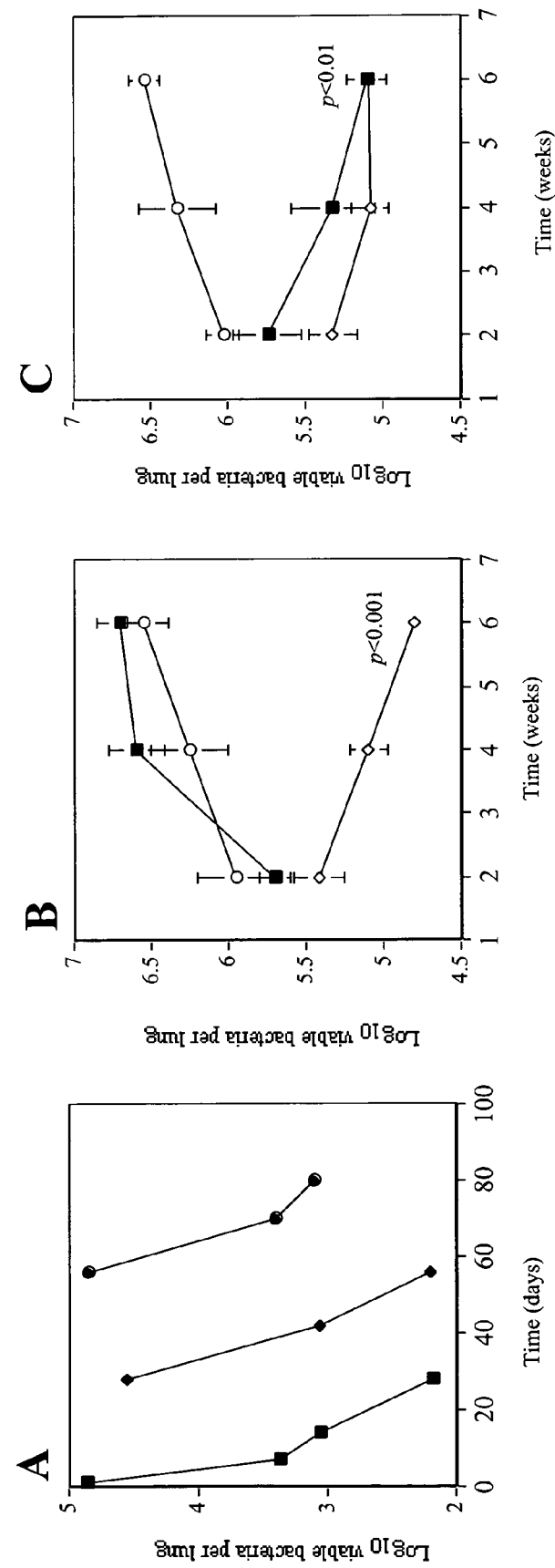
Figure 16:
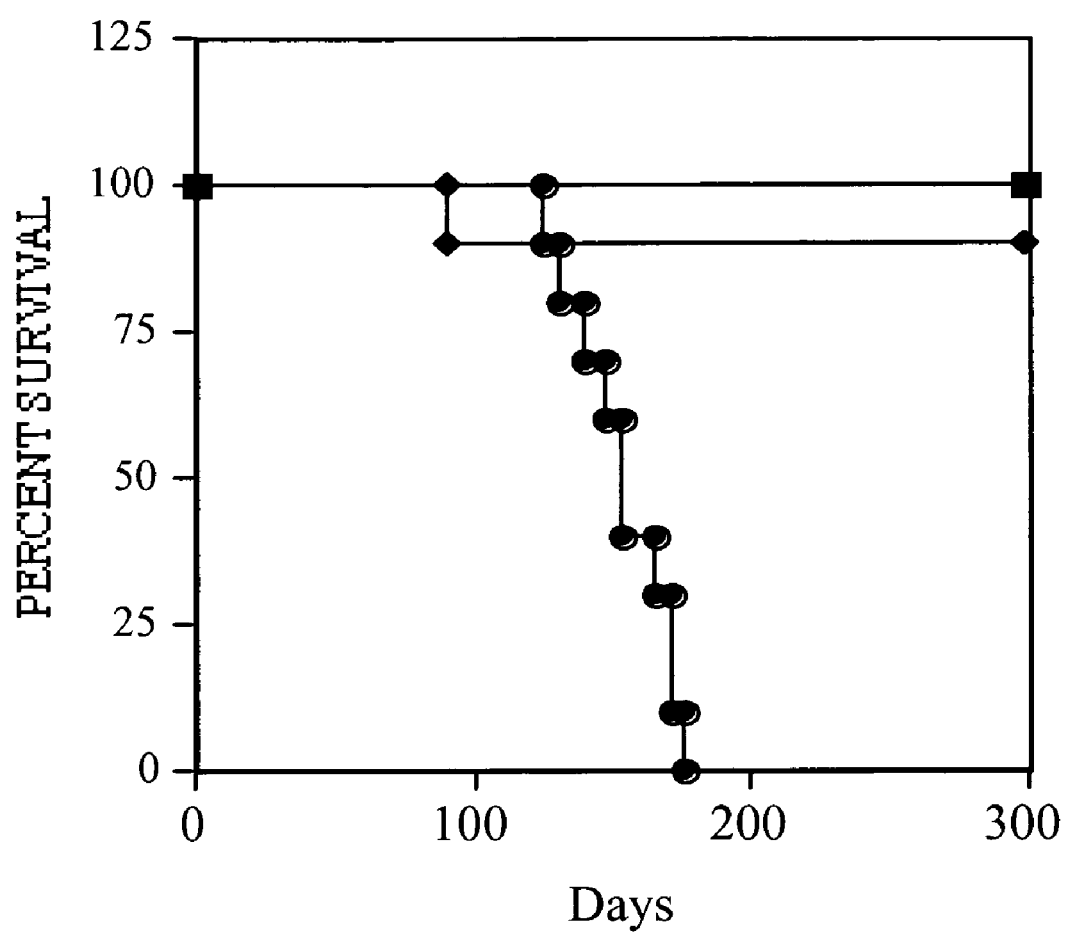

The lysine auxotrophic strain was cleared from and did not appear to grow in the examined organs of the SCID mice, while the complemented strain multiplied extensively (FIG. 14). Interestingly, the auxotrophic inoculum was cleared from the spleens and lungs but persisted somewhat longer in the liver (FIG. 14B). The mice receiving the complemented *M. tuberculosis* mutant died within three weeks of challenge, while the mice given the auxotrophic *M. tuberculosis* mutant did not display any gross organ pathology and survived for at least the duration of the experiment.

Two immunizations with the *M. tuberculosis* lysine auxotroph $mc^2$3026 are required to match the efficacy of vaccination with BCG-Pasteur. We tested the vaccine potential of the lysine auxotroph $mc^2$3026 in the mouse model by means of a virulent aerosol challenge. Female, pathogen-free C57BL/6 mice (Jackson Laboratories, Bar Harbor, Me.) were vaccinated intravenously with ca. $1\times10^6$ CFU of the *M. tuberculosis* lysine auxotroph or BCG-Pasteur suspended in 0.2 ml PBST. Mice vaccinated with $mc^2$3026 were revaccinated at 4 week intervals and the number of viable organisms in the lungs and spleens determined weekly throughout the vaccination period, as described above for the SCID mouse experiments. Five mice were examined at each time point.

Immunized mice were challenged 3 months after the initial vaccination. A frozen aliquot of a *M. tuberculosis* Erdman stock was thawed and diluted in PBST to ca. $1\times10^6$ CFU/ml and 10 ml was introduced into the nebulizer of a Middlebrook aerosol chamber (Glas-Col, Terre Haute, Ind.). The mice were exposed to the infectious aerosol for 30 minutes, inhaling 50-100 CFU into their lungs over this period. Five mice were sacrificed immediately following the challenge period and the lung homogenates were plated to check the amount of the challenge inoculum actually reaching the lungs. Groups of vaccinated and control mice were sacrificed 14, 28, and 42 days later and the lung and spleen homogenates plated to determine the number of viable colony forming units of *M. tuberculosis* Erdman present. Data were analyzed using the Student's t-test and an analysis of variance between several independent means, using the In Stat Statistics program (GraphPad Software, San Diego).

A preliminary experiment demonstrated that a single intravenous immunization of immunocompetent C57BL/6 mice with the *M. tuberculosis* mutant did not generate a significant protective response to the subsequent aerosol challenge with virulent *M. tuberculosis* Erdman. In that experiment, the *M. tuberculosis* auxotroph was rapidly cleared from the mice (FIG. 15A), and the single immunization with the auxotroph was insufficient to reduce the bacterial burden in the lungs and spleens relative to a single immunization with BCG (FIG. 15B).

The failure of the auxotroph to confer protection might have been due to the inability of the mutant to persist long enough, or to synthesize enough antigen to induce an immune response that could significantly restrict the growth of the challenge organisms. One way to circumvent this problem is to give multiple doses of vaccine (Collins, 1991; Homchampa et al., 1992). To this end, mice were intravenously immunized two or three times at four-week intervals with the *M. tuberculosis* lysine auxotroph. In both cases, the vaccine strain was cleared from the lungs and spleens of all the mice at rates similar to that seen with the single immunization experiment (FIG. 15A). Three months after the first immunization the mice were challenged with *M. tuberculosis* Erdman by the aerosol route and the bacterial counts in the lungs and spleens were determined and compared to a BCG-Pasteur immunized control, as well as the sham immunized controls. As seen in FIG. 15C, double immunization with the *M. tuberculosis* lysine auxotroph induced a protective response that was equivalent to that of the BCG control. The reduction in counts in the lung and spleen was equivalent to a 100-fold reduction in bacterial counts compared to the unvaccinated control (FIG. 15C). The results from the triple immunization experiment were essentially similar as those from the double immunization experiment described above (data not shown). Furthermore, mice that were immunized with three doses of the *M. tuberculosis* lysine auxotroph and challenged with virulent *M. tuberculosis* Erdman survived at least as long as the BCG-immunized control mice (FIG. 16).

Several studies have described the development and vaccine efficacy of attenuated mutant strains of *M. tuberculosis* (Jackson et al., 1999; Hondalus et al., 2000; Smith et al., 2001). The first study reported that a purine auxotroph of *M. tuberculosis* was unable to grow in macrophages and was attenuated for growth in both mice and guinea pigs (Jackson et al., 1999). A guinea pig vaccination experiment determined that a single immunization with the auxotroph allowed the animals to restrict the growth of virulent *M. tuberculosis* in the lungs as well as a single immunization with wild-type BCG, following aerosol challenge. However, the reduction in growth of the challenge organism in the spleen afforded by the auxotroph was not as extensive as that afforded by BCG. Another study reported that a leucine auxotroph of *M. tuberculois* Erdman cannot grow in macrophages and is avirulent to immunocompromised SCID mice (Hondalus et al., 2000). Immunocompetent mice vaccinated once with a *M. tuberculosis* leucine mutant did not significantly restrict the growth of the virulent challenge organism in the lungs or spleen as much as the control mice vaccinated with BCG (Id.). However, the mice immunized with the leucine auxotroph survived as long as the BCG immunized controls and exhibited a decreased histopathology relative to that seen in the non-immunized controls (Id.). A third study showed that *M. tuberculosis* proline and tryptophan auxotrophs were attenuated and a single immunization of mice with either of these mutants afforded protection against an intravenous challenge with virulent *M. tuberculosis*, comparable to that for BCG, as indicated by the mean survival times (Smith et al., 2001). In those experiments, mice immunized with pro or trp mutants could restrict the growth of the challenge organisms to the same extent as mice immunized with BCG, although the magnitude of protection in either case (*M. tuberculosis* auxotrophs or BCG) was not as extensive as that seen in the other studies (Id.).

In the present study we have demonstrated that a single immunization of mice with the avirulent *M. tuberculosis* lysine auxotroph did not generate an immune response capable of significantly restricting the growth of virulent *M. tuberculosis* Erdman following an aerogenic challenge. However, administration of a second or a third dose of this vaccine increased protection substantially, as measured by the number of viable bacteria per organ, to a level similar to that achieved with single dose of BCG-Pasteur. This level of protection did not seem to be greatly increased by a third dose of vaccine, although the triply immunized mice survived as long as the control mice immunized with a single dose of BCG-Pasteur. Mice that were immunized twice were not followed to determine mean survival time, but comparing the growth curves of the challenge bacteria following the double and triple immunizations, it seems likely that the survival time for the doubly immunized mice would be much the same as that for the triple-immunized mice.

The previous studies using *M. tuberculosis* auxotrophs as vaccine strains showed substantial variations in their effectiveness. This variability is likely to be due to a number of factors, including the different *M. tuberculosis* background strains used to construct the mutants, different mouse strains used in the various protection studies, and the different challenge organisms and challenge routes used. There was also considerable variation in the protective efficacy of the different vaccines compared to that observed in controls using BCG immunization. These differences pose a number of questions concerning the best indicators of protection, especially in the long term. Should viable bacterial counts or survival be the primary indicator of protection or should both be given equal weight? The results of this study indicate that more than one immunization with a *M. tuberculosis* lysine auxotroph did generate a significant protective response as indicated by both criteria. We believe it is important that multiple immunization protocols be considered in the further development of attenuated *M. tuberculosis* strains as potential human vaccines.

This is the first study demonstrating that a multiple immunization protocol using an auxotroph of *M. tuberculosis* can protect against a highly virulent aerosol challenge compared to that seen for BCG. Since BCG vaccines have shown variable efficacy when tested in humans, an auxotrophic *M. tuberculosis* vaccine might represent an attractive booster vaccine with which to augment childhood BCG immunization.

EXAMPLE 6

Mutants of *Mycobacterium Tuberculosis* HAving Two Attenuating Mutations are Safe and Provide Protection in Mammals Against Challenge from Virulent Mycobacteria The experiments described in this Example employ materials and methods described in the other Examples.

Construction and characterization of *M. tuberculosis* ΔRD1 ΔpanCD (mc$^2$6030). A pantothenate auxotroph of *M. tuberculosis* ΔRD1 was generated by specialized transduction and the strain designated mc$^2$6030. No CFU were detected on 7H11 when 5×10$^{10}$ CFU were plated (repeated twice), suggesting the reversion frequency to be below 10$^{-11}$.

Figure 17:
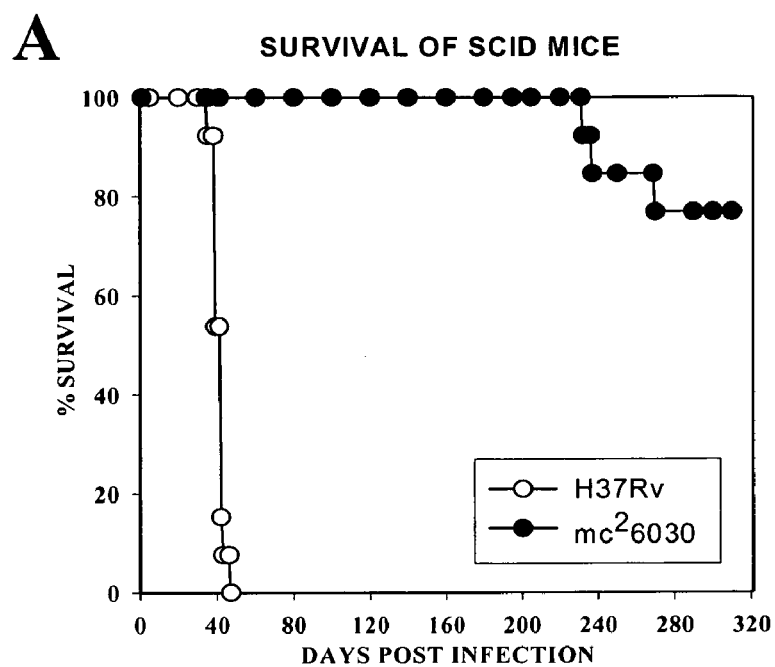
FIG. 17 shows graphs summarizing experimental results establishing that the virulence of strain mc$^2$6030 is highly attenuated in SCID mice and BALB/c mice.
Figure 17:
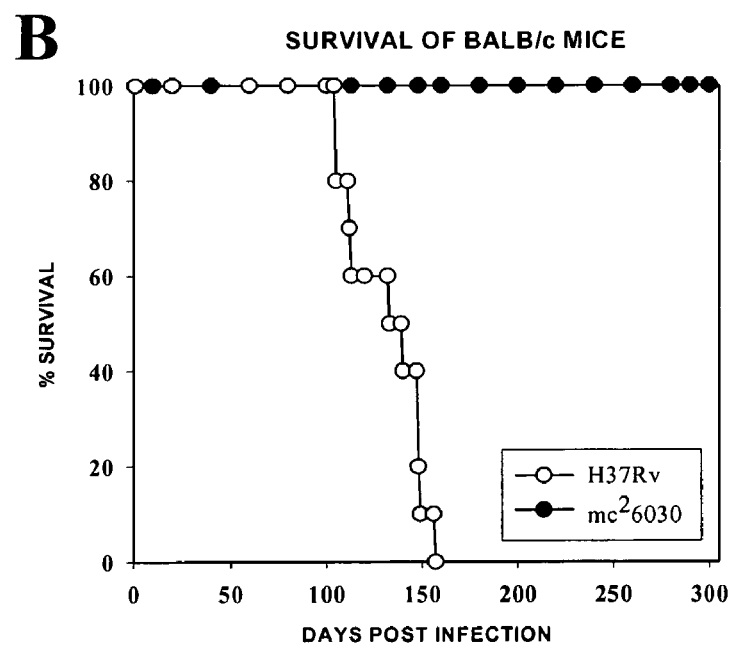
Figure 18:
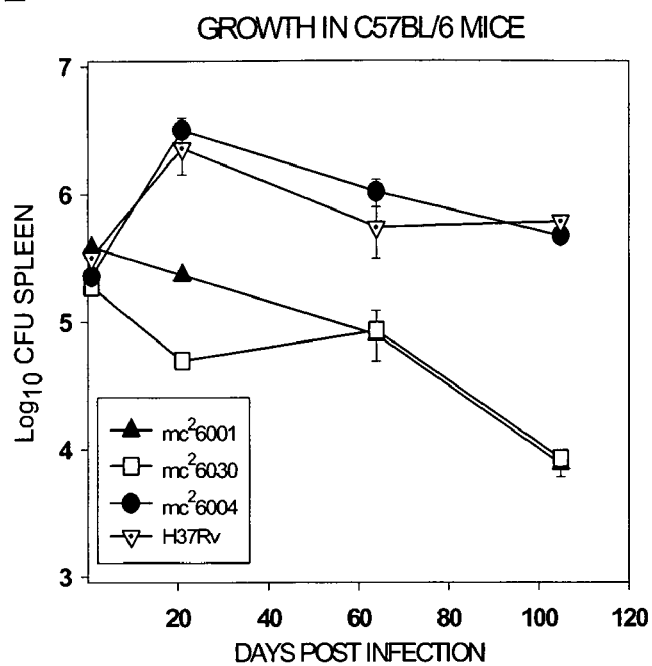
FIG. 18 shows graphs summarizing experimental results measuring growth of various strains of *M. tuberculosis* in spleen (Panel A) and lungs (Panel B) of C57BL/6 mice.
Figure 18:
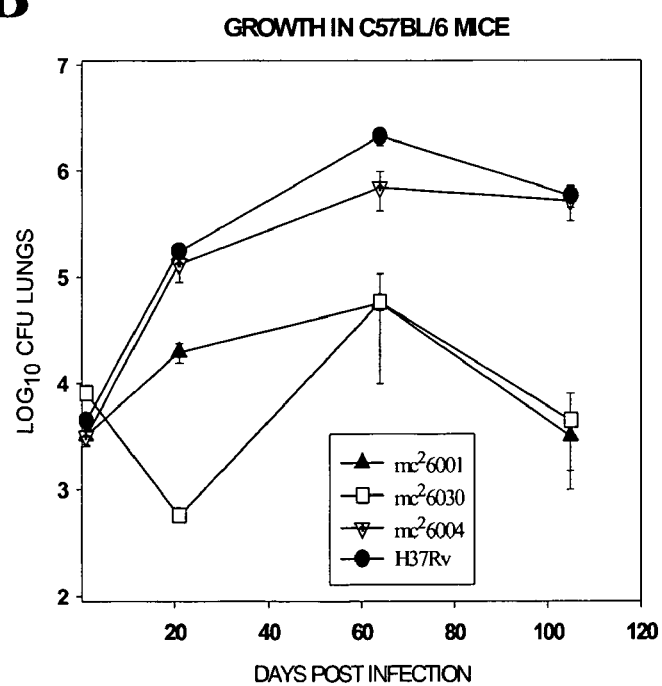

SCID mice infected with 1×10$^2$ CFU H37Rv succumbed to infection in 6 weeks, whereas the mice infected with 1×10$^6$ mc$^2$6030 survived significantly longer with more than 75% of mice surviving for more than 300 days (FIG. 17A). Bacteria isolated from mc$^2$6030-infected mice before they died were all auxotrophs, confirming that there were no revertants under in vivo conditions. In order to assess the safety of mc$^2$6030 in immunocompetent BALB/c mice, we infected mice intravenously with 1×10$^6$ mc$^2$6030 or 1×10$^6$ of wild-type H37Rv. All mice infected with H37Rv succumbed to infection by 150 days, whereas mice infected with mc$^2$6030 survived for more than 300 days (FIG. 17B). In an effort to understand the role of immune responses in controlling infection with the pantothenate mutants, we infected immunocompetent C57B1/6 with 1×10$^6$ CFU of mc$^2$6001 (ΔRD1), mc$^2$6004 (complementing strain), mc$^2$6030 (ΔRD1 ΔpanCD) or wild-type H37Rv. Mice infected with H37Rv and mc$^2$6004 showed progressive growth in all the three organs, whereas mice infected with mc$^2$6030 showed a drop in growth during the first 3 weeks in the lungs and spleen (FIG. 18). Following 3 weeks of infection, the growth pattern of both mc$^2$6001 and mc$^2$6030 were identical in the spleen and lungs. Mice immunized subcutaneously with one or two doses of mc$^2$6030 demonstrated protection against aerosol challenge with virulent *M. tuberculosis*, which was comparable to the protection afforded by BCG vaccination (Table 6). No pantothenate auxotrophs were recovered from spleen or lungs of mice at 1, 2 or 3 months following subcutaneous immunization.

TABLE 6

Bacterial burden of virulent *M. tuberculosis* in uninoculated mice and mice inoculated with BCG or one or two doses of ΔRD1ΔpanCD.

| Experimental Group | Lung CFUs (log$_{10}$) | Spleen CFUs (log10) |
|---|---|---|
| Naive | 5.99 ± 0.09 | 4.94 ± 0.06 |
| ΔRD1ΔpanCD (1 dose) sc | 5.22 ± 0.10* | 4.04 ± 0.15* |
| ΔRD1ΔpanCD (2 doses) sc | 4.86 ± 0.14** | 3.58 ± 0.11** |
| BCG (1 dose) sc | 4.79 ± 0.19** | 3.73 ± 0.27** |

*p < 0.01 relative to controls;
**p < 0.001 relative to controls

Construction and characterization of *M. tuberculosis* ΔlysAΔpanCD (mc$^2$6020). A pantothenate auxotroph of *M. tuberculosis* ΔlysA was generated by specialized transduction and the strain designated mc$^2$6020. No CFU were detected on 7H11 when 5×10$^{10}$ CFU were plated, suggesting the reversion frequency to be below 10$^{-11}$. This double mutant is auxotrophic for both lysine and pantothenate. SCID mice infected with 1×10$^2$ CFU H37Rv succumbed to infection in 6 weeks, whereas the mice infected with 1×10$^6$ mc$^2$6020 survived for more than 400 days with no mortality. In order to assess the safety and growth kinetics of mc$^2$6020 in immunocompetent BALB/c mice, we infected mice intravenously with 1×10$^6$ mc$^2$6020 or 1×10$^6$ of wild-type H37Rv. All mice infected with H37Rv succumbed to infection by 150 days, whereas mice infected with mc$^2$6020 survived for more than 400 days. After 3 weeks following intravenous infection, no colonies of mc$^2$6020 could be recovered from spleen, liver or lungs of infected mice. Interestingly, mice immunized subcutaneously with one or two doses of mc$^2$6020 demonstrated protection against aerosol challenge with virulent *M. tuberculosis*, which was comparable to the protection afforded by BCG vaccination (Table 7). No pantothenate and lysine requiring auxotrophs were recovered from spleen or lungs of mice at 1, 2 or 3 months following subcutaneous immunization. Other studies established that both mc$^2$6020 and mc$^2$6030 protects the a level of protection of mice against TB equivalent to the protection afforded by BCG (FIG. 19).

TABLE 7

Bacterial burden of virulent *M. tuberculosis* in uninoculated mice and mice inoculated with BCG or one or two doses of mc$^2$6020 (ΔlysAΔpanCD) sc or one dose of mc$^2$6020 iv.

| Experimental group | Lung CFUs (log$_{10}$) | Spleen CFUs (log$_{10}$) |
|---|---|---|
| naive | 6.03 ± 0.05$^a$ | 4.84 ± 0.27 |
| BCG (1 dose) sc | 4.76 ± 0.19*** | 3.95 ± 0.18* |
| mc$^2$6020 (1 dose) sc | 5.05 ± 0.06*** | 4.02 ± 0.11* |
| mc$^2$6020 (2 doses) sc | 5.09 ± 0.05*** | 4.06 ± 0.27 |
| mc$^2$6020 (1 dose) iv | 5.06 ± 0.11*** | 4.00 ± 0.15* |

$^a$Mean ± SEM
p < 0.001 =***;
p < 0.05 =*

These data clearly demonstrate the safety and immunogenicity of these two double mutants of *M. tuberculosis* in mice.

The double deletion mutant mc$^2$6030 (ΔRD1ΔpanCD) immunizes and protects SCID mice from aerosolized *M. tuberculosis* challenge. The double deletion mutants were safer than BCG in SCID mice, where all of the SCID mice died before 100 days when inoculated with BCG, 100% and 25% of the mice survived inoculation with mc$^2$6020 and mc$^2$6030, respectively (FIG. 20).

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A mycobacterium in the *Mycobacterium tuberculosis* complex, genetically engineered to be auxotrophic for a vitamin.

2. The mycobacterium of claim 1, wherein the mycobacterium is a *Mycobacterium bovis*.

3. The mycobacterium of claim 1, wherein the mycobacterium is a *Mycobacterium tuberculosis*.

4. The mycobacterium of claim 3, wherein the *M. tuberculosis* exhibits attenuated virulence in a mammal when compared to the *M. tuberculosis* without the deletion.

5. The mycobacterium of claim 3, further comprising a foreign DNA stably integrated into genomic DNA of the *M. tuberculosis*.

6. The mycobacterium of claim 1, wherein the vitamin is pantothenic acid.

7. The mycobacterium of claim 6, wherein the deletion is a ΔpanCD deletion.

8. The mycobacterium of claim 1, 2, 3, 4, 6 or 7, further comprising a deletion controlling production of an amino acid.

9. The mycobacterium of claim 8, wherein the amino acid is lysine.

10. A non-naturally occurring *Mycobacterium tuberculosis* comprising a deletion of the entire RD1 region, wherein the *M. tuberculosis* with the RD1 deletion exhibits attenuated virulence in a mammal when compared to virulent *M. tuberculosis* without the deletion.

11. The *M. tuberculosis* of claim 10, which is genetically engineered.

12. The *M. tuberculosis* of claim 10, wherein the mammal is immunocompromised.

13. The *M. tuberculosis* of claim 10, wherein the RD1 region has at least 95% homology to SEQ ID NO:1.

14. The *M. tuberculosis* of claim 10, further comprising a second deletion.

15. The *M. tuberculosis* of claim 14, wherein the second deletion causes the *M. tuberculosis* to be auxotrophic.

16. The *M. tuberculosis* of claim 15, wherein the second deletion is a region controlling production of a vitamin.

17. The *M. tuberculosis* of claim 16, wherein the vitamin is pantothenic acid.

18. The *M. tuberculosis* of claim 17, wherein the second deletion is a ΔpanCD deletion.

19. The *M. tuberculosis* of claim 15, wherein the second deletion is in a region controlling production of an amino acid.

20. The *M. tuberculosis* of claim 19, wherein the amino acid is lysine.

21. The *M. tuberculosis* of claim 19, wherein the second deletion is a ΔlysA deletion.

22. The *M. tuberculosis* of claim 10, further comprising a foreign DNA stably integrated into genomic DNA of the *M. tuberculosis*.

23. The *M. tuberculosis* of claim 22, wherein the foreign DNA encodes at least one protein or polypeptide selected from the group consisting of an antigen, an enzyme, a lymphokine, an immunopotentiator, and a reporter molecule.

* * * * *

UNITED STATES PATENT AND TRADEMARK OFFICE
CERTIFICATE OF CORRECTION

PATENT NO. : 7,722,861 B2
APPLICATION NO. : 10/351452
DATED : May 25, 2010
INVENTOR(S) : William R. Jacobs et al.

It is certified that error appears in the above-identified patent and that said Letters Patent is hereby corrected as shown below:

In the specification

Column 1, lines 10-16, should read:

-- STATEMENT OF GOVERNMENT SUPPORT

This invention was made with government support under grant number AI26170 awarded by the National Institutes of Health. The government has certain rights in the invention. --

Signed and Sealed this
Third Day of November, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 9454
<212> TYPE: DNA
<213> ORGANISM: Mycobacterium tuberculosis

<400> SEQUENCE: 1

```
gatcgtgggt gccgccgggg ggatgccgcc gatggcaccg ctggccccgt tattgccggc     60
ggcggcagat atcgggttgc acatcattgt cacctgtcag atgagccagg cttacaaggc    120
aaccatggac aagttcgtcg cgcgccgcatt cgggtcgggc gctccgacaa tgttcctttc   180
gggcgagaag caggaattcc catccagtga gttcaaggtc aagcggcgcc cccctggcca   240
ggcatttctc gtctcgccag acggcaaaga ggtcatccag gccccctaca tcgagcctcc   300
agaagaagtg ttcgcagcac ccccaagcgc cggttaagat tatttcattg ccggtgtagc   360
aggacccgag ctcagcccgg taatcgagtt cgggcaatgc tgaccatcgg gtttgtttcc   420
ggctataacc gaacggtttg tgtacgggat acaaatacag ggagggaaga agtaggcaaa   480
tggaaaaaat gtcacatgat ccgatcgctg ccgacattgg cacgcaagtg agcgacaacg   540
ctctgcacgg cgtgacggcc ggctcgacgg cgctgacgtc ggtgaccggg ctggttcccg   600
cgggggccga tgaggtctcc gcccaagcgg cgacggcgtt cacatcggag ggcatccaat   660
tgctggcttc caatgcatcg gcccaagacc agctccaccg tgcgggcgaa gcggtccagg   720
acgtcgcccg cacctattcg caaatcgacg acggcgccgc cggcgtcttc gccgaatagg   780
cccccaacac atcggaggga gtgatcacca tgctgtggca cgcaatgcca ccggagctaa   840
ataccgcacg gctgatggcc ggcgcgggtc cggctccaat gcttgcggcg gccgcgggat   900
ggcagacgct ttcggcggct ctggacgctc aggccgtcga gttgaccgcg cgcctgaact   960
ctctgggaga agcctggact ggaggtggca gcgacaaggc gcttgcggct gcaacgccga  1020
tggtggtctg gctacaaacc gcgtcaacac aggccaagac ccgtgcgatg caggcgacgg  1080
cgcaagccgc ggcatacacc caggccatgg ccacgacgcc gtcgctgccg gagatcgccg  1140
ccaaccacat cacccaggcc gtccttacgg ccaccaactt cttcggtatc aacacgatcc  1200
cgatcgcgtt gaccgagatg gattatttca tccgtatgtg gaaccaggca gccctggcaa  1260
tggaggtcta ccaggccgag accgcggtta acacgctttt cgagaagctc gagccgatgg  1320
cgtcgatcct tgatcccggc gcgagccaga gcacgacgaa cccgatcttc ggaatgccct  1380
cccctggcag ctcaacaccg gttggccagt tgccgccggc ggctacccag accctcggcc  1440
aactgggtga gatgagcggc ccgatgcagc agctgaccca gccgctgcag caggtgacgt  1500
cgttgttcag ccaggtgggc ggcaccggcg gcggcaaccc agccgacgag gaagccgcgc  1560
agatgggcct gctcggcacc agtccgctgt cgaaccatcc gctggctggt ggatcaggcc  1620
ccagcgcggg cgcgggcctg ctgcgcgcgg agtcgctacc tggcgcaggt gggtcgttga  1680
cccgcacgcc gctgatgtct cagctgatcg aaaagccggt tgccccctcg gtgatgccgg  1740
```

```
cggctgctgc cggatcgtcg gcgacgggtg gcgccgctcc ggtgggtgcg ggagcgatgg    1800
gccagggtgc gcaatccggc ggctccacca ggccgggtct ggtcgcgccg gcaccgctcg    1860
cgcaggagcg tgaagaagac gacgaggacg actgggacga agaggacgac tggtgagctc    1920
ccgtaatgac aacagacttc ccggccaccc gggccggaag acttgccaac attttggcga    1980
ggaaggtaaa gagagaaagt agtccagcat ggcagagatg aagaccgatg ccgctaccct    2040
cgcgcaggag gcaggtaatt tcgagcggat ctccggcgac ctgaaaaccc agatcgacca    2100
ggtggagtcg acggcaggtt cgttgcaggg ccagtggcgc ggcgcggcgg ggacggccgc    2160
ccaggccgcg gtggtgcgct tccaagaagc agccaataag cagaagcagg aactcgacga    2220
gatctcgacg aatattcgtc aggccggcgt ccaatactcg agggccgacg aggagcagca    2280
gcaggcgctg tcctcgcaaa tgggcttctg acccgctaat acgaaagaa acggagcaaa    2340
aacatgacag agcagcagtg gaatttcgcg ggtatcgagg ccgcggcaag cgcaatccag    2400
ggaaatgtca cgtccattca ttccctcctt gacgagggga agcagtccct gaccaagctc    2460
gcagcggcct ggggcggtag cggttcggag gcgtaccagg gtgtccagca aaaatgggac    2520
gccacggcta ccgagctgaa caacgcgctg cagaacctgg cgcggacgat cagcgaagcc    2580
ggtcaggcaa tggcttcgac cgaaggcaac gtcactggga tgttcgcata gggcaacgcc    2640
gagttcgcgt agaatagcga aacacgggat cgggcgagtt cgaccttccg tcggtctcgc    2700
cctttctcgt gtttatacgt ttgagcgcac tctgagaggt tgtcatggcg gccgactacg    2760
acaagctctt ccggccgcac gaaggtatgg aagctccgga cgatatgcaa gcgcagccgt    2820
tcttcgaccc cagtgcttcg tttccgccgg cgcccgcatc ggcaaaccta ccgaagccca    2880
acggccagac tccgccccg acgtccgacg acctgtcgga gcggttcgtg tcggccccgc    2940
cgccgccacc cccacccca cctccgcctc cgccaactcc gatgccgatc gccgcaggag    3000
agccgccctc gccggaaccg gccgcatcta aaccacccac acccccatg cccatcgccg    3060
gacccgaacc ggccccaccc aaaccaccca caccccat gcccatcgcc ggacccgaac    3120
cggccccacc caaaccaccc acacctccga tgcccatcgc cggacctgca cccacccaa    3180
ccgaatccca gttggcgccc cccagaccac cgacaccaca aacgccaacc ggagcgccgc    3240
agcaaccgga atcaccggcg ccccacgtac cctcgcacgg gccacatcaa ccccggcgca    3300
ccgcaccagc accgccctgg gcaaagatgc caatcggcga accccccgcc gctccgtcca    3360
gaccgtctgc gtccccggcc gaaccaccga cccggcctgc cccccaacac tcccgacgtg    3420
cgcgccgggg tcaccgctat cgcacagaca ccgaacgaaa cgtcgggaag gtagcaactg    3480
gtccatccat ccaggcgcgg ctgcgggcag aggaagcatc cggcgcgcag ctcgcccccg    3540
gaacggagcc ctcgccagcg ccgttgggcc aaccgagatc gtatctggct ccgcccaccc    3600
gccccgcgcc gacagaacct ccccccagcc cctcgccgca gcgcaactcc ggtcggcgtg    3660
ccgagcgacg cgtccacccc gatttagccg cccaacatgc cgcggcgcaa cctgattcaa    3720
ttacggccgc aaccactggc ggtcgtcgcc gcaagcgtgc agcgccggat ctcgacgcga    3780
cacagaaatc cttaaggccg gcggccaagg ggccgaaggt gaagaaggtg aagcccccaga    3840
aaccgaaggc cacgaagccg cccaaagtgg tgtcgcagcg cggctggcga cattgggtgc    3900
atgcgttgac gcgaatcaac ctgggcctgt caccccgacga aagtacgag ctggacctgc    3960
acgctcgagt ccgccgcaat ccccgcgggt cgtatcagat cgccgtcgtc ggtctcaaag    4020
gtggggctgg caaaaccacg ctgacagcag cgttgggggtc gacgttggct caggtgcggg    4080
ccgaccggat cctggctcta gacgcggatc caggcgccgg aaacctcgcc gatcgggtag    4140
```

```
ggcgacaatc gggcgcgacc atcgctgatg tgcttgcaga aaaagagctg tcgcactaca    4200
acgacatccg cgcacacact agcgtcaatg cggtcaatct ggaagtgctg ccggcaccgg    4260
aatacagctc ggcgcagcgc gcgctcagcg acgccgactg gcatttcatc gccgatcctg    4320
cgtcgaggtt ttacaacctc gtcttggctg attgtgggc cggcttcttc gacccgctga     4380
cccgcggcgt gctgtccacg gtgtccggtg tcgtggtcgt ggcaagtgtc tcaatcgacg    4440
gcgcacaaca ggcgtcggtc gcgttggact ggttgcgcaa caacggttac caagatttgg    4500
cgagccgcgc atgcgtggtc atcaatcaca tcatgccggg agaacccaat gtcgcagtta    4560
aagacctggt gcggcatttc gaacagcaag ttcaacccgg ccgggtcgtg gtcatgccgt    4620
gggacaggca cattgcggcc ggaaccgaga tttcactcga cttgctcgac cctatctaca    4680
agcgcaaggt cctcgaattg ccgcagcgc tatccgacga tttcgagagg gctggacgtc     4740
gttgagcgca cctgctgttg ctgctggtcc taccgccgcg ggggcaaccg ctgcgcggcc    4800
tgccaccacc cgggtgacga tcctgaccgg cagacggatg accgatttgg tactgccagc    4860
ggcggtgccg atggaaactt atattgacga caccgtcgcg gtgctttccg aggtgttgga    4920
agacacgccg gctgatgtac tcggcggctt cgactttacc gcgcaaggcg tgtgggcgtt    4980
cgctcgtccc ggatcgccgc cgctgaagct cgaccagtca ctcgatgacg ccggggtggt    5040
cgacgggtca ctgctgactc tggtgtcagt cagtcgcacc gagcgctacc gaccgttggt    5100
cgaggatgtc atcgacgcga tcgccgtgct tgacgagtca cctgagttcg accgcacggc    5160
attgaatcgc tttgtggggg cggcgatccc gcttttgacc gcgcccgtca tcgggatggc    5220
gatgcgggcg tggtgggaaa ctgggcgtag cttgtggtgg ccgttggcga ttggcatcct    5280
ggggatcgct gtgctggtag gcagcttcgt cgcgaacagg ttctaccaga gcggccacct    5340
ggccgagtgc ctactggtca cgacgtatct gctgatcgca accgccgcag cgctggccgt    5400
gccgttgccg cgcggggtca actcgttggg ggcgccacaa gttgccggcg ccgctacggc    5460
cgtgctgttt ttgaccttga tgacgcgggg cggccctcgg aagcgtcatg agttggcgtc    5520
gtttgccgtg atcaccgcta tcgcggtcat cgcggccgcc gctgccttcg gctatggata    5580
ccaggactgg gtccccgcgg ggggatcgc attcgggctg ttcattgtga cgaatgcggc     5640
caagctgacc gtcgcggtcg cgcggatcgc gctgccgccg attccggtac ccggcgaaac    5700
cgtggacaac gaggagttgc tcgatcccgt cgcgaccccg gaggctacca gcgaagaaac    5760
cccgacctgg caggccatca tcgcgtcggt gcccgcgtcc gcggtccggc tcaccgagcg    5820
cagcaaactg gccaagcaac ttctgatcgg atacgtcacg tcgggcaccc tgattctggc    5880
tgccggtgcc atcgcggtcg tggtgcgcgg gcacttcttt gtacacagcc tggtggtcgc    5940
gggtttgatc acgaccgtct gcggatttcg ctcgcggctt tacgccgagc gctggtgtgc    6000
gtgggcgttg ctgcggcgga cggtcgcgat tccgacgggt ctgacggcca aactcatcat    6060
ctggtacccg cactatgcct ggctgttgtt gagcgtctac ctcacggtag ccctggttgc    6120
gctcgtggtg gtcgggtcga tggctcacgt ccggcgcgtt tcaccggtcg taaaacgaac    6180
tctggaattg atcgacggcg ccatgatcgc tgccatcatt cccatgctgc tgtggatcac    6240
cggggtgtac gacacggtcc gcaatatccg gttctgagcc ggatcggctg attggcggtt    6300
cctgacagaa catcgaggac acggcgcagg tttgcatacc ttcggcgccc gacaaattgc    6360
tgcgattgag cgtgtggcgc gtccggtaaa atttgctcga tggggaacac gtataggaga    6420
tccggcaatg gctgaaccgt tggccgtcga tcccaccggc ttgagcgcag cggccgcgaa    6480
```

```
attggccggc ctcgttttc  cgcagcctcc ggcgccgatc gcggtcagcg aacggattc   6540
ggtggtagca gcaatcaacg agaccatgcc aagcatcgaa tcgctggtca gtgacgggct  6600
gcccggcgtg aaagccgccc tgactcgaac agcatccaac atgaacgcgg cggcggacgt  6660
ctatgcgaag accgatcagt cactgggaac cagtttgagc cagtatgcat tcggctcgtc  6720
gggcgaaggc ctggctggcg tcgcctcggt cggtggtcag ccaagtcagg ctacccagct  6780
gctgagcaca cccgtgtcac aggtcacgac ccagctcggc gagacggccg ctgagctggc  6840
accccgtgtt gttgcgacgg tgccgcaact cgttcagctg gctccgcacg ccgttcagat  6900
gtcgcaaaac gcatccccca tcgctcagac gatcagtcaa accgcccaac aggccgccca  6960
gagcgcgcag ggcggcagcg gcccaatgcc cgcacagctt gccagcgctg aaaaaccggc  7020
caccgagcaa gcggagccgg tccacgaagt gacaaacgac gatcagggcg accagggcga  7080
cgtgcagccg gccgaggtcg ttgccgcggc acgtgacgaa ggcgccggcg catcaccggg  7140
ccagcagccc ggcgggggcg ttcccgcgca agccatggat accggagccg gtgcccgccc  7200
agcggcgagt ccgctggcgg cccccgtcga tccgtcgact ccggcaccct caacaaccac  7260
aacgttgtag accgggcctg ccagcggctc cgtctcgcac gcagcgcctg ttgctgtcct  7320
ggcctcgtca gcatgcggcg gccagggccc ggtcgagcaa cccggtgacg tattgccagt  7380
acagccagtc cgcgacggcc acacgctgga cggccgcgtc agtcgcagtg tgcgcttggt  7440
gcagggcaat ctcctgtgag tgggcagcgt aggcccggaa cgcccgcaga tgagcggcct  7500
cgcggccggt agcggtgctg gtcatgggct tcatcagctc gaaccacagc atgtgccgct  7560
catcgcccgg tggattgaca tccaccggcg ccggcggcaa caagtcgagc aaacgctgat  7620
cggtagtgtc ggccagctga gccgccgcg  aggggtcgac gacctccagc cgcgaccggc  7680
ccgtcatttt gccgctctcc ggaatgtcat ctggctccag cacaatcttg gccacaccgg  7740
gatccgaact ggccaactgc tccgcggtac cgatcaccgc ccgcagcgtc atgtcgtgga  7800
aagccgccca ggcttgcacg gccaaaaccg ggtaggtggc acagcgtgca atttcgtcaa  7860
ccgggattgc gtgatccgcg ctggccaagt acaccttatt cggcaattcc atcccgtcgg  7920
gtatgtaggc cagcccatag ctgttggcca cgacgatgga accgtcggtg gtcaccgcgg  7980
tgatccagaa gaacccgtag tcgcccgcgt tgttgtcgga cgcgttgagc gccgccgcga  8040
tgcgtcgcgc caaccgcagc gcatcaccgc ggccacgctg gcgggcgctg gcagctgcag  8100
tggcggcgtc gcgtgccgcc cgagccgccg acaccgggat catcgacacc ggcgtaccgt  8160
catctgcaga ctcgctgcga tcgggtttgt cgatgtgatc ggtcgacggc gggcgggcag  8220
gaggtgccgt ccgcgccgag gccgcccgcg tgctcggtgc cgccgccttg tccgaggtag  8280
ccaccggcgc ccgcccagtg gcagcatgcg accccgcgcc cgaggccgcg gccgtaccca  8340
cgctcgaacg cgcgcccgct cccacggcgg taccgctcgg cgcggcggcc gccgcccgtg  8400
cgcccgggac accggacgcc gcagccggcg tcaccgacgc ggcggattcg tccgcatggg  8460
caggccccga ctgcgtcccc ccgcccgcat gctggcccgg cacaccaggt tgctccgcca  8520
acgccgcggg tttgacgtgc ggcgccggct cgcccctgg  ggtgcccggt gttgctggac  8580
cagacggacc gggagtggcc ggtgtaaccg gctgggccc  aggcgatggc gccggtgccg  8640
gagcggctg  cgggtgtgga gcgggagctg gggtaacggg cgtggccggg gttgccggtg  8700
tggccggggc gaccgggggg gtgaccggcg tgatcggggt tggctcgcct ggtgtgcccg  8760
gtttgaccgg ggtcaccggg gtgaccggct tgccggggt  caccggcgtg acggagtgc   8820
cgggcgttgg tgtgatcgga gttaccggcg ctcccgggat gggtgtgatt ggggttcccg  8880
```

```
gggtgatcgg ggttcccggg gtgatcgggg ttcccggtgt gcccggtgtg cccggggatg      8940
gcacgaccag ggtaggcacg tctgggggtg gcggcgactt ctgctgaagc aaatcctcga      9000
gtgcgttctt cggaggtttc caattcttgg attccagcac ccgctcagcg gtctcggcga      9060
ccagactgac attggcccca tgcgtcgccg tgaccaatga attgatggcg gtatggcgct      9120
catcagcatc caggctaggg tcattctcca ggatatcgat ctcccgttga gcgccatcca      9180
cattattgcc gatatcggat ttagcttgct caatcaaccc ggcaatatgc ctgtgccagg      9240
taatcaccgt ggcgagataa tcctgcagcg tcatcaattg attgatgttt gcacccaggg      9300
cgccgttggc agcattggcg gcgccgccgg accataggcc gccttcgaag acgtggcctt      9360
tctgctggcg gcaggtgtcc aatacatcgg tgaccctttg caaaacctgg ctatattcct      9420
gggcccggtc atagaaagtg tcttcatcgg cttc                                  9454

<210> SEQ ID NO 2
<211> LENGTH: 1298
<212> TYPE: DNA
<213> ORGANISM: Mycobacterium tuberculosis

<400> SEQUENCE: 2
ggtctagcag ctcgcccgcg ttttcgggca caaatgccgg atcgtggccc atgtcgatcg        60
gtttgttgta agcgtcgaca aacacgatcc gcggctggta tgtgcgggcc cgggcgtcgt       120
ccatcgtcgc gtacgcaatc agaatccacc gatcccccgg atgcaccaag tgcgcggcgg       180
caccgttgat gccaatcaca ccactgccgc gttcgccggt gatcgcgtag gtgaccagtc       240
gagcaccgtt gtcgatatcg acgatggtta cctgttcgcc ttccagcagg tcggcggcgt       300
ccatcaagtc ggcatcgatg gtcaccgagc cgacgtagtg caggtcggcg caggtcaccg       360
tggcgcggtg gatcttcgac ttcagcatcg tccgtaacat cagtttctcc aatgtgattc       420
gaggattgcc cggtatccgt ccgggcggtc ggtgccggcg aaagttccga tttcaatcgc       480
aatgttgtcc agcagcctgg tggtgccaag ccgggcagca accagcagcc gaccggaacc       540
gttgagcggc atcgggccaa gcccgatatc gcgcagctcc aggtagtcga ccgccacgcc       600
gggtgcagcg tcgagcaccg cacgggcggc atccagcgcg gcctgcgcgc cagccgttgc       660
cgcatgcgct gcgccgtta gcgcgccga gagcgcgacg gccgccgcac gctgggccgg         720
gtccaggtag cggttgcgcg acgacatcgc cagcccgtcg gcttcgcgca cggtcggcac       780
gccgaccacc gcgacatcga ggttgaagtc cgcgaccagc tgccggatca gcaccagctg       840
ctggtagtcc ttctcaccga agaacacccg atccgggcgc acgatctgca gcagctttag       900
cacgaccgtc agcacgccgg cgaaatgggt tggccgcggg ccgccctcga gttcggcggc       960
caacggaccg ggttgcacgg tggtgcgcag gccgtcggga tacatcgccg cggtagttgg      1020
cgtgaaagcg atttccacgc cttcggcccg cagttgcgcc aggtcgtcgt ccggggtgcg      1080
gggataggcg tcgagatctt ccccggcacc gaattgcatc gggttgacga agatcgacac      1140
gacgacgacc gatccgggca cccgcttggc cgcacgcacc aacgcgaggt ggccttcgtg      1200
cagcgcaccc atagtaggca ccaacatcac tcgccggccg gtgagtcgca gtgcgcgact      1260
gacatcggcg acatccccg gtgccgagta cacattga                              1298

<210> SEQ ID NO 3
<211> LENGTH: 771
<212> TYPE: DNA
<213> ORGANISM: Mycobacterium tuberculosis
```

<400> SEQUENCE: 3

```
aacgggcgat gagccgggac gcgtcgatgt accgcgccgc cgccgggctg caccggctgt      60
gcgacagcct atccggagca caggttcgcg acgtggcttg tcgccgcgat ttcgaggacg     120
tggcgctcac gctggtcgcg cagagcgtga ccgccgccgc cttggcccgc accgaaagcc     180
gtggctgcca tcatcgcgcg gagtacccgt gcaccgtgcc ggagcaggca cgcagcatcg     240
tggtccgggg agccgacgac gcaaatgcgg tgtgtgtcca ggcgctagtg gcggtgtgct     300
gatggggtta tccgactggg agctggctgc ggctcgagca gcaatcgcgc gtgggctcga     360
cgaggacctc cggtacggcc cggatgtcac cacattggcg acggtgcctg ccagtgcgac     420
gaccaccgca tcgctggtga cccgggaggc cggtgtggtt gccggattgg atgtcgcgct     480
gctgacgctg aacgaagtcc tgggcaccaa cggttatcgg gtgctcgacc gcgtcgagga     540
cggcgcccgg gtgccgccgg agaggcact tatgacgctg aagcccaaa cgcgcggatt      600
gttgaccgcc gagcgcacca tgttgaacct ggtcggtcac ctgtcgggaa tcgccaccgc     660
gacggccgcg tgggtcgatg ctgtgcgcgg gaccaaagcg aaaatccgcg atacccgtaa     720
gacgctgccc ggcctgcgcg cgctgcaaaa atacgcggtg cgtaccggtg g              771
```

<210> SEQ ID NO 4
<211> LENGTH: 1255
<212> TYPE: DNA
<213> ORGANISM: Mycobacterium tuberculosis

<400> SEQUENCE: 4

```
gtgaacgagc tgctgcactt agcgccgaat gtgtggccgc gcaatactac tcgcgatgaa      60
gtcggtgtgg tctgcatcgc aggaattcca ctgacgcagc tcgcccagga gtacgggacc     120
ccgctgttcg tcatcgacga ggacgacttt cgctcgcgct gccgagaaac cgccgcggcc     180
tttggaagtg gggcgaacgt gcactatgcc gccaaggcgt tcctgtgcag cgaagtagcc     240
cggtggatca gcgaagaagg gctctgtctg gacgtttgca ccggtgggga gttggcggtc     300
gcgctgcacg ctagctttcc gcccgagcga attaccttgc acggcaacaa caaatcggtc     360
tcagagttga ccgctgcggt caaagccgga gtcggccata ttgtcgtcga ttcgatgacc     420
gagatcgagc gcctcgacgc catcgcgggc gaggccggaa tcgtccagga tgtcctggtg     480
cgtctcaccg tcggtgtcga ggcgcacacc cacgagttca tctccaccgc gcacgagacg     540
cgtcagccac atcggttcgc agatcttcga cgtggacggc ttcgaactcg ccgcgcaccg     600
tgtcatcggc ctgctacgcg acgtcgtcgg cgagttcggt cccgaaaaga cggcacagat     660
cgcgaccgtc gatctcggtg gcggcttggg catctcgtat ttgccgtccg acgacccacc     720
gccgatagcc gagctcgcgg ccaagctggg taccatcgtg agcgacgagt caacggccgt     780
ggggctgccg acgcccaagc tcgttgtgga gcccggacgc gccatcgccg gaccgggcac     840
catcacgttg tatgaggtcg gcaccgttaa ggacgtcgat gtcagcgcca cagcgcatcg     900
acgttacgtc agtgtcgacg gcggcatgag cgacaacatc cgcaccgcgc tctacggcgc     960
gcagtatgac gtccggctgg tgtctcgagt cagcgacgcc ccgccggtac cggcccgtct    1020
ggtcggaaag cactgcgaaa gtggcgatat catcgtgcgg gacacctggg tgcccgacga    1080
tattcggccc ggcgatctgg ttgcggttgc cgccaccggc gcttactgct attcgctgtc    1140
gagtcgttac aacatggtcg gccgtcccgc tgtggtagcg gtgcacgcgg gcaacgctcg    1200
cctggtcctg cgtcgggaga cggtcgacga tttgctgagt ttggaagtga ggtga         1255
```

```
<210> SEQ ID NO 5
<211> LENGTH: 18
<212> TYPE: DNA
<213> ORGANISM: Artificial
<220> FEATURE:
<223> OTHER INFORMATION: primer

<400> SEQUENCE: 5
gggggcgcac ctcaaacc                                                 18

<210> SEQ ID NO 6
<211> LENGTH: 22
<212> TYPE: DNA
<213> ORGANISM: Artificial
<220> FEATURE:
<223> OTHER INFORMATION: primer

<400> SEQUENCE: 6
atgtgccaat cgtcgaccag aa                                            22

<210> SEQ ID NO 7
<211> LENGTH: 17
<212> TYPE: DNA
<213> ORGANISM: Artificial
<220> FEATURE:
<223> OTHER INFORMATION: primer

<400> SEQUENCE: 7
cacccagccg cccggat                                                  17

<210> SEQ ID NO 8
<211> LENGTH: 20
<212> TYPE: DNA
<213> ORGANISM: Artificial
<220> FEATURE:
<223> OTHER INFORMATION: primer

<400> SEQUENCE: 8
ttcctgatgc cgccgtctga                                               20

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
gtgcagcgcc atctctca                                                 18

<210> SEQ ID NO 10
<211> LENGTH: 18
<212> TYPE: DNA
<213> ORGANISM: Artificial
<220> FEATURE:
<223> OTHER INFORMATION: primer

<400> SEQUENCE: 10
gttcaccggg atggaacg                                                 18

<210> SEQ ID NO 11
<211> LENGTH: 18
<212> TYPE: DNA
<213> ORGANISM: Artificial
<220> FEATURE:
<223> OTHER INFORMATION: primer
```

```
-continued

<400> SEQUENCE: 11
cccggctcgg tgtgggat                                                 18

<210> SEQ ID NO 12
<211> LENGTH: 18
<212> TYPE: DNA
<213> ORGANISM: Artificial
<220> FEATURE:
<223> OTHER INFORMATION: primer

<400> SEQUENCE: 12
gcgcggtatg cccggtag                                                 18
```